United States Patent
Cohen et al.

(10) Patent No.: US 10,457,715 B2
(45) Date of Patent: *Oct. 29, 2019

(54) OPTOGENETIC PROBES FOR MEASURING MEMBRANE POTENTIAL

(71) Applicants: President and Fellows of Harvard College, Cambridge, MA (US); The Governors of the University of Alberta, Edmonton (CA)

(72) Inventors: Adam E. Cohen, Cambridge, MA (US); Daniel Hochbaum, Cambridge, MA (US); Peng Zou, Cambridge, MA (US); Samouil Leon Farhi, Cambridge, MA (US); Robert Earl Campbell, Edmonton (CA); Yongxin Zhao, Edmondton (CA); Daniel Jed Harrison, Edmondton (CA)

(73) Assignees: President and Fellows of Harvard College, Cambridge, MA (US); The Governors of the University of Alberta, Edmonton (CA)

( * ) Notice: Subject to any disclaimer, the term of this patent is extended or adjusted under 35 U.S.C. 154(b) by 227 days.

This patent is subject to a terminal disclaimer.

(21) Appl. No.: 15/362,594

(22) Filed: Nov. 28, 2016

(65) Prior Publication Data
US 2017/0313757 A1    Nov. 2, 2017

Related U.S. Application Data

(63) Continuation of application No. 14/742,648, filed on Jun. 17, 2015, now Pat. No. 9,518,103.

(60) Provisional application No. 62/013,775, filed on Jun. 18, 2014.

(51) Int. Cl.
| | | |
|---|---|---|
| *C07K 14/705* | (2006.01) | |
| *G01N 21/64* | (2006.01) | |
| *G01N 33/566* | (2006.01) | |
| *C07K 14/215* | (2006.01) | |

(52) U.S. Cl.
CPC .......... *C07K 14/705* (2013.01); *C07K 14/215* (2013.01); *G01N 21/6428* (2013.01); *G01N 33/566* (2013.01); *G01N 2021/6441* (2013.01); *G01N 2333/726* (2013.01)

(58) Field of Classification Search
None
See application file for complete search history.

(56) References Cited

U.S. PATENT DOCUMENTS

| | | |
|---|---|---|
| 4,293,652 A | 10/1981 | Cohen |
| 5,290,699 A | 3/1994 | Oesterhelt et al. |
| 5,661,035 A | 8/1997 | Tsien et al. |
| 5,925,523 A | 7/1999 | Dove et al. |
| 6,107,066 A | 8/2000 | Tsien et al. |
| 6,200,759 B1 | 3/2001 | Dove et al. |
| 6,243,197 B1 | 6/2001 | Schalz |
| 6,885,492 B2 | 4/2005 | DeSimone et al. |
| 6,898,004 B2 | 5/2005 | Shimizu et al. |
| 6,972,892 B2 | 12/2005 | DeSimone et al. |
| 6,991,910 B2 | 1/2006 | Adorante et al. |
| 7,459,333 B2 | 12/2008 | Richards et al. |
| 7,560,709 B2 | 7/2009 | Kimura et al. |
| 7,736,897 B2 | 6/2010 | Tao et al. |
| 7,964,853 B2 | 6/2011 | Araya |
| 8,202,699 B2 | 6/2012 | Hegemann et al. |
| 8,273,722 B2 | 9/2012 | Ladine et al. |
| 8,401,609 B2 | 3/2013 | Deisseroth et al. |
| 8,532,398 B2 | 9/2013 | Filkins et al. |
| 8,562,658 B2 | 10/2013 | Shoham et al. |
| 8,580,937 B2 | 11/2013 | Spudich et al. |
| 8,603,790 B2 | 12/2013 | Deisseroth et al. |
| 8,617,876 B2 | 12/2013 | Farrar et al. |
| 8,647,870 B2 | 2/2014 | Hegemann et al. |
| 8,716,447 B2 | 5/2014 | Deisseroth et al. |
| 9,057,734 B2 | 6/2015 | Cohen et al. |
| 9,207,237 B2 | 12/2015 | Cohen et al. |
| 9,518,103 B2 | 12/2016 | Cohen et al. |
| 9,702,874 B2 | 7/2017 | Cohen et al. |
| 9,791,455 B2 | 10/2017 | Cohen et al. |
| 10,077,463 B2 | 9/2018 | Cohen et al. |
| 10,161,937 B2 | 12/2018 | Cohen et al. |
| 2002/0021490 A1 | 2/2002 | Kasahara et al. |
| 2005/0202398 A1 | 9/2005 | Hegemann et al. |

(Continued)

FOREIGN PATENT DOCUMENTS

| | | |
|---|---|---|
| EP | 1 970 446 A1 | 9/2008 |
| EP | 2 023 127 A1 | 2/2009 |

(Continued)

OTHER PUBLICATIONS

Gong et al., "Enhanced Archaerhodopsin Fluorescent Protein Voltage Indicators", Jun. 19, 2013, PLoS ONE, 8(6): e66959. doi: 10.1371/journal.pone.0066959.*
Addgene information for plasmid #45188, Retrieved from < http://www.addgene.org/45188/ > on Feb. 7, 2019.*
Addgene informatin for plasmid #35514, retreived from < http://www.addgene.org/35514/> on Feb. 7, 2019.*
Airaksinen et al., "Modified base compositions at degenerate positions of a mutagenic oligonucleotide enhance randomness in site-saturation mutagenesis", Nuc. Acid Res., 1998, vol. 26, No. 2, pp. 576-581.*
Folz et al., "Substrate specificity of Eukaryotic Singal Peptidase", JBC, 1988, vol. 263, No. 4, pp. 2070-2078.*
International Preliminary Report on Patentability for PCT/US2016/013384, dated Jul. 27, 2017.

(Continued)

*Primary Examiner* — Suzanne M Noakes
(74) *Attorney, Agent, or Firm* — Wolf, Greenfield & Sacks, P.C.

(57) ABSTRACT

Provided herein are variants of an archaerhodopsin useful for application such as optical measurement of membrane potential. The present invention also relates to polynucleotides encoding the variants; nucleic acid constructs, vectors, cells comprising the polynucleotides, and cells comprising the polypeptides; and methods of using the variants.

16 Claims, 16 Drawing Sheets

Specification includes a Sequence Listing.

(56) References Cited

U.S. PATENT DOCUMENTS

| | | |
|---|---|---|
| 2007/0087959 A1 | 4/2007 | Sfeir et al. |
| 2009/0142852 A1 | 6/2009 | Friedrich et al. |
| 2009/0229669 A1 | 9/2009 | Birge et al. |
| 2009/0268511 A1 | 10/2009 | Birge et al. |
| 2010/0120043 A1 | 5/2010 | Sood et al. |
| 2011/0165681 A1 | 7/2011 | Boyden et al. |
| 2011/0200568 A1 | 8/2011 | Ikeda et al. |
| 2013/0170026 A1 | 7/2013 | Cohen et al. |
| 2013/0224756 A1 | 8/2013 | Cohen et al. |
| 2014/0093907 A1 | 4/2014 | Miller et al. |
| 2014/0120557 A1 | 5/2014 | Xie et al. |
| 2014/0135382 A1 | 5/2014 | Spudich et al. |
| 2014/0295413 A1 | 10/2014 | Cohen et al. |
| 2015/0004637 A1 | 1/2015 | Cohen et al. |
| 2015/0285820 A1 | 10/2015 | Cohen et al. |
| 2015/0369740 A1 | 12/2015 | Cohen et al. |
| 2016/0069876 A1 | 3/2016 | Cohen et al. |
| 2016/0208308 A1 | 7/2016 | Cohen et al. |
| 2018/0031553 A1 | 2/2018 | Cohen et al. |
| 2018/0031572 A1 | 2/2018 | Cohen et al. |

FOREIGN PATENT DOCUMENTS

| | | |
|---|---|---|
| EP | 2 112 510 A1 | 10/2009 |
| JP | 2009-018772 A | 1/2009 |
| JP | 2009-065848 A | 4/2009 |
| JP | 2010-538603 A | 12/2010 |
| JP | 2012-014066 A | 1/2012 |
| WO | WO 01/59446 A2 | 8/2001 |
| WO | WO 01/83701 A2 | 11/2001 |
| WO | WO 2004/063326 A2 | 7/2004 |
| WO | WO 2007/019398 A1 | 2/2007 |
| WO | WO 2007/131180 A2 | 11/2007 |
| WO | WO 2007/139201 A1 | 12/2007 |
| WO | WO 2008/149055 A1 | 12/2008 |
| WO | WO 2010/027446 A2 | 3/2010 |
| WO | WO 2010/056970 A2 | 5/2010 |
| WO | WO 2012/027358 A1 | 3/2012 |

OTHER PUBLICATIONS

Extended European Search Report for EP 15809987.9, dated Nov. 8, 2017.

Anderson et al., Simultaneous fluorescence-activated cell sorter analysis of two distinct transcriptional elements within a single cell using engineered green fluorescent proteins. Proc Natl Acad Sci USA. Aug. 6, 1996;93(16):8508-11.

Brunner et al., New photolabeling and crosslinking methods. Annu Rev Biochem. 1993;62:483-514.

El Muslemany et al., Photoactivated bioconjugation between ortho-azidophenols and anilines: a facile approach to biomolecular photopatterning. J Am Chem Soc. Sep. 10, 2014;136(36):12600-6. doi: 10.1021/ja503056x. Epub Aug. 29, 2014.

Emmert-Buck et al., Laser capture microdissection. Science. Nov. 8, 1996;274(5289):998-1001.

Espina et al., Laser-capture microdissection. Nat Protoc. 2006;1(2):586-603.

Fors et al., Fabrication of unique chemical patterns and concentration gradients with visible light. J Am Chem Soc. Sep. 25, 2013;135(38):14106-9. doi: 10.1021/ja408467b. Epub Sep. 11, 2013.

Henriksen, Quantitative imaging cytometry: instrumentation of choice for automated cellular and tissue analysis. Nature Methods 2010;7. doi:10.1038/nmeth.f.302.

Hochbaum et al., All-optical electrophysiology in mammalian neurons using engineered microbial rhodopsins. Nat Methods. Aug. 2014;11(8):825-33. doi: 10.1038/nmeth.3000. Epub Jun. 22, 2014.

Hou et al., Temporal dynamics of microbial rhodopsin fluorescence reports absolute membrane voltage. Biophys J. Feb. 4, 2014;106(3):639-48. doi: 10.1016/j.bpj.2013.11.4493.

Hribar et al., Light-assisted direct-write of 3D functional biomaterials. Lab Chip. Jan. 21, 2014;14(2):268-75. doi: 10.1039/c3lc50634g. Epub Nov. 20, 2013.

Kamegaya et al., Evaluation of photochemical tissue bonding for closure of skin incisions and excisions. Lasers Surg Med. Oct. 2005;37(4):264-70.

Kloxin et al., Synthesis of photodegradable hydrogels as dynamically tunable cell culture platforms. Nat Protoc. Dec. 2010;5(12):1867-87. doi: 10.1038/nprot.2010.139. Epub Nov. 4, 2010.

Kluger et al., Chemical cross-linking and protein-protein interactions—a review with illustrative protocols. Bioorg Chem. Dec. 2004;32(6):451-72.

Lu et al., Single cell deposition and patterning with a robotic system. PLoS One. Oct. 21, 2010;5(10):e13542. doi: 10.1371/journal.pone.0013542.

Matsuda et al., Development of surface photochemical modification method for micropatterning of cultured cells. J Biomed Mater Res. Jun. 1995;29(6):749-56.

Moffat et al., A lentiviral RNAi library for human and mouse genes applied to an arrayed viral high-content screen. Cell. Mar. 24, 2006;124(6):1283-98.

Onoe et al., Cellular microfabrication: observing intercellular interactions using lithographically-defined DNA capture sequences. Langmuir. May 29, 2012;28(21):8120-6. doi: 10.1021/la204863s. Epub May 16, 2012.

Ozaki et al., A quantitative image cytometry technique for time series or population analyses of signaling networks. PLoS One. Apr. 1, 2010;5(4):e9955. doi: 10.1371/journal.pone.0009955.

Root et al., Genome-scale loss-of-function screening with a lentiviral RNAi library. Nat Methods. Sep. 2006;3(9):715-9.

Shin et al., Photodegradable hydrogels for capture, detection, and release of live cells. Angew Chem Int Ed Engl. Jul. 28, 2014;53(31):8221-4. doi: 10.1002/anie.201404323. Epub Jun. 16, 2014.

Soman et al., Digital microfabrication of user-defined 3D microstructures in cell-laden hydrogels. Biotechnol Bioeng. Nov. 2013;110(11):3038-47. doi: 10.1002/bit.24957. Epub Jun. 3, 2013.

Tamura et al., Optical cell separation from three-dimensional environment in photodegradable hydrogels for pure culture techniques. Sci Rep. 2014; 4: 4793. Published online May 7, 2014. doi: 10.1038/srep04793.

Venkatachalam et al., Flash Memory: Photochemical Imprinting of Neuronal Action Potentials onto a Microbial Rhodopsin. J. Am. Chem. Soc., 2014;136(6):2529-37. DOI: 10.1021/ja411338t.

Yamahira et al., Collagen Surfaces Modified with Photo-Cleavable Polyethylene Glycol-Lipid Support Versatile Single-Cell Arrays of Both Non-adherent and Adherent Cells. Macromol. Biosci., Dec. 2014;14:1670-6. doi:10.1002/mabi.201400312.

Yang et al., A public genome-scale lentiviral expression library of human ORFs. Nat Methods. Jun. 26, 2011;8(8):659-61. doi: 10.1038/nmeth.1638.

Invitation to Pay Additional Fees for PCT/US2012/066303, dated Mar. 21, 2013.

International Search Report and Written Opinion for PCT/US2012/066303, dated May 28, 2013.

International Preliminary Report on Patentability for PCT/US2012/066303, dated Jun. 5, 2014.

International Search Report and Written Opinion for PCT/US2011/048793, dated Dec. 13, 2011.

International Preliminary Report on Patentability for PCT/US2011/048793, dated Mar. 7, 2013.

Invitation to Pay Additional Fees for PCT/US2015/036181, dated Oct. 27, 2015.

International Search Report and Written Opinion for PCT/US2015/036181, dated Jan. 11, 2016.

International Preliminary Report on Patentability for PCT/US2015/036181, dated Dec. 29, 2016.

Invitation to Pay Additional Fees for PCT/US2016/013384, dated Mar. 30, 2016.

International Search Report and Written Opinion for PCT/US2016/013384, dated Jun. 6, 2016.

Akemann et al., Imaging neural circuit dynamics with a voltage-sensitive fluorescent protein. J Neurophysiol. Oct. 2012;108(8):2323-37. doi: 10.1152/jn.00452.2012. Epub Jul. 18, 2012.

(56) References Cited

OTHER PUBLICATIONS

Akemann et al., Two-photon voltage imaging using a genetically encoded voltage indicator. Sci Rep. 2013;3:2231. doi: 10.1038/srep02231.
Ataka et al., A genetically targetable fluorescent probe of channel gating with rapid kinetics. Biophys J. Jan. 2002;82(1 Pt 1):509-16.
Atasoy et al., A FLEX switch targets Channelrhodopsin-2 to multiple cell types for imaging and long-range circuit mapping. J Neurosci. Jul. 9, 2008;28(28):7025-30. doi: 10.1523/JNEUROSCI.1954-08.2008.
Baker et al., Genetically encoded fluorescent sensors of membrane potential. Brain Cell Biol. Aug. 2008;36(1-4):53-67.
Baker et al., Three fluorescent protein voltage sensors exhibit low plasma membrane expression in mammalian cells. J Neurosci Methods. Mar. 30, 2007;161(1):32-8.
Barondeau et al., Mechanism and energetics of green fluorescent protein chromophore synthesis revealed by trapped intermediate structures. Proc Natl Acad Sci U S A. Oct. 14, 2003;100(21):12111-6. Epub Oct. 1, 2003.
Bean, The action potential in mammalian central neurons. Nat Rev Neurosci. Jun. 2007;8(6):451-65.
Béjà et al., Proteorhodopsin phototrophy in the ocean. Nature. Jun. 14, 2001;411(6839):786-9.
Béjà et al., Bacterial rhodopsin: evidence for a new type of phototrophy in the sea. Science. Sep. 15, 2000;289(5486):1902-6.
Bergo et al., Conformational changes detected in a sensory rhodopsin II-transducer complex. J Biol Chem. Sep. 19, 2003;278(38):36556-62.
Bernstein et al., Optogenetics and thermogenetics: technologies for controlling the activity of targeted cells within intact neural circuits. Curr Opin Neurobiol. Feb. 2012;22(1):61-71. doi: 10.1016/j.conb.2011.10.023. Epub Nov. 24, 2011.
Boyden et al., Millisecond-timescale, genetically targeted optical control of neural activity. Nat Neurosci. Sep. 2005;8(9):1263-8. Epub Aug. 14, 2005.
Brack et al., Picosecond time-resolved absorption and fluorescence dynamics in the artificial bacteriorhodopsin pigment BR6.11. Biophys J. Aug. 1993;65(2):964-72.
Canepari et al., Combining calcium imaging with other optical applications. Cold Spring Harbor Protocols. 2013. pbd. Top066167.
Cans et al., Positioning Lipid Membrane Domains in Giant Vesicles by Micro-organization of Aqueous Cytoplasm Mimic. J. Am. Chem. Soc., 2008;130(23):7400-7406.
Cao et al., Genetically targeted optical electrophysiology in intact neural circuits. Cell. Aug. 15, 2013;154(4):904-13. doi: 10.1016/j.cell.2013.07.027. Epub Aug. 8, 2013.
Cardin et al., Targeted optogenetic stimulation and recording of neurons in vivo using cell-type-specific expression of Channelrhodopsin-2. Nat Protoc. Feb. 2010;5(2):247-54. doi: 10.1038/nprot.2009.228. Epub Jan. 21, 2010.
Carlson et al., Circular permutated red fluorescent proteins and calcium ion indicators based on mCherry. Protein Eng Des Sel. Dec. 2013;26(12):763-72. doi: 10.1093/protein/gzt052. Epub Oct. 22, 2013.
Chanda et al., A hybrid approach to measuring electrical activity in genetically specified neurons. Nat Neurosci. Nov. 2005;8(11):1619-26. Epub Oct. 2, 2005.
Chen et al., Paired-pulse depression of unitary quantal amplitude at single hippocampal synapses. Proc Natl Acad Sci U S A. Jan. 27, 2004;101(4):1063-8. Epub Jan. 13, 2004.
Chen et al., Ultrasensitive fluorescent proteins for imaging neuronal activity. Nature. Jul. 18, 2013;499(7458):295-300. doi: 10.1038/nature12354.
Chien et al., Photostick: a method for selective isolation of target cells from culture. Chem Sci. Mar. 2015;6(3):1701-1705.
Chow et al., High-performance genetically targetable optical neural silencing by light-driven proton pumps. Nature. Jan. 7, 2010;463(7277):98-102.
Chung et al., Diagnostic potential of laser-induced autofluorescence emission in brain tissue. J Korean Med Sci. Apr. 1997;12(2):135-42.

Depry et al., Multiplexed visualization of dynamic signaling networks using genetically encoded fluorescent protein-based biosensors. Pflugers Arch. Mar. 2013;465(3):373-81. doi: 10.1007/s00424-012-1175-y. Epub Nov. 9, 2012.
Derossi et al., Cell internalization of the third helix of the Antennapedia homeodomain is receptor-independent. J Biol Chem. Jul. 26, 1996;271(30):18188-93.
Diester et al., An optogenetic toolbox designed for primates. Nat Neurosci. Mar. 2011;14(3):387-97. doi: 10.1038/nn.2749. Epub Jan. 30, 2011.
Dioumaev et al., Photocycle of Exiguobacterium sibiricum rhodopsin characterized by low-temperature trapping in the IR and time-resolved studies in the visible. J Phys Chem B. Jun. 20, 2013;117(24):7235-53. doi: 10.1021/jp402430w. Epub Jun. 10, 2013.
Dioumaev et al., Proton transfers in the photochemical reaction cycle of proteorhodopsin. Biochemistry.Apr. 30, 2002;41(17):5348-58.
Dioumeav et al., Proton transport by proteorhodopsin requires that the retinal Schiff base counterion Asp-97 be anionic. Biochemistry. Jun. 3, 2003;42(21):6582-7.
Dooley et al., Imaging dynamic redox changes in mammalian cells with green fluorescent protein indicators. J Biol Chem. May 21, 2004;279(21):22284-93. Epub Feb. 25, 2004.
Enami et al., Crystal structures of archaerhodopsin-1 and -2: Common structural motif in archaeal light-driven proton pumps. J Mol Biol. May 5, 2006;358(3):675-85.
Flock et al., Optical properties of Intralipid: a phantom medium for light propagation studies. Lasers Surg Med. 1992;12(5):510-9.
Friedrich et al., Proteorhodopsin is a light-driven proton pump with variable vectoriality. J Mol Biol. Aug. 30, 2002;321(5):821-38.
Fromherz et al., ANNINE-6plus, a voltage-sensitive dye with good solubility, strong membrane binding and high sensitivity. Eur Biophys J. Apr. 2008;37(4):509-14.
Furuta et al., Brominated 7-hydroxycoumarin-4-ylmethyls: photolabile protecting groups with biologically useful cross-sections for two photon photolysis. Proc Natl Acad Sci U S A. Feb. 16, 1999;96(4):1193-200.
Gabriel et al., Direct observation in the millisecond time range of fluorescent molecule asymmetrical interaction with the electropermeabilized cell membrane. Biophys J. Nov. 1997;73(5):2630-7.
Genbank submission, Accession No. AAA72184.1. Apr. 27, 1993. Last accessed Dec. 1, 2015.
Genbank Submission; NIH/NCBI, Accession No. AAY82897. Ewers et al., Jun 1, 2006. 1 page.
Genbank Submission; NIH/NCBI, Accession No. NC_010364.1. Pfeiffer et al., Jun. 10, 2013. 1 page.
Genbank Submission; NIH/NCBI, Accession No. P29563. Uegaki et al., Oct. 29, 2014. 3 pages.
Genbank Submission; NIH/NCBI, Accession No. P69051. Sugiyama et al., Oct. 29, 2014. 3 pages.
Genbank Submission; NIH/NCBI, Accession No. P96787. Ihara et al., Oct. 29, 2014. 3 pages.
Genbank Submission; NIH/NCBI, Accession No. Z35086.1. Seidel et al., Sep. 9, 2004. 2 pages.
Genbank Submission; NIH/NCBI, Accession No. AAG01180. Idnurm et al., Mar. 21, 2001. 1 page.
Genbank Submission; NIH/NCBI, Accession No. AAG42454. Wang et al., Dec. 26, 2000. 1 page.
Genbank Submission; NIH/NCBI, Accession No. AF349981. Béjà et al., May 11, 2004. 1 page.
Genbank Submission; NIH/NCBI, Accession No. AF349983. Béjà et al., May 11, 2004. 1 page.
Genbank Submission; NIH/NCBI, Accession No. BAA06678. Tateno et al., Feb. 7, 1999. 1 page.
Genbank Submission; NIH/NCBI, Accession No. GU045593.1. Chow et al., Jan. 6, 2010. 1 page.
Genbank Submission; NIH/NCBI, Accession No. HM367071. Han et al. , Apr. 13, 2011. 1 page.
Genbank Submission; NIH/NCBI, Accession No. M11720.1. Dunn et al., Apr 26, 1993. 1 page.

(56) References Cited

OTHER PUBLICATIONS

Giovannoni et al., Proteorhodopsin in the ubiquitous marine bacterium SAR11. Nature. Nov. 3, 2005;438(7064):82-5.
Gong et al., Imaging neural spiking in brain tissue using FRET-opsin protein voltage sensors. Nat Commun. Apr. 22, 2014;5:3674. doi: 10.1038/ncomms4674.
Gradinaru et al., Molecular and cellular approaches for diversifying and extending optogenetics. Cell. Apr. 2, 2010;141(1):154-65.
Hoffmann et al., Photoactive mitochondria: in vivo transfer of a light-driven proton pump into the inner mitochondrial membrane of Schizosaccharomyces pombe. Proc Natl Acad Sci U S A. Sep. 27, 1994;91(20):9367-71.
Huggins et al., Optimal experimental design for sampling voltage on dendritic trees in the low-SNR regime. J Comput Neurosci. Apr. 2012;32(2):347-66. doi: 10.1007/s10827-011-0357-5. Epub Aug. 23, 2011.
Huys et al., Efficient estimation of detailed single-neuron models. J Neurophysiol. Aug. 2006;96(2):872-90. Epub Apr. 19, 2006.
Ichas et al., Mitochondria are excitable organelles capable of generating and conveying electrical and calcium signals. Cell. Jun. 27, 1997;89(7):1145-53.
Ihara et al., Evolution of the archaeal rhodopsins: evolution rate changes by gene duplication and functional differentiation. J Mol Biol. Jan. 8, 1999;285(1):163-74.
Ingenhoven et al., Fluorescent labelled analogues of neuropeptide Y for the characterization of cells expressing NPY receptor subtypes. J Recept Signal Transduct Res. Jan.-May 1997;17(1-3):407-18.
Jin et al., Single action potentials and subthreshold electrical events imaged in neurons with a fluorescent protein voltage probe. Neuron. Sep. 6, 2012;75(5):779-85. doi: 10.1016/j.neuron.2012.06.040.
Johnson et al., Localization of mitochondria in living cells with rhodamine 123. Proc Natl Acad Sci U S A. Feb. 1980;77(2):990-4.
Kirkton et al., Engineering biosynthetic excitable tissues from unexcitable cells for electrophysiological and cell therapy studies. Nat Commun. 2011;2:300. doi: 10.1038/ncomms1302.
Klapoetke et al., Independent optical excitation of distinct neural populations. Nat Methods. Mar. 2014;11(3):338-46. doi: 10.1038/nmeth.2836. Epub Feb. 9, 2014.
Kleinlogel et al., A gene-fusion strategy for stoichiometric and co-localized expression of light-gated membrane proteins. Nat Methods. Nov. 6, 2011;8(12):1083-8. doi: 10.1038/nmeth.1766.
Knöpfel et al., Toward the second generation of optogenetic tools. J Neurosci. Nov. 10, 2010;30(45):14998-5004.
Kochendoerfer et al., How color visual pigments are tuned. Trends Biochem Sci. Aug. 1999;24(8):300-5.
Kolodner et al., Electric-field-induced Schiff-base deprotonation in D85N mutant bacteriorhodopsin. Proc Natl Acad Sci U S A. Oct. 15, 1996;93(21):11618-21.
Kralj et al., Electrical spiking in *Escherichia coli* probed with a fluorescent voltage-indicating protein. Science. Jul. 15, 2011;333(6040):345-8.
Kralj et al., Optical recording of action potentials in mammalian neurons using a microbial rhodopsin. Nat Methods. Nov. 27, 2012;9(1):90-5. doi: 10.1038/nmeth.1782.
Kramer et al., New photochemical tools for controlling neuronal activity. Curr Opin Neurobiol. Oct. 2009;19(5):544-52. doi: 10.1016/j.conb.2009.09.004. Epub Oct. 12, 2009.
Krauthamer et al., Action potential-induced fluorescence changes resolved with an optical fiber carrying excitation light. J Fluoresc. Dec. 1991;1(4):207-13.
Krylova et al., A versatile, bar-coded nuclear marker/reporter for live cell fluorescent and multiplexed high content imaging. PLoS One. May 14, 2013;8(5):e63286. doi: 10.1371/journal.pone.0063286. Print 2013.
Kuner et al., A genetically encoded ratiometric indicator for chloride: capturing chloride transients in cultured hippocampal neurons. Neuron. Sep. 2000;27(3):447-59.
Lam et al., Improving FRET dynamic range with bright green and red fluorescent proteins. Nat Methods. Oct. 2012;9(10):1005-12. doi: 10.1038/nmeth.2171. Epub Sep. 9, 2012.

Lanyi, Bacteriorhodopsin. Annu Rev Physiol. 2004;66:665-88.
Lanyi, Proton translocation mechanism and energetics in the light-driven pump bacteriorhodopsin. Biochim Biophys Acta. Dec. 7, 1993;1183(2):241-61.
Lenz et al., First steps of retinal photoisomerization in proteorhodopsin. Biophys J. Jul. 1, 2006;91(1):255-62.
Liang et al., Patterned Photostimulation with Digital Micromirror Devices to Investigate Dendritic Integration Across Branch Points. J Vis Exp. 2011;49:e2003. Video Article.
Liem et al., The patch clamp technique. Neurosurgery. Feb. 1995;36(2):382-92.
Lin et al., Brain tumor demarcation using optical spectroscopy; an in vitro study. J Biomed Opt. Apr. 2000;5(2):214-20.
Lin et al., Characterization of engineered channelrhodopsin variants with improved properties and kinetics. Biophys J. Mar. 4, 2009;96(5):1803-14. doi: 10.1016/j.bpj.2008.11.034.
Lundby et al., Engineering of a genetically encodable fluorescent voltage sensor exploiting fast Ci-VSP voltage-sensing movements. PLoS One. Jun. 25, 2008;3(6):e2514. doi: 10.1371/journal.pone.0002514.
Ma et al., Role of ER export signals in controlling surface potassium channel numbers. Science. Jan. 12, 2001;291(5502):316-9.
MacKinnon et al., Target Identification by Diazirine Photo-Cross-linking and Click Chemistry. Curr Protoc Chem Biol. Dec. 2009;1:55-73.
MacLaurin et al., Mechanism of voltage-sensitive fluorescence in a microbial rhodopsin. Proc Natl Acad Sci U S A. Apr. 9, 2013;110(15):5939-44. doi: 10.1073/pnas.1215595110. Epub Mar. 25, 2013.
Man et al., Diversification and spectral tuning in marine proteorhodopsins. EMBO J. Apr. 15, 2003;22(8):1725-31.
Martinac et al., Ion channels in microbes. Physiol Rev. Oct. 2008;88(4):1449-90.
Maruyama et al., Detecting cells using non-negative matrix factorization on calcium imaging data. Neural Netw. Jul. 2014;55:11-9. doi: 10.1016/j.neunet.2014.03.007. Epub Mar. 24, 2014.
Marvin et al., An optimized fluorescent probe for visualizing glutamate neurotransmission. Nat Methods. Feb. 2013;10(2):162-70. doi: 10.1038/nmeth.2333. Epub Jan. 13, 2013.
Mattis et al., Principles for applying optogenetic tools derived from direct comparative analysis of microbial opsins. Nat Methods. Dec. 18, 2011;9(2):159-72. doi: 10.1038/nmeth.1808.
Melkonian et al., A light and electron microscopic study of Scherffelia dubia, a new member of the scaly green flagellates (*Prasinophyceae*). Nord J Bot. 1986;6(2):235-256.
Miller et al., Optically monitoring voltage in neurons by photo-induced electron transfer through molecular wires. Proc Natl Acad Sci U S A. Feb. 7, 2012;109(6):2114-9. doi: 10.1073/pnas.1120694109. Epub Jan. 24, 2012.
Mogi et al., Aspartic acid substitutions affect proton translocation by bacteriorhodopsin. Proc Natl Acad Sci U S A. Jun. 1988;85(12):4148-52.
Molokanova et al., Bright future of optical assays for ion channel drug discovery. Drug Discov Today. Jan. 2008;13(1-2):14-22.
Muga et al., Membrane interaction and conformational properties of the putative fusion peptide of PH-30, a protein active in sperm-egg fusion. Biochemistry. Apr. 19, 1994;33(15):4444-8.
Mukamel et al., Automated analysis of cellular signals from large-scale calcium imaging data. Neuron. Sep. 24, 2009;63(6):747-60. doi: 10.1016/j.neuron.2009.08.009.
Murata et al., Phosphoinositide phosphatase activity coupled to an intrinsic voltage sensor. Nature. Jun. 30, 2005;435(7046):1239-43. Epub May 18, 2005.
Mutoh et al., Genetically engineered fluorescent voltage reporters. ACS Chem Neurosci. Aug. 15, 2012;3(8):585-92. doi: 10.1021/cn300041b. Epub Jun. 6, 2012.
Mutoh et al., Spectrally-resolved response properties of the three most advanced FRET based fluorescent protein voltage probes. PLoS One. 2009;4(2):e4555.
Nagel et al., Light activation of channelrhodopsin-2 in excitable cells of Caenorhabditis elegans triggers rapid behavioral responses. Curr Biol. Dec. 20, 2005;15(24):2279-84.

(56) References Cited

OTHER PUBLICATIONS

Neutze et al., Bacteriorhodopsin: a high-resolution structural view of vectorial proton transport. Biochim Biophys Acta. Oct. 11, 2002;1565(2):144-67.
Oldach et al., Genetically encoded fluorescent biosensors for live-cell visualization of protein phosphorylation. Chem Biol. Feb. 20, 2014;21(2):186-97. doi: 10.1016/j.chembiol.2013.12.012. Epub Jan. 30, 2014.
Park et al., Screening fluorescent voltage indicators with spontaneously spiking HEK cells. PLoS One. Dec. 31, 2013;8(12):e85221. doi: 10.1371/journal.pone.0085221. eCollection 2013.
Peron et al., From cudgel to scalpel: toward precise neural control with optogenetics. Nat Methods. Jan. 2011;8(1):30-4. doi: 10.1038/nmeth.f.325. Epub Dec. 20, 2010.
Perron et al., Second and third generation voltage-sensitive fluorescent proteins for monitoring membrane potential. Front Mol Neurosci. Jun. 22, 2009;2:5. doi: 10.3389/neuro.02.005.2009. eCollection 2009.
Popovic et al., The spatio-temporal characteristics of action potential initiation in layer 5 pyramidal neurons: a voltage imaging study. J Physiol. Sep. 1, 2011;589(Pt 17):4167-87. doi: 10.1113/jphysiol.2011.209015. Epub Jun. 13, 2011.
Przybylo et al., Fluorescence techniques for determination of the membrane potentials in high throughput screening. J Fluoresc. Nov. 2010;20(6):1139-57. doi: 10.1007/s10895-010-0665-6.
Pucihar et al., Measuring the induced membrane voltage with Di-8-ANEPPS. J Vis Exp. Nov. 19, 2009;(33). pii: 1659. doi: 10.3791/1659. Video Article.
Rousso et al., pKa of the protonated Schiff base and aspartic 85 in the bacteriorhodopsin binding site is controlled by a specific geometry between the two residues. Biochemistry. Sep. 19, 1995;34(37):12059-65.
Sakai et al., Design and characterization of a DNA-encoded, voltage-sensitive fluorescent protein. Eur J Neurosci. Jun. 2001;13(12):2314-8.
San Martin et al., Imaging mitochondrial flux in single cells with a FRET sensor for pyruvate.PLoS One. Jan. 21, 2014;9(1):e85780. doi: 10.1371/journal.pone.0085780. eCollection 2014.
Scanziani et al., Electrophysiology in the age of light. Nature. Oct. 15, 2009;461(7266):930-9. doi: 10.1038/nature08540.
Schoenenberger et al., Optimizing the spatial resolution of Channelrhodopsin-2 activation. Brain Cell Biol. Aug. 2008;36(1-4):119-27. doi: 10.1007/s11068-008-9025-8. Epub Jul. 25, 2008.
Shaner et al., A guide to choosing fluorescent proteins. Nat Methods. Dec. 2005;2(12):905-9.
Sheves et al., Controlling the pKa of the bacteriorhodopsin Schiff base by use of artificial retinal analogues. Proc Natl Acad Sci U S A. May 1986;83(10):3262-6.
Siegel et al., A genetically encoded optical probe of membrane voltage. Neuron. Oct. 1997;19(4):735-41.
Sineshchekov et al., Light-induced intramolecular charge movements in microbial rhodopsins in intact *E. coli* cells. Photochem Photobiol Sci. Jun. 2004;3(6):548-54. Epub Mar. 18, 2004.
Sjulson et al., Rational optimization and imaging in vivo of a genetically encoded optical voltage reporter. J Neurosci. May 21, 2008;28(21):5582-93.
Son et al., Conversion of mouse and human fibroblasts into functional spinal motor neurons. Cell Stem Cell. Sep. 2, 2011;9(3):205-18. doi: 10.1016/j.stem.2011.07.014.
Soppa et al., Bacteriorhodopsin mutants of *Halobacterium* sp. GRB. II. Characterization of mutants. J Biol Chem. Aug. 5, 1989;264(22):13049-56.
St-Pierre et al., High-fidelity optical reporting of neuronal electrical activity with an ultrafast fluorescent voltage sensor. Nat Neurosci. Jun. 2014;17(6):884-9. doi: 10.1038/nn.3709. Epub Apr. 22, 2014.
Stuart et al., Active propagation of somatic action potentials into neocortical pyramidal cell dendrites. Nature. Jan. 6, 1994;367(6458):69-72.
Subramaniam et al., Aspartic acid 85 in bacteriorhodopsin functions both as proton acceptor and negative counterion to the Schiff base. J Biol Chem. Dec. 25, 1992;267(36):25730-3.
Subramaniam et al., Protonation state of Asp (Glu)-85 regulates the purple-to-blue transition in bacteriorhodopsin mutants Arg-82----Ala and Asp-85----Glu: the blue form is inactive in proton translocation. Proc Natl Acad Sci U S A. Feb. 1990;87(3):1013-7.
Takahashi et al., Light-addressed single-neuron stimulation in dissociated neuronal cultures with sparse expression of ChR2. Biosystems. Feb. 2012;107(2):106-12. doi: 10.1016/j.biosystems.2011.10.002. Epub Oct. 14, 2011.
Tantama et al., Imaging energy status in live cells with a fluorescent biosensor of the intracellular ATP-to-ADP ratio. Nat Commun. 2013;4:2550. doi: 10.1038/ncomms3550.
Tateno et al., The novel ion pump rhodopsins from Haloarcula form a family independent from both the bacteriorhodopsin and archaerhodopsin families/tribes. Arch Biochem Biophys. Nov. 15, 1994;315(1):127-32.
Thevenin et al., A novel photoactivatable cross-linker for the functionally-directed region-specific fluorescent labeling of proteins. Eur J Biochem. Jun. 1, 1992;206(2):471-7.
Tsuda et al., Probing the function of neuronal populations: combining micromirror-based optogenetic photostimulation with voltage-sensitive dye imaging. Neurosci Res. Jan. 2013;75(1):76-81. doi: 10.1016/j.neures.2012.11.006. Epub Dec. 17, 2012.
Venkatachalam et al., Flash memory: photochemical imprinting of neuronal action potentials onto a microbial rhodopsin. J Am Chem Soc. Feb. 12, 2014;136(6):2529-37. doi: 10.1021/ja411338t. Epub Jan. 27, 2014.
Verburg et al., Mitochondrial membrane potential in axons increases with local nerve growth factor or semaphorin signaling. J Neurosci. Aug. 13, 2008;28(33):8306-15.
Vogt et al., Combining membrane potential imaging with L-glutamate or GABA photorelease. PLoS One. 2011;6(10):e24911. doi: 10.1371/journal.pone.0024911. Epub Oct. 11, 2011.
Wachter., The family of GFP-like proteins: structure, function, photophysics and biosensor applications. Introduction and perspective. Photochem Photobiol. Mar.-Apr. 2006;82(2):339-44.
Wang et al., Laser-evoked synaptic transmission in cultured hippocampal neurons expressing channelrhodopsin-2 delivered by adeno-associated virus. J Neurosci Methods. Oct. 15, 2009;183(2):165-75. doi: 10.1016/j.jneumeth.2009.06.024. Epub Jun. 26, 2009.
Wang et al., Non-viral gene delivery methods. Curr Pharm Biotechnol. Jan. 2013;14(1):46-60.
Wardill et al., A neuron-based screening platform for optimizing genetically-encoded calcium indicators. PLoS One. Oct. 14, 2013;8(10):e77728. doi: 10.1371/journal.pone.0077728. eCollection 2013.
Waschuk et al., Leptosphaeria rhodopsin: bacteriorhodopsin-like proton pump from a eukaryote. Proc Natl Acad Sci U S A. May 10, 2005;102(19):6879-83. Epub Apr. 28, 2005.
White, Membrane fusion. Science. Nov. 6, 1992;258(5084):917-24.
White, Viral and cellular membrane fusion proteins. Annu Rev Physiol. 1990;52:675-97.
Williams et al., Computational optogenetics: empirically-derived voltage- and light-sensitive channelrhodopsin-2 model. PLoS Comput Biol. 2013;9(9):e1003220. doi: 10.1371/journal.pcbi.1003220. Epub Sep. 12, 2013.
Wu et al., Improved orange and red $Ca^{2+}$ indicators and photophysical considerations for optogenetic applications. ACS Chem Neurosci. Jun. 19, 2013;4(6):963-72. doi: 10.1021/cn400012b. Epub Mar. 19, 2013.
Yan et al., Synthesis and characterization of a photocleavable cross-linker and its application on tunable surface modification and protein photodelivery. Bioconjug Chem. Sep.-Oct. 2004;15(5):1030-6.
Yan et al., Palette of fluorinated voltage-sensitive hemicyanine dyes. Proc Natl Acad Sci U S A. Dec. 11, 2012;109(50):20443-8. doi: 10.1073/pnas.1214850109. Epub Nov. 20, 2012.
Yizhar et al., Optogenetics in neural systems. Neuron. Jul. 14, 2011;71(1):9-34. doi: 10.1016/j.neuron.2011.06.004.

(56) References Cited

OTHER PUBLICATIONS

Zhao et al., An expanded palette of genetically encoded $Ca^{2+}$ indicators. Science. Sep. 30, 2011;333(6051):1888-91. doi: 10.1126/science.1208592. Epub Sep. 8, 2011.
Zhao et al., Molecular evolution by staggered extension process (StEP) in vitro recombination. Nat Biotechnol. Mar. 1998;16(3):258-61.
U.S. Appl. No. 15/783,886, filed Oct. 13, 2017, Cohen et al.
U.S. Appl. No. 15/645,426, filed Jul. 10, 2017, Cohen et al.
U.S. Appl. No. 14/359,387, filed May 20, 2014, Cohen et al.
U.S. Appl. No. 13/818,432, filed May 13, 2013, Cohen et al.
U.S. Appl. No. 14/739,908, filed Jun. 15, 2015, Cohen et al.
U.S. Appl. No. 14/742,648, filed Jun. 17, 2015, Cohen et al.
U.S. Appl. No. 14/303,178, filed Jun. 12, 2014, Cohen et al.
U.S. Appl. No. 14/942,992, filed Nov. 16, 2015, Cohen et al.
U.S. Appl. No. 14/995,716, filed Jan. 14, 2016, Cohen et al.

* cited by examiner

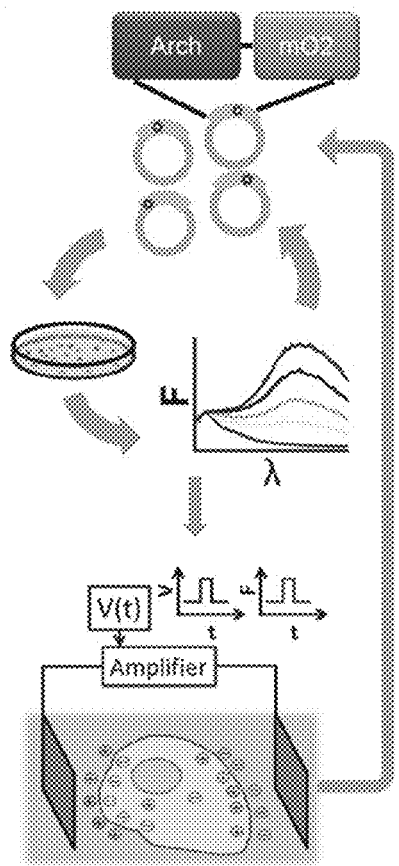
Figure 1A
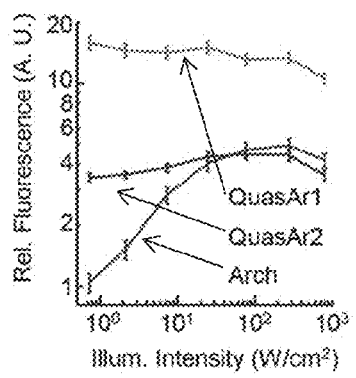 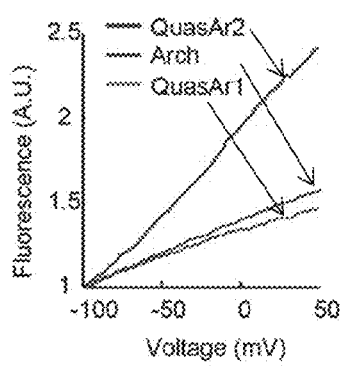 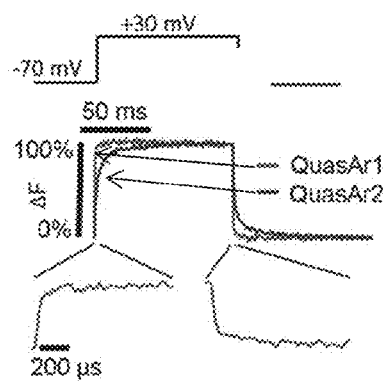
Figure 1B  Figure 1C  Figure 1D

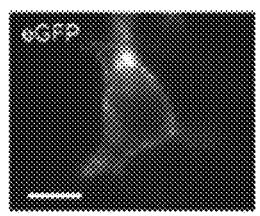
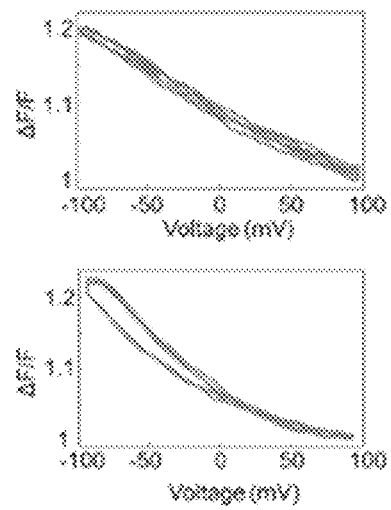
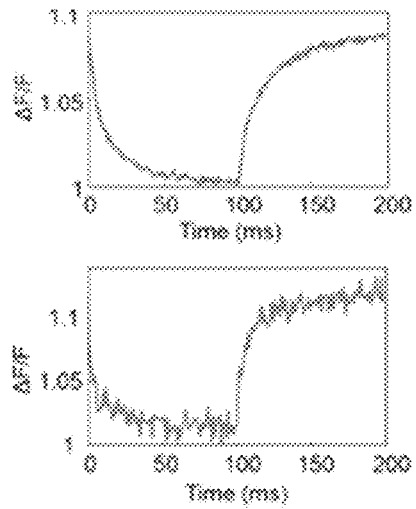
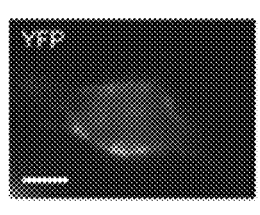
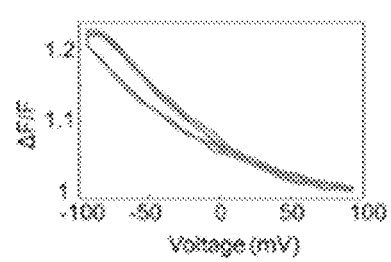
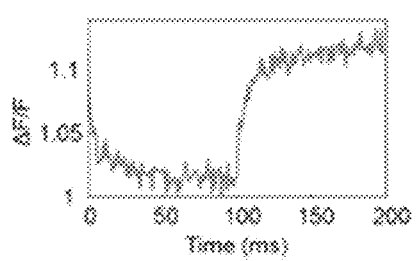
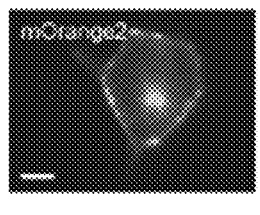
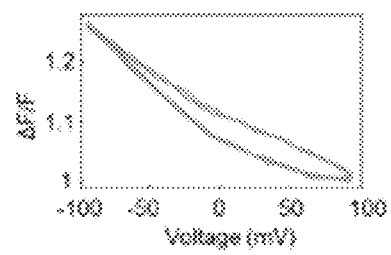
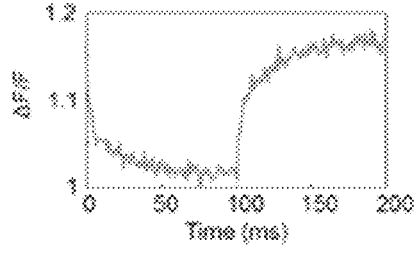
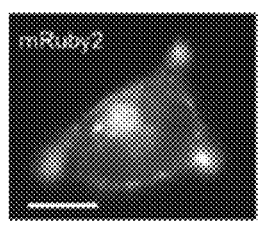
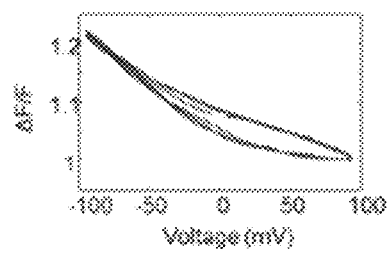
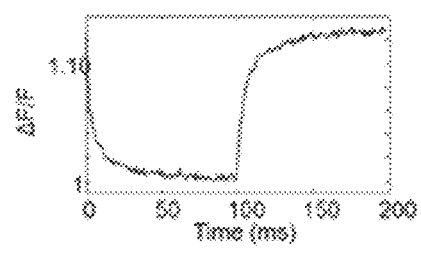
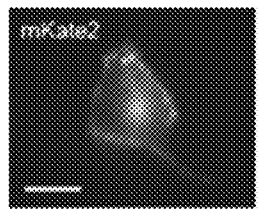
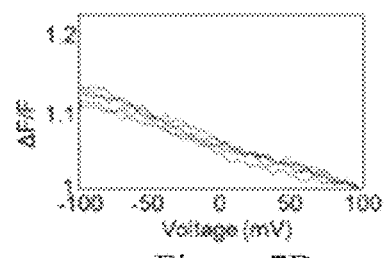
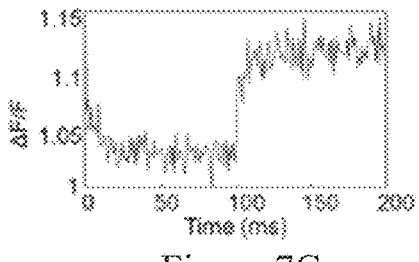
Figure 7A      Figure 7B      Figure 7C

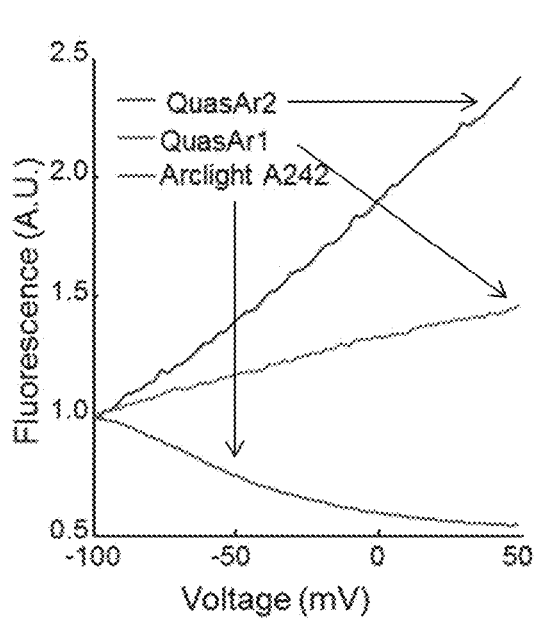
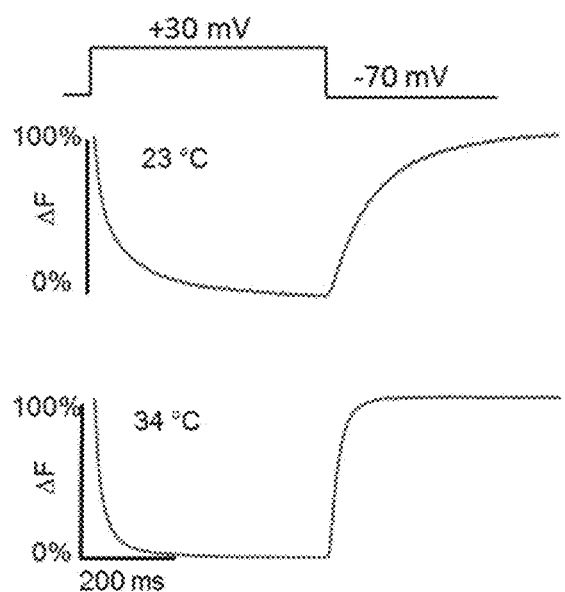
Figure 9A
Figure 9B
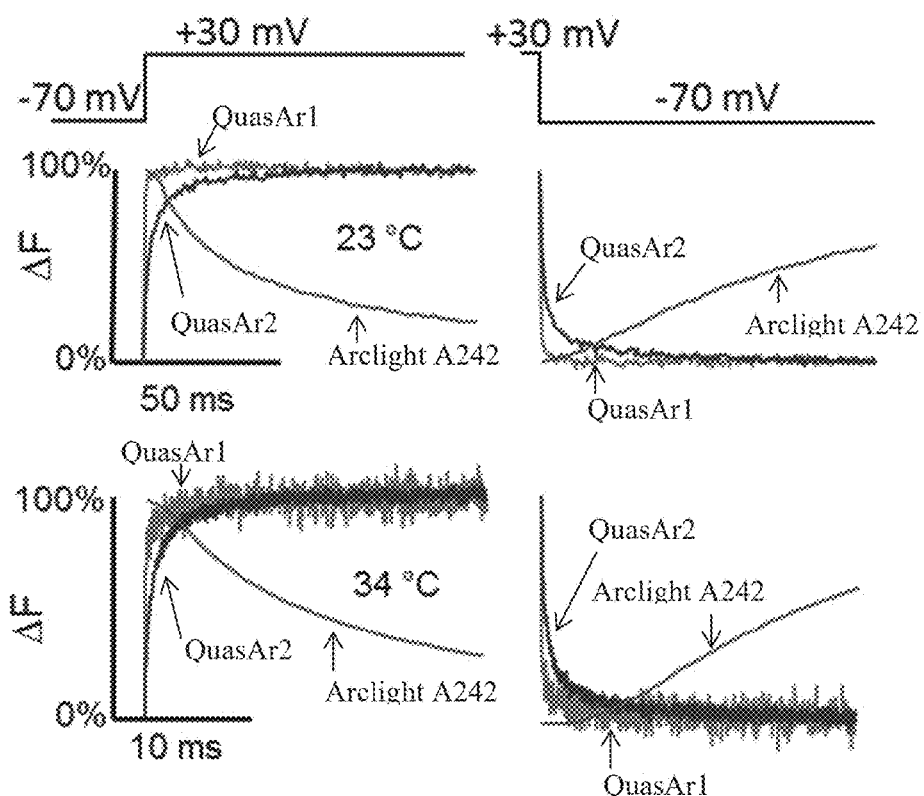
Figure 9C

SEQUENCE LISTING

```
<160> NUMBER OF SEQ ID NOS: 33

<210> SEQ ID NO 1
<211> LENGTH: 258
<212> TYPE: PRT
<213> ORGANISM: Halobacterium sodomense

<400> SEQUENCE: 1

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
```

```
                165                 170                 175
Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp

<210> SEQ ID NO 2
<211> LENGTH: 258
<212> TYPE: PRT
<213> ORGANISM: Artificial Sequence
<220> FEATURE:
<223> OTHER INFORMATION: Synthetic Polypeptide

<400> SEQUENCE: 2

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Ser Gly Ile Ala Ser
    50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala His Trp
                85                  90                  95

Leu Phe Thr Thr Pro Leu Leu Leu His Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp
```

-continued

<210> SEQ ID NO 3
<211> LENGTH: 258
<212> TYPE: PRT
<213> ORGANISM: Artificial Sequence
<220> FEATURE:
<223> OTHER INFORMATION: Synthetic Polypeptide

<400> SEQUENCE: 3

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Ser Gly Ile Ala Ser
    50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala Gln Trp
                85                  90                  95

Leu Phe Thr Thr Pro Leu Leu Leu Leu His Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp

<210> SEQ ID NO 4
<211> LENGTH: 777
<212> TYPE: DNA
<213> ORGANISM: Halobacterium sodomense

<400> SEQUENCE: 4
atggacccca tcgctctgca ggctggttac gacctgctgg gtgacggcag acctgaaact    60
ctgtggctgg gcatcggcac tctgctgatg ctgattggaa ccttctactt tctggtccgc   120
ggatggggag tcaccgataa ggatgcccgg gaatattacg ctgtgactat cctggtgccc   180
ggaatcgcat ccgccgcata tctgtctatg ttctttggta tcgggcttac tgaggtgacc   240
gtcgggggcg aaatgttgga tatctattat gccaggtacg ccgactggct gtttaccacc   300
ccacttctgc tgctggatct ggcccttctc gctaaggtgg atcgggtgac catcggcacc   360

```
ctggtgggtg tggacgccct gatgatcgtc actggcctca tcggagcctt gagccacacg    420
gccatagcca gatacagttg gtggttgttc tctacaattt gcatgatagt ggtgctctat    480
tttctggcta catccctgcg atctgctgca aaggagcggg gccccgaggt ggcatctacc    540
tttaacaccc tgacagctct ggtcttggtg ctgtggaccg cttaccctat cctgtggatc    600
ataggcactg agggcgctgg cgtggtgggc ctgggcatcg aaactctgct gtttatggtg    660
ttggacgtga ctgccaaggt cggctttggc tttatcctgt tgagatcccg ggctattctg    720
ggcgacaccg aggcaccaga acccagtgcc ggtgccgatg tcagtgccgc cgactaa      777
```

```
<210> SEQ ID NO 5
<211> LENGTH: 777
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t

<400> SEQUENCE: 5
```

```
atggaccca tcgctctgca ggctggttac gacctgctgg gtgacggcag acctgaaact    60
ctgtggctgg gcatcggcac tctgctgatg ctgattggaa ccttctactt tctggtccgc    120
ggatggggag tcaccgataa ggatgcccgg gaatattacg ctgtgactat cctggtgtcn    180
ggaatcgcat ccgccgcata tctgtctatg ttctttggta tcgggcttac tgaggtgtcn    240 gtcggggggcg aaatgttgga tatctattat gccaggtacg cccaytggct gtttaccacc    300
ccacttctgc tgctgcayct ggcccttctc gctaaggtgg atcgggtgac catcggcacc    360
ctggtgggtg tggacgccct gatgatcgtc actggcctca tcggagcctt gagccacacg    420
gccatagcca gatacagttg gtggttgttc tctacaattt gcatgatagt ggtgctctat    480
gtnctggcta catccctgcg atctgctgca aaggagcggg gccccgaggt ggcatctacc    540
tttaacaccc tgacagctct ggtcttggtg ctgtggaccg cttaccctat cctgtggatc    600
ataggcactg agggcgctgg cgtggtgggc ctgggcatcg aaactctgct gtttatggtg    660
ttggacgtga ctgccaaggt cggctttggc tttatcctgt tgagatcccg ggctattctg    720
ggcgacaccg aggcaccaga acccagtgcc ggtgccgatg tcagtgccgc cgactaa      777
```

```
<210> SEQ ID NO 6
<211> LENGTH: 777
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
```

```
<221> NAME/KEY: misc_feature
<222> LOCATION: (285)..(285)
<223> OTHER INFORMATION: n is g or a
<220> FEATURE:
<221> NAME/KEY: misc_feature
<222> LOCATION: (483)..(483)
<223> OTHER INFORMATION: n is a, c, g, or t

<400> SEQUENCE: 6
atggacccca tcgctctgca ggctggttac gacctgctgg gtgacggcag acctgaaact    60
ctgtggctgg gcatcggcac tctgctgatg ctgattggaa ccttctactt tctggtccgc   120
ggatggggag tcaccgataa ggatgcccgg gaatattacg ctgtgactat cctggtgtcn   180
ggaatcgcat ccgccgcata tctgtctatg ttctttggta tcgggcttac tgaggtgtcn   240
gtcgggggcg aaatgttgga tatctattat gccaggtacg cccantggct gtttaccacc   300
ccacttctgc tgctgcayct ggcccttctc gctaaggtgg atcgggtgac catcggcacc   360
ctggtgggtg tggacgccct gatgatcgtc actggcctca tcggagcctt gagccacacg   420
gccatagcca gatacagttg gtggttgttc tctacaattt gcatgatagt ggtgctctat   480
gtnctggcta catccctgcg atctgctgca aggagcggg ccccgaggt ggcatctacc    540 tttaacaccc tgacagctct ggtcttggtg ctgtggaccg cttaccctat cctgtggatc   600
ataggcactg agggcgctgg cgtggtgggc ctgggcatcg aaactctgct gtttatggtg   660
ttggacgtga ctgccaaggt cggctttggc tttatcctgt tgagatcccg ggctattctg   720
ggcgacaccg aggcaccaga acccagtgcc ggtgccgatg tcagtgccgc cgactaa     777

<210> SEQ ID NO 7
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 7

Ser Arg Ile Thr Ser Glu Gly Glu Tyr Ile Pro Leu Asp Gln Ile Asp
1               5                   10                  15

Ile Asn Val Gly Gly
            20

<210> SEQ ID NO 8
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 8

Phe Cys Tyr Glu Asn Glu
1               5

<210> SEQ ID NO 9
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 9
agtagaatca aagcgaagg cgagtacatc cccctggatc aaatagacat aaatgtaggt    60
gga                                                                63
```

```
<210> SEQ ID NO 10
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 10
ttttgttatg agaatga                                                    17

<210> SEQ ID NO 11
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 11

Arg Tyr Xaa Asp Glu
1               5

<210> SEQ ID NO 12
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 12
cgactctaga atggacccca tcgctctgca ggctggttac gacctgctgg gtgacggc       58

<210> SEQ ID NO 13
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 13
tgctactacc ggtcggggct cggggggcctc                                     30

<210> SEQ ID NO 14
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 14
gaggcccccg agccccgacc ggtagtagca atggtgagca agggcgagga g              51

<210> SEQ ID NO 15
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 15
gatgaagctt ttacttgtac agctcgtcca tgccg                                35

<210> SEQ ID NO 16
```

```
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 16
ctattatgcc aggtacgcch vstggctgtt taccacccca c                41

<210> SEQ ID NO 17
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: n is a, c, g, or t

<400> SEQUENCE: 17
ccccacttct gctgctgnrc ctggcccttc tcgctaa                    37

<210> SEQ ID NO 18
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 18
attatgccag gtacgccaat tggctgttta ccacc                      35

<210> SEQ ID NO 19
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 19
ctattatgcc aggtacgcct gttggctgtt taccacccca c                41

<210> SEQ ID NO 20
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 20
ctattatgcc aggtacgccc agtggctgtt taccacccca c                41

<210> SEQ ID NO 21
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 21
ccccacttct gctgctgtgc ctggcccttc tcgctaa                    37

<210> SEQ ID NO 22
<211> LENGTH: 37
<212> TYPE: DNA
<213> ORGANISM: Artificial Sequence
```

```
<220> FEATURE:
<223> OTHER INFORMATION: Synthetic Polynucleotide

<400> SEQUENCE: 22
ccccacttct gctgctggag ctggcccttc tcgctaa                              37

<210> SEQ ID NO 23
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 23
cgacggatcc accatggacc ccatcgctct gcaggc                              36

<210> SEQ ID NO 24
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 24
gatgtctaga ttattcattc tcataacaaa acttgtacag ctcgtccatg ccg           53

<210> SEQ ID NO 25
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 25
tgggatccac catggtaagt atcgctctgc aggctggtta c                        41

<210> SEQ ID NO 26
<211> LENGTH: 61
<212> TYPE: DNA
<213> ORGANISM: Artificial Sequence
<220> FEATURE:
<223> OTHER INFORMATION: Synthetic Polynucleotide

<400> SEQUENCE: 26
atccaggggg atgtactcgc cttcgcttgt gattctactc ttgtacagct cgtccatgcc    60
g                                                                    61

<210> SEQ ID NO 27
<211> LENGTH: 79
<212> TYPE: DNA
<213> ORGANISM: Artificial Sequence
<220> FEATURE:
<223> OTHER INFORMATION: Synthetic Polynucleotide

<400> SEQUENCE: 27
gatggaattc ttatacttca ttctcataac aaaatccacc tacatttatg tctatttgat    60 ccaggggat gtactcgcc                                                  79

<210> SEQ ID NO 28
<211> LENGTH: 777
<212> TYPE: DNA
<213> ORGANISM: Artificial Sequence
<220> FEATURE:
<223> OTHER INFORMATION: Synthetic Polynucleotide
<220> FEATURE:
```

<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (240)..(240)
<223> OTHER INFORMATION: n is t or c
<220> FEATURE:
<221> NAME/KEY: misc_feature
<222> LOCATION: (483)..(483)
<223> OTHER INFORMATION: n is a, c, g, or t

<400> SEQUENCE: 28

```
atggacccca tcgctctgca ggctggttac gacctgctgg gtgacggcag acctgaaact      60
ctgtggctgg gcatcggcac tctgctgatg ctgattggaa ccttctactt tctggtccgc     120
ggatggggag tcaccgataa ggatgcccgg gaatattacg ctgtgactat cctggtgtcn     180
ggaatcgcat ccgccgcata tctgtctatg ttctttggta tcgggcttac tgaggtgagn     240
gtcggggcg  aaatgttgga tatctattat gccaggtacg cccaytggct gtttaccacc     300
ccacttctgc tgctgcayct ggcccttctc gctaaggtgg atcgggtgac catcggcacc     360
ctggtgggtg tggacgccct gatgatcgtc actggcctca tcggagcctt gagccacacg     420
gccatagcca gatacagttg gtggttgttc tctacaattt gcatgatagt ggtgctctat     480
gtnctggcta catccctgcg atctgctgca aaggagcggg ccccgaggt ggcatctacc     540
tttaacaccc tgacagctct ggtcttggtg ctgtggaccg cttaccctat cctgtggatc     600
ataggcactg agggcgctgg cgtggtgggc ctgggcatcg aaactctgct gtttatggtg     660
ttggacgtga ctgccaaggt cggctttggc tttatcctgt tgagatcccg ggctattctg     720
ggcgacaccg aggcaccaga acccagtgcc ggtgccgatg tcagtgccgc cgactaa       777
```

<210> SEQ ID NO 29
<211> LENGTH: 777
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (180)..(180)
<223> OTHER INFORMATION: n is t or c
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t

<400> SEQUENCE: 29

```
atggacccca tcgctctgca ggctggttac gacctgctgg gtgacggcag acctgaaact      60
ctgtggctgg gcatcggcac tctgctgatg ctgattggaa ccttctactt tctggtccgc     120
ggatggggag tcaccgataa ggatgcccgg gaatattacg ctgtgactat cctggtgagn     180
ggaatcgcat ccgccgcata tctgtctatg ttctttggta tcgggcttac tgaggtgtcn     240
gtcggggcg  aaatgttgga tatctattat gccaggtacg cccaytggct gtttaccacc     300
ccacttctgc tgctgcayct ggcccttctc gctaaggtgg atcgggtgac catcggcacc     360
ctggtgggtg tggacgccct gatgatcgtc actggcctca tcggagcctt gagccacacg     420
gccatagcca gatacagttg gtggttgttc tctacaattt gcatgatagt ggtgctctat     480
gtnctggcta catccctgcg atctgctgca aaggagcggg ccccgaggt ggcatctacc     540
```
tttaacaccc tgacagctct ggtcttggtg ctgtggaccg cttaccctat cctgtggatc    600
ataggcactg agggcgctgg cgtggtgggc ctgggcatcg aaactctgct gtttatggtg    660
ttggacgtga ctgccaaggt cggctttggc tttatcctgt tgagatcccg ggctattctg    720
ggcgacaccg aggcaccaga acccagtgcc ggtgccgatg tcagtgccgc cgactaa      777

<210> SEQ ID NO 30
<211> LENGTH: 777
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (180)..(180)
<223> OTHER INFORMATION: n is t or c
<220> FEATURE:
<221> NAME/KEY: misc_feature
<222> LOCATION: (240)..(240)
<223> OTHER INFORMATION: n is t or c
<220> FEATURE:
<221> NAME/KEY: misc_feature
<222> LOCATION: (483)..(483)
<223> OTHER INFORMATION: n is a, c, g, or t

<400> SEQUENCE: 30
atggacccca tcgctctgca ggctggttac gacctgctgg gtgacggcag acctgaaact     60
ctgtggctgg gcatcggcac tctgctgatg ctgattggaa ccttctactt tctggtccgc    120
ggatggggag tcaccgataa ggatgcccgg gaatattacg ctgtgactat cctggtgagn    180
ggaatcgcat ccgccgcata tctgtctatg ttctttggta tcgggcttac tgaggtgagn    240
gtcgggggcg aaatgttgga tatctattat gccaggtacg cccaytggct gtttaccacc    300
ccacttctgc tgctgcayct ggcccttctc gctaaggtgg atcgggtgac catcggcacc    360
ctggtgggtg tggacgccct gatgatcgtc actggcctca tcggagcctt gagccacacg    420
gccatagcca gatacagttg gtggttgttc tctacaattt gcatgatagt ggtgctctat    480
gtnctggcta catccctgcg atctgctgca aaggagcggg ccccgaggt ggcatctacc    540 tttaacaccc tgacagctct ggtcttggtg ctgtggaccg cttaccctat cctgtggatc    600
ataggcactg agggcgctgg cgtggtgggc ctgggcatcg aaactctgct gtttatggtg    660
ttggacgtga ctgccaaggt cggctttggc tttatcctgt tgagatcccg ggctattctg    720
ggcgacaccg aggcaccaga acccagtgcc ggtgccgatg tcagtgccgc cgactaa      777

<210> SEQ ID NO 31
<211> LENGTH: 777
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (240)..(240)
<223> OTHER INFORMATION: n is t or c
<220> FEATURE:
<221> NAME/KEY: misc_feature
<222> LOCATION: (285)..(285)
<223> OTHER INFORMATION: n is g or a
<220> FEATURE:
<221> NAME/KEY: misc_feature
<222> LOCATION: (483)..(483)

<223> OTHER INFORMATION: n is a, c, g, or t

<400> SEQUENCE: 31

```
atggacccca tcgctctgca ggctggttac gacctgctgg gtgacggcag acctgaaact    60
ctgtggctgg gcatcggcac tctgctgatg ctgattggaa ccttctactt tctggtccgc   120
ggatggggag tcaccgataa ggatgcccgg aatattacg ctgtgactat cctggtgtcn   180
ggaatcgcat ccgccgcata tctgtctatg ttctttggta tcgggcttac tgaggtgagn   240
gtcggggggcg aaatgttgga tatctattat gccaggtacg cccantggct gtttaccacc   300
ccacttctgc tgctgcayct ggcccttctc gctaaggtgg atcgggtgac catcggcacc   360
ctggtgggtg tggacgccct gatgatcgtc actggcctca tcggagcctt gagccacacg   420
gccatagcca gatacagttg gtggttgttc tctacaattt gcatgatagt ggtgctctat   480
gtnctggcta catccctgcg atctgctgca aaggagcggg gccccgaggt ggcatctacc   540
tttaacaccc tgacagctct ggtcttggtg ctgtggaccg cttaccctat cctgtggatc   600
ataggcactg agggcgctgg cgtggtgggc ctggcatcg aaactctgct gtttatggtg   660
ttggacgtga ctgccaaggt cggctttggc tttatcctgt tgagatcccg ggctattctg   720
ggcgacaccg aggcaccaga acccagtgcc ggtgccgatg tcagtgccgc cgactaa     777
```

<210> SEQ ID NO 32
<211> LENGTH: 777
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (180)..(180)
<223> OTHER INFORMATION: n is t or c
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (285)..(285)
<223> OTHER INFORMATION: n is g or a
<220> FEATURE:
<221> NAME/KEY: misc_feature
<222> LOCATION: (483)..(483)
<223> OTHER INFORMATION: n is a, c, g, or t

<400> SEQUENCE: 32

```
atggacccca tcgctctgca ggctggttac gacctgctgg gtgacggcag acctgaaact    60
ctgtggctgg gcatcggcac tctgctgatg ctgattggaa ccttctactt tctggtccgc   120
ggatggggag tcaccgataa ggatgcccgg aatattacg ctgtgactat cctggtgagn   180
ggaatcgcat ccgccgcata tctgtctatg ttctttggta tcgggcttac tgaggtgtcn   240
gtcggggggcg aaatgttgga tatctattat gccaggtacg cccantggct gtttaccacc   300
ccacttctgc tgctgcayct ggcccttctc gctaaggtgg atcgggtgac catcggcacc   360
ctggtgggtg tggacgccct gatgatcgtc actggcctca tcggagcctt gagccacacg   420
gccatagcca gatacagttg gtggttgttc tctacaattt gcatgatagt ggtgctctat   480
gtnctggcta catccctgcg atctgctgca aaggagcggg gccccgaggt ggcatctacc   540
tttaacaccc tgacagctct ggtcttggtg ctgtggaccg cttaccctat cctgtggatc   600
ataggcactg agggcgctgg cgtggtgggc ctggcatcg aaactctgct gtttatggtg   660
ttggacgtga ctgccaaggt cggctttggc tttatcctgt tgagatcccg ggctattctg   720
```

```
ggcgacaccg aggcaccaga acccagtgcc ggtgccgatg tcagtgccgc cgactaa      777

<210> SEQ ID NO 33
<211> LENGTH: 777
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (180)..(180)
<223> OTHER INFORMATION: n is t or c
<220> FEATURE:
<221> NAME/KEY: misc_feature
<222> LOCATION: (240)..(240)
<223> OTHER INFORMATION: n is t or c
<220> FEATURE:
<221> NAME/KEY: misc_feature
<222> LOCATION: (285)..(285)
<223> OTHER INFORMATION: n is g or a
<220> FEATURE:
<221> NAME/KEY: misc_feature
<222> LOCATION: (483)..(483)
<223> OTHER INFORMATION: n is a, c, g, or t

<400> SEQUENCE: 33
atggacccca tcgctctgca ggctggttac gacctgctgg gtgacggcag acctgaaact      60
ctgtggctgg gcatcggcac tctgctgatg ctgattggaa ccttctactt tctggtccgc     120
ggatggggag tcaccgataa ggatgcccgg gaatattacg ctgtgactat cctggtgagn     180
ggaatcgcat ccgccgcata tctgtctatg ttctttggta tcgggcttac tgaggtgagn     240 gtcggggcg aaatgttgga tatctattat gccaggtacg cccantggct gtttaccacc      300
ccacttctgc tgctgcayct ggccttctc gctaaggtgg atcgggtgac catcggcacc     360
ctggtgggtg tggacgccct gatgatcgtc actggcctca tcggagcctt gagccacacg     420
gccatagcca gatacagttg gtggttgttc tctacaattt gcatgatagt ggtgctctat     480
gtnctggcta catccctgcg atctgctgca aaggagcggg ccccgaggt ggcatctacc      540 tttaacaccc tgacagctct ggtcttggtg ctgtggaccg cttaccctat cctgtggatc     600
ataggcactg agggcgctgg cgtggtgggc ctgggcatcg aaactctgct gtttatggtg     660
ttggacgtga ctgccaaggt cggctttggc tttatcctgt tgagatcccg ggctattctg     720
ggcgacaccg aggcaccaga acccagtgcc ggtgccgatg tcagtgccgc cgactaa      777
```

OPTOGENETIC PROBES FOR MEASURING MEMBRANE POTENTIAL

RELATED APPLICATIONS

The present application is a continuation of and claims priority under 35 U.S.C. § 120 to U.S. application Ser. No. 14/742,648, filed Jun. 17, 2015, which claims priority under 35 U.S.C. § 119(e) to U.S. provisional patent application Ser. No. 62/013,775, filed Jun. 18, 2014, each of which is incorporated herein by reference.

GOVERNMENT SUPPORT

The present application is a continuation of and claims priority under 35 U.S.C. § 120 to U.S. application Ser. No. 14/742,648, filed Jun. 17, 2015, now U.S. Pat. No. 9,518,103, which claims priority under 35 U.S.C. § 119(e) to U.S. provisional patent application Ser. No. 62/013,775, filed Jun. 18, 2014, each of which is incorporated herein by reference.

BACKGROUND

Membrane-enclosed biological structures can support a voltage difference between the inside and the outside of the membrane. This voltage, also called a membrane potential, serves a variety of biological functions, including carrying information (e.g., in neurons), acting as an intermediate in the production of ATP (e.g., in bacteria and mitochondria), powering the flagellar motor (e.g., in bacteria), and controlling the transport of nutrients, toxins, and signaling molecules across the cell membrane (in bacteria and eukaryotic cells).

In spite of its fundamental biological role, membrane potential is very difficult to measure. Electrophysiology involves positioning electrodes on both sides of the membrane to record voltage directly. Electrophysiological experiments are slow to set up, can only be performed on one or a few cells at a time, cannot access deeply buried tissues (e.g., in vivo), do not work for cells that are too small (e.g. bacteria) or are enclosed in a hard cell wall (e.g. yeast), or are motile (e.g., sperm), cannot be applied to long-term measurements, and usually damage or kill the cell under study. Accordingly, novel methods for measuring membrane potential are needed.

To disentangle the complex interactions underlying neural dynamics, one would like to visualize membrane voltage across spatial scales, from single dendritic spines to large numbers of interacting neurons, while delivering spatially and temporally precise stimuli.[1,2] Optical methods for simultaneous perturbation and measurement of membrane potential could achieve this goal.[3] Genetic targeting of the stimulation and recording to genetically specified cells is useful in intact tissue where closely spaced cells often perform distinct functions. Genetic targeting in vitro is also useful for characterizing heterogeneous cultures that arise during stem cell differentiation to neurons,[4] or while studying neurons co-cultured with other cell types.

Optical stimulation has been demonstrated with glutamate uncaging,[5] photoactivated ion channel agonists[6], and microbial rhodopsin actuators.[7,8] Genetically encoded functional readouts include reporters of intracellular $Ca^{2+}$ and membrane voltage.[9-14] Voltage-sensitive dyes offer good speed, sensitivity, and spectral tuning,[15,16] but cannot be delivered to a genetically specified subset of cells and often suffer from phototoxicity.

Simultaneous optical stimulation and readout of neural activity have been implemented via several combinations of the above techniques.[17-21] However, robust genetically targeted all-optical electrophysiology has not been achieved due to limitations on the speed and sensitivity of genetically encoded voltage indicators (GEVIs), and spectral overlap between existing GEVIs and optogenetic actuators. GFP-based GEVIs experience severe optical crosstalk with even the most red-shifted channelrhodopsins, which retain ~20% activation with blue light excitation. Therefore, there remains a need for sensitive, fast, and spectrally orthogonal tools for genetically targeted simultaneous optical perturbation and measurement of membrane voltage.

SUMMARY OF THE INVENTION

Provided herein are fluorescent polypeptides which are based on the microbial rhodopsin family called Archaerhodopsin and are useful as voltage indicators. The inventive polypeptides provided herein function in eukaryotic cells such as mammalian cells, e.g., neurons and cardiomyocytes including human stem cell-derived cardiomyocytes. The inventive polypeptides localize to various cellular locations, e.g., the plasma membrane in eukaryotic cells, and show voltage-dependent fluorescence.

By optically measuring the membrane potential of cells and sub-cellular compartments, the inventive polypeptides are capable of indicating electrical dynamics with sub-millisecond temporal resolution and sub-micron spatial resolution. The inventive polypeptides have improved properties over the wild-type Archaerhodopsin such as increased brightness, increased sensitivity, higher signal-to-noise ratios, increased linearity with respect to voltage or intensity, and faster response time (increased time resolution), with speed and sensitivity being important parameters for evaluating voltage indicators. The improved polypeptides provided herein are useful as optically detectable sensors for sensing voltage across membranous structures. It was previously demonstrated that the membrane potential in a membrane containing Archaerhodopsin 3 (Arch 3) can alter the optical properties of the protein, thereby making Arch 3 a voltage sensor. The modified microbial rhodopsin, Arch 3 D95N, has a 40 ms response time and lacks photoinduced proton pumping. Although the slower response time of this construct hampers detection of membrane potential and changes thereto in neurons, the Arch 3 D95N is fast enough to indicate membrane potential and action potentials in other types of cells, for example, in cardiomyocytes and does not perturb membrane potential in the cells wherein it is used.

Through a combination of directed evolution and targeted mutagenesis, polypeptides based on the human codon-optimized sequence of Achaerhodopsin genetically encoded voltage indicators GEVIs with improved performance have been identified.

In certain embodiments, the polypeptide variants are based on Archaerhodopsin such as Archaerhodopsin 3 (Arch 3) and its homologues, including Archaerhodopsin-1, Archaerhodopsin-2, *L. Maculans* rhodopsin (Mac), Cruxrhodopsin (Crux), and green-absorbing proteorhodopsin (GPR) (see, e.g., Enami et al., *J Mol. Biol.* (2006) May 5; 358(3):675-85, Epub 2006 Mar. 3; Waschuk, S. A. et al., *Proc. Natl Acad. Sci. USA* (2005) 102: 6879-6883; Tateno, M. et al. (1994) Arch. Biochem. Biophys. 315: 127-132; Giovannoni et al. (2005) Nature 438(7064): 82-85). Arch 3 has been described in, for example, Chow, B. Y. et al., *Nature* (2010) 463:98-102, which is incorporated herein by reference in its entirety. The inventive polypeptides described herein also include polypeptides based on other archaerhopsins with mutations in locations homologous to those described herein. Other microbial rhodopsins include, but are not limited to, archaerhodopsin-1 and -2, *L. Maculans* rhodopsin (Mac), Cruxrhodopsin (Crux), and green-absorbing proteorhodopsin (GPR).

The present invention relates to variants of Archaerhodopsin, comprising at least one or two amino acid substitutions at positions corresponding to positions P60, T80, D95, D106, or F161 of the archaerhodopsin sequence of SEQ ID NO: 1, wherein the variant has at least 80% but less than 100% sequence identity with the archaerhodopsin sequence of SEQ ID NO: 1, and wherein the variant has no proton pumping activity.

The present invention also relates to polynucleotides encoding the polypeptides; nucleic acid constructs, vectors, cells comprising the polynucleotides; cells comprising the polypeptides; and methods of using the polypeptides and polynucleotides described herein.

DEFINITIONS

The inventive polypeptides are generally referred to or described as a "genetically encoded voltage indicator" (GEVI), which is used interchangeably with the phrases "voltage-indicating protein" (VIP), "optical sensor", or "optical voltage indicators", or similar phrases. As described in more detail herein, the inventive polypeptides employed yield an optical signal indicative of the voltage drop across the membrane in which it is embedded.

The terms "variant" or "mutant" means a polypeptide based on the sequence of archaerhodopsin comprising an alteration, i.e., a substitution, insertion, and/or deletion, at one or more positions of the polypeptide. A substitution means a replacement of an amino acid occupying a position with a different amino acid; a deletion means removal of an amino acid occupying a position; and an insertion means adding 1-3 amino acids adjacent to an amino acid occupying a position. Variants include those with homologous mutations in another microbial rhodopsin (e.g., another archaerhodopsin) that corresponds to the amino acid mutations specifically listed herein that is expected to have a similar effect to a substantially similar mutation in bacteriorhodopsin. One of skill in the art can easily locate a homologous residue in their desired microbial rhodopsin by performing an alignment of conserved regions of the desired microbial rhodopsin with a bacteriorhodopsin sequence using a computer program such as ClustalW. Examples of homologous mutations include the mutations made in the Examples set forth in this application. The terms variant or mutant also refers to a polynucleotide variant encoding a polypeptide variant described herein. The polynucleotide variant encompasses all forms of mutations including deletions, insertions, and point mutations in the coding sequence.

The term "polypeptide" or "polynucleotide" means a polypeptide or polynucleotide variant that is separate from its native environment, modified by humans, and is present in sufficient quantity to permit its identification or use. The polypeptide or polynucleotide is one that is not part of, or included in its native host. For example, a nucleic acid or polypeptide sequence may be naturally expressed in a cell or organism of a member of *Halobacterium sodomense* but when the sequence is not part of or included in a *Halobacterium sodomense* cell or organism, it is considered to be isolated. Thus, a polypeptide or polynucleotide sequence of an Archaerhodopsin that is present in a vector, in a heterologous cell, tissue, or organism, etc., is an isolated sequence. The term "heterologous" as used herein, means a cell, tissue or organism that is not the native cell, tissue, or organism. The polynucleotides provided herein may be DNA, RNA, semi-synthetic, synthetic origin, or any combinations thereof.

The term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA.

The term "nucleic acid construct" means a nucleic acid molecule, either single- or double-stranded, which is modified to contain segments of nucleic acids in a manner that would not otherwise exist in nature or which is synthetic. The nucleic acid construct may be part of an expression vector or may be an expression vector when the nucleic acid construct contains the control sequences required for expression of a coding sequence of the present invention.

The term "operably linked" means a configuration in which a control sequence is placed at an appropriate position relative to the coding sequence of a polynucleotide such that the control sequence directs the expression of the coding sequence.

The term "expression" includes any step involved in the production of the polypeptide variant including, but not limited to, transcription, post-transcriptional modification, translation, post-translational modification, and secretion.

The term "expression vector" means a linear or circular DNA molecule that comprises a polynucleotide encoding a variant and is operably linked to additional nucleotides that provide for its expression.

The term "homologous," as used herein, is an art-understood term that refers to nucleic acids or proteins that are highly related at the level of nucleotide or amino acid sequence. Nucleic acids or proteins that are homologous to each other are termed homologues. Homologous may refer to the degree of sequence similarity between two sequences (i.e., nucleotide sequence or amino acid). The homology percentage figures referred to herein reflect the maximal homology possible between two sequences, i.e., the percent homology when the two sequences are so aligned as to have the greatest number of matched (homologous) positions. Homology can be readily calculated by known methods such as those described in: Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. Methods commonly employed to determine homology between sequences include, but are not limited to those disclosed in Carillo, H., and Lipman, D., *SIAM J Applied Math.*, 48:1073 (1988), incorporated herein by reference. Techniques for determining homology are codified in publicly available computer programs. Exemplary computer software to determine homology between two sequences include, but are not limited to, GCG program package, Devereux, J., et al., *Nucleic Acids Research*, 12(1), 387 (1984)), BLASTP, BLASTN, and PASTA Atschul, S. F. et al., *J Molec. Biol.*, 215, 403 (1990)).

The term "identity" refers to the overall relatedness between nucleic acids (e.g. DNA and/or RNA) or between proteins. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM 120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Atschul, S. F. et al., *J. Molec. Biol.,* 215, 403 (1990)).

As used herein, the term "protein" refers to a polymer of at least two amino acids linked to one another by peptide bonds. The terms, "protein" and "polypeptides" are used interchangeably herein. Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example, linked by one or more disulfide bonds or associated by other means. A polypeptide may refer to an individual peptide or a collection of polypeptides. Polypeptides may contain L-amino acids, D-amino acids, or both and may contain any of a variety of amino acid modifications or analogs known in the art. Useful modifications include, e.g., addition of a chemical entity such as a carbohydrate group, a phosphate group, a farnesyl group, an isofarnesyl group, a fatty acid group, an amide group, a terminal acetyl group, a linker for conjugation, functionalization, or other modification (e.g., alpha amidation), etc. In certain embodiments, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide. In certain embodiments, the modifications of the peptide lead to a more biologically active peptide. In certain embodiments, polypeptides may comprise natural amino acids, non-natural amino acids (i.e., compounds that do not occur in nature but that can be incorporated into a peptide chain), synthetic amino acids, amino acid analogs, and combinations thereof. A polypeptide may be just a fragment of a naturally occurring protein. A polypeptide may be naturally occurring, recombinant, synthetic, or any combination thereof.

"Microbial rhodopsins" are a large class of proteins characterized by seven transmembrane domains and a retinilydene chromophore bound in the protein core to a lysine via a Schiff base (Beja, O., et al. *Nature* 411, 786-789 (2001)). Over 5,000 microbial rhodopsins are known, and these proteins are found in all kingdoms of life. Microbial rhodopsins serve a variety of functions for their hosts: some are light-driven proton pumps (bacteriorhodopsin, proteorhodopsins), others are light-driven ion channels (channelrhodopsins), chloride pumps (halorhodopsins), or serve in a purely photosensory capacity (sensory rhodopsins). The retinilydene chromophore imbues microbial rhodopsins with unusual optical properties. The linear and nonlinear responses of the retinal are highly sensitive to interactions with the protein host: small changes in the electrostatic environment can lead to large changes in absorption spectrum. These electro-optical couplings provide the basis for voltage sensitivity in microbial rhodopsins.

In nature, microbial rhodopsins contain a bound molecule of retinal which serves as the optically active element. These proteins will also bind and fold around many other chromophores with similar structure, and possibly preferable optical properties. Analogues of retinal with locked rings cannot undergo trans-cis isomerization, and therefore have higher fluorescence quantum yields (Brack et al. *Biophys. J.* 65, 964-972 (1993)). Analogues of retinal with electron-withdrawing substituents have a Schiff base with a lower pKa than natural retinal and therefore may be more sensitive to voltage (Sheves et al. *Proc. Nat. Acad. Sci. U.S.A.* 83, 3262-3266 (1986); Rousso, I., et al. *Biochemistry* 34, 12059-12065 (1995)). Covalent modifications to the retinal molecule may lead to voltage-indicating proteins (VIPs) with significantly improved optical properties and sensitivity to voltage.

"Archaerhodopsin 3" (Arch 3 or Ar 3) is a microbial rhodopsin that is a light-driven proton pump found in *Halobacterium sodomense* (Chow et al., *High-performance genetically targetable optical neural silencing by light-driven proton pumps. Nature* (2010) 463:98-102), capturing solar energy for its host (Ihara et al., *Evolution of the archaeal rhodopsins: evolution rate changes by gene duplication and functional differentiation. J. Mol. Biol.* (1999)

285: 163-174). Genbank number: P96787. Arch 3 is an Archaerhodopsin from *H. sodomense*, and it is known as a genetically-encoded reagent for high-performance yellow/green-light neural silencing. Gene sequence at GenBank: GU045593.1 (synthetic construct Arch 3 gene).

The term "additional fluorescent molecule" refers to fluorescent proteins other than microbial rhodopsins. Such molecules may include, e.g., green fluorescent proteins and their homologs. Fluorescent proteins that are not microbial rhodopsins are well known and commonly used, and examples can be found, e.g., in a review, The Family of GFP-Like Proteins: Structure, Function, Photophysics and Biosensor Applications. Introduction and Perspective, by Rebekka M. Wachter (Photochemistry and Photobiology Volume 82, Issue 2, pages 339-344, March 2006). Also, a review by Nathan C Shaner, Paul A Steinbach, & Roger Y Tsien, entitled A guide to choosing fluorescent proteins (Nature Methods—2, 905-909 (2005)) provides examples of additional useful fluorescent proteins.

As used herein the phrase "reduced ion pumping activity" means a decrease in the endogenous ion pumping activity of a modified microbial rhodopsin protein of at least 10% compared to the endogenous pumping activity of the natural microbial rhodopsin protein from which the modified rhodopsin is derived. The ions most commonly pumped by microbial rhodopsins are $H^+$ and $Cl^-$. In some embodiments, the ion pumping activity of a modified rhodopsin protein is at least 20% lower, at least 30%, at least 40%, at least 50%, at least 60%, at least 70%, at least 80%, at least 90%, at least 95%, or at least 99% lower than the endogenous ion pumping activity of the corresponding wild type microbial rhodopsin protein. In certain embodiments, the modified microbial rhodopsin has no detectable ion pumping activity.

As used herein, the term "endogenous ion pumping activity" refers to the movement of ions through the wild-type microbial rhodopsin protein that occurs in response to light stimuli.

As used herein, the term "wild-type", "natural", or "native" microbial rhodopsin protein refers to a rhodopsin protein (e.g., Archaerhodopsin) prepared from a microbial (e.g., bacterial, archaeal, or eukaryotic) source. Such natural microbial rhodopsin proteins, when isolated, retain characteristics (e.g., pKa, ion pumping activity, etc.) that are substantially similar to the microbial rhodopsin protein in its native environment (e.g., in a microbial cell). Some non-limiting examples of microbial rhodopsin proteins useful with the methods described herein include green-absorbing proteorhodopsin (GPR; GenBank accession number AF349983), blue-absorbing proteorhodopsin (BPR, GenBank accession number AF349981), *Natromonas pharaonis* sensory rhodopsin II (NpSRII; GenBank accession number Z35086.1), and bacteriorhodopsin (BR; the protein encoded by GenBank sequence NC_010364.1, nucleotides 1082241-1083029, wherein 1082241 is designated as 1 herein, GenBank accession number M11720.1, or as described by e.g., Beja et al., (2000). *Science* 289 (5486): 1902-1904), and archaerhodopsin (see e.g., Chow et al., *Nature* 463:98-102 (2010) and the Examples in this application).

As used herein, the term "variant", "mutant", or "modified" microbial rhodopsin protein refers to a wild-type microbial rhodopsin protein comprising at least one mutation. Mutations can be in the nucleic acid sequence (e.g., genomic or mRNA sequence), or alternatively can comprise an amino acid substitution. Such amino acid substitutions can be conserved mutations or non-conserved mutations. As well-known in the art, a "conservative substitution" of an amino acid or a "conservative substitution variant" of a polypeptide refers to an amino acid substitution which maintains: 1) the structure of the backbone of the polypeptide (e.g. a beta sheet or alpha-helical structure); 2) the charge or hydrophobicity of the amino acid; or 3) the bulkiness of the side chain. More specifically, the well-known terminologies "hydrophilic residues" relate to serine or threonine. "Hydrophobic residues" refer to leucine, isoleucine, phenylalanine, valine or alanine. "Positively charged residues" relate to lysine, arginine or histidine. "Negatively charged residues" refer to aspartic acid or glutamic acid. Residues having "bulky side chains" refer to phenylalanine, tryptophan or tyrosine. To avoid doubt as to nomenclature, the term "D97N" or similar terms specifying other specific amino acid substitutions means that the Asp (D) at position 97 of the protein sequence is substituted with Asn (N). A "conservative substitution variant" of D97N would substitute a conservative amino acid variant of Asn (N) that is not D.

The terminology "conservative amino acid substitutions" is well known in the art, which relates to substitution of a particular amino acid by one having a similar characteristic (e.g., similar charge or hydrophobicity, similar bulkiness). Examples include aspartic acid for glutamic acid, or isoleucine for leucine. A list of exemplary conservative amino acid substitutions is given in the Table 1 below. A conservative substitution mutant or variant will 1) have only conservative amino acid substitutions relative to the parent sequence, 2) will have at least 90% sequence identity with respect to the parent sequence, generally at least 95% identity, 96% identity, 97% identity, 98% identity or 99% identity; and 3) will retain voltage sensing activity as that term is defined herein.

TABLE 1

Conservative Amino Acid Substitutions

| For Amino Acid | Code | Replace With |
|---|---|---|
| Alanine | A | D-ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S—Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S—Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4 or 5-phenylproline, AdaA, AdaG, cis-3,4 or 5-phenylproline, Bpa, D-Bpa |
| Proline | P | D-Pro, L-I-thioazolidine-4-carboxylic acid, D-or-L-1-oxazolidine-4-carboxylic acid (Kauer, U.S. Pat. No. (4,511,390) |
| Serine | | D-Ser, Thr, D-Thr, allo-Thr, Met, D-Met, Met (O), D-Met (O), L-Cys, D-Cys |
| Threonine | T | D-Thr, Ser, D-Ser, allo-Thr, Met, D-Met, Met (O), D-Met (O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

A non-conservative mutation is any other amino acid substitution other than the conservative substitutions noted in the above Table 1.

Methods of making conservative amino acid substitutions are also well known to one skilled in the art and include but are not limited to site-specific mutagenesis using oligonucleotide primers and polymerase chain reactions. Optical sensor variants can be expressed and assayed for voltage sensing activity, pKa, and fluorescence detection by methods known in the art and/or described herein to verify that the desired activities of the optical sensor are retained or augmented by the amino acid substitutions. It is contemplated that conservative amino acid substitution variants of the optical sensors described herein can have enhanced activity or superior characteristics for sensing voltage relative to the parent optical sensor. Certain silent or neutral missense mutations can also be made in the nucleic acid encoding an optical sensor by a mutation that does not change the encoded amino acid sequence of the encoded optical sensor. These types of mutations are useful to optimize codon usage which improve recombinant protein expression and production in the desired cell type. Specific site-directed mutagenesis of a nucleic acid encoding an optical sensor in a vector can be used to create specific amino acid mutations and substitutions. Site-directed mutagenesis can be carried out using, e.g., the QUICKCHANGE® site-directed mutagenesis kit from STRATAGENE® according to manufacture's instructions, or by any method known in the art.

As used herein, the term "membrane potential" refers to a calculated difference in voltage between the interior and exterior of a cell. In one embodiment membrane potential, $\Delta V$, is determined by the equation $\Delta V = V_{interior} - V_{exterior}$. For example, if the outside voltage is 100 mV, and the inside voltage is 30 mV, then the difference is −70 mV. Under resting conditions, the membrane potential is predominantly determined by the ion having the greatest conductance across the membrane. In many cells, the membrane potential is determined by potassium, which yields a resting membrane potential of approximately −70 mV. Thus by convention, a cell under resting conditions has a negative membrane potential. In some cells when a membrane potential is reached that is equal to or greater than a threshold potential, an action potential is triggered and the cell undergoes depolarization (i.e., a large increase in the membrane potential). Often, when a cell undergoes depolarization, the membrane potential reverses and reaches positive values (e.g., 35 mV). During resolution of the membrane potential following depolarization towards the resting membrane potential, a cell can "hyperpolarize." The term "hyperpolarize" refers to membrane potentials that are more negative than the resting membrane potential, while the term "depolarize" refers to membrane potentials that are less negative (or even positive) compared to the resting membrane potential. Membrane potential changes can arise by movement of ions through ion channels or ion pumps embedded in the membrane. Membrane potential can be measured across any cellular membrane that comprises ion channels or ion pumps that can maintain an ionic gradient across the membrane (e.g., plasma membrane, mitochondrial inner and outer membranes etc.).

As used herein, the term "change in the membrane potential" refers to an increase (or decrease) in $\Delta V$ of at least 1 mV that is either spontaneous or in response to e.g., environmental or chemical stimuli (e.g., cell-to-cell communication, ion channel modulation, contact with a candidate agent, etc.) compared to the resting membrane potential measured under control conditions (e.g., absence of an agent, impaired cellular communication, etc.). In some embodiments, the membrane potential $\Delta V$ is increased by at least 10 mV, at least 15 mV, at least 20 mV, at least 25 mV, at least 30 mV, at least 35 mV, at least 40 mV, at least 45 mV, at least 50 mV, at least 55 mV, at least 60 mV, at least 65 mV, at least 70 mV, at least 75 mV, at least 80 mV, at least 85 mV, at least 90 mV, at least 95 mV, at least 100 mV, at least 105 mV, at least 110 mV, at least 115 mV, at least 120 mV, at least 125 mV, at least 130 mV, at least 135 mV, at least 140 mV, at least 145 mV, at least 150 mV, at least 155 mV, at least 160 mV, at least 165 V, at least 170 mV, at least 180 mV, at least 190 mV, at least 200 mV or more compared to the membrane potential of a similar cell under control conditions. In other embodiments, the membrane potential is decreased by at least 3 mV, at least 5 mV, at least 10 mV, at least 15 mV, at least 20 mV, at least 25 mV, at least 30 mV, at least 35 mV, at least 40 mV, at least 45 mV, at least 50 mV, at least 55 mV, at least 60 mV, at least 65 mV, at least 70 mV, at least 75 mV, at least 80 mV, at least 85 mV, at least 90 mV, at least 95 mV, at least 100 mV, at least 105 mV, at least 110 mV, at least 115 mV, at least 120 mV, at least 125 mV, at least 130 mV, at least 135 mV, at least 140 mV, at least 145 mV, at least 150 mV or more compared to the membrane potential of a similar cell under control conditions.

As used herein, the phrase "localizes to a membrane of the cell" refers to the preferential localization (trafficking) of the modified microbial rhodopsin protein to the membrane of a cell and can be achieved by e.g., modifying the microbial rhodopsin to comprise a signal sequence that directs the rhodopsin protein to a membrane of the cell (e.g., the plasma membrane, the mitochondrial outer membrane, the mitochondrial inner membrane, etc.). In some embodiments, at least 40% of the modified microbial rhodopsin protein in the cell is localized to the desired cellular membrane compartment (e.g., plasma membrane, mitochondrial membrane etc); in other embodiments, at least 50%, at least 60%, at least 70%, at least 75%, at least 80%, at least 85%, at least 90%, at least 95%, at least 99% of the modified microbial rhodopsin protein is localized to the desired cellular membrane compartment. Similarly, the phrase "localized to a subcellular compartment" refers to the preferential localization (trafficking) of the microbial rhodopsin protein to a particular subcellular compartment (e.g., mitochondria, endoplasmic reticulum, peroxisome etc.). In some embodiments, at least 40% of the modified microbial rhodopsin protein in the cell is localized to the desired subcellular compartment; in other embodiments, at least 50%, at least 60%, at least 70%, at least 75%, at least 80%, at least 85%, at least 90%, at least 95%, or at least 99% of the modified microbial rhodopsin protein is localized to the desired subcellular compartment. In certain embodiment, about 100% is localized to the desired cellular membrane or compartment.

As used herein, the term "introducing to a cell" refers to any method for introducing either an expression vector encoding an optical sensor or a recombinant optical sensor protein described herein into a host cell. Some non-limiting examples of introducing an expression vector into a cell include, for example, calcium phosphate transfection, electroporation, lipofection, or a method using a gene gun or the like. In one embodiment, a recombinant optical sensor protein is introduced to a cell by membrane fusion using a lipid mediated delivery system, such as micelles, liposomes, etc.

As used herein, the phrase "a moiety that produces an optical signal" refers to a molecule (e.g., retinal), or moiety of a molecule, capable of producing a detectable signal such as e.g., fluorescence, chemiluminescence, a colorimetric signal etc. In one embodiment, the modified microbial rhodopsin comprises a fusion molecule with a moiety that produces an optical signal.

As used herein, the phrases "change in the level of fluorescence" or "a change in the level of the optical signal" refer to an increase or decrease in the level of fluorescence from the modified microbial rhodopsin protein or an increase or decrease in the level of the optical signal induced by a change in voltage or membrane potential. In some embodiments, the level of fluorescence or level of optical signal in a cell is increased by at least at least 2%, at least 5%, at least 10%, 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 50-fold, at least 100-fold, at least 500-fold, at least 600-fold, at least 700-fold, at least 800-fold, at least 900-fold, at least 1000-fold, at least 2000-fold, at least 5000-fold, at least 10000-fold or more compared to the same cell or a similar cell under control conditions. Alternatively, the level of fluorescence or level of optical signal in a cell is decreased by at least by at least 20%, at least 30%, at least 40%, at least 50%, at least 60%, at least 70%, at least 80%, at least 90%, at least 95%, at least 99%, or even 100% (i.e., no detectable signal) compared to the same cell or a similar cell under control culture conditions.

As used herein, the phrase "modulates ion channel activity" refers to an increase or decrease in one or more properties of an ion channel that manifests as a change in the membrane potential of a cell. These properties include, e.g., open- or closed-state conductivity, threshold voltage, kinetics and/or ligand affinity. In some embodiments, the one or more properties of interest of an ion channel of a cell as measured by e.g., a change in membrane potential of the cell. In some embodiments, the activity of an ion channel is increased by at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 20-fold, at least 50-fold, at least 100-fold, at least 1000-fold or more in the presence of an agent compared to the activity of the ion channel in the absence of the agent. In other embodiments, the parameter of interest of an ion channel is decreased by at least 20%, at least 30%, at least 40%, at least 50%, at least 60%, at least 70%, at least 80%, at least 90%, at least 95%, or at least 99% in the presence of an agent compared to the activity of the ion channel in the absence of the agent. In some embodiments, the parameter of an ion channel is absent in the presence of an agent compared to the activity of the ion channel in the absence of the agent.

As used herein, the term "targeting sequence" refers to a moiety or sequence that homes to or preferentially associates or binds to a particular tissue, cell type, receptor, organelle, or other area of interest. The addition of a targeting sequence to an optical sensor composition will enhance the delivery of the composition to a desired cell type or subcellular location. The addition to, or expression of, a targeting sequence with the optical sensor in a cell enhances the localization of the optical sensor to a desired location within an animal or subject.

As used herein, the phrase "homologous mutation in another microbial rhodopsin that corresponds to the amino acid mutation in bacteriorhodopsin" refers to mutation of a residue in a desired microbial rhodopsin that is expected to have a similar effect to a substantially similar mutation in bacteriorhodopsin. One of skill in the art can easily locate a homologous residue in their desired microbial rhodopsin by performing an alignment of conserved regions of the desired microbial rhodopsin with a bacteriorhodopsin sequence using a computer program such as ClustalW. Examples of homologous mutations include the mutations made in the Examples set forth in this application.

The visible light spectrum ranges from approximately 400 nm to approximately 750 nm. It is understood in the art that, since light is a spectrum, there will be overlap in wavelengths found between the adjacent colors in the spectrum. Longest visible wavelengths are at the red end of the spectrum. Shortest visible wavelengths are at the blue end of the spectrum. As used herein, "red light" refers to a wavelength from about 600 nm to about 750 nm. As used herein, "orange light" refers to a wavelength from about 580 nm to about 620 nm. As used herein, "yellow light" refers to a wavelength from about 560 nm to about 585 nm. As used herein, "green light" refers to a wavelength from about 500 nm to about 565 nm. As used herein, "blue light" generally refers to a wavelength from about 435 nm to about 500 nm. As used herein, "indigo light" generally refers to a wavelength from about 420 nm to about 440 nm. As used herein, "violet light" generally refers to a wavelength from about 400 nm to about 420 nm. A red-shifted spectrum refers to either an absorption or emission spectrum towards longer wavelengths (i.e., towards the red end of the spectrum). A blue-shifted spectrum refers to either an absorption or emission spectrum towards shorter wavelengths (i.e., towards the blue end of the spectrum).

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

BRIEF DESCRIPTION OF THE SEQUENCES

SEQ ID NO:1 is the amino acid sequence of the wild-type (WT) Archaerhodopsin 3, also referred to herein as Arch 3 or Ar3.

SEQ ID NO:2 is the amino acid sequence of QuarsAr1 with substitutions at amino acid positions 60, 80, 95, 106, or 161 (positions indicated with underlining).

SEQ ID NO:3 is the amino acid sequence of QuarsAr2 with substitutions at amino acid positions 60, 80, 95, 106, or 161 (positions indicated with underlining).

SEQ ID NO:4 is an exemplary polynucleotide sequence that encodes wild-type (WT) Archaerhodopsin 3.

SEQ ID NO:5 is an exemplary polynucleotide sequence that encodes QuarsAr1.

SEQ ID NO:6 is an exemplary polynucleotide sequence that encodes QuarsAr2.

SEQ ID NO:7 is the trafficking sequence (TS).

SEQ ID NO:8 is the endoplasmic reticulum (ER) export motif from Kir2.1 (FCYENE).

SEQ ID NO:9 is an exemplary polynucleotide sequence that encodes trafficking sequence (TS).

SEQ ID NO:10 is an exemplary polynucleotide sequence that endoplasmic reticulum (ER) export motif

TABLE 2

| Name: | Sequence | SEQ ID NO: |
|---|---|---|
| Arch 3 (WT) | MDPIALQAGYDLLGDGRPETLWLGIGTLLMLIGTFYFLVRGWG VTDKDAREYYAVTILVPGIASAAYLSMFFGIGLTEVTVGGEML DIYYARYADWLFTTPLLLLDLALLAKVDRVTIGTLVGVDALMI VTGLIGALSHTAIARYSWWLFSTICMIVVLYFLATSLRSAAKER GPEVASTFNTLTALVLVLWTAYPILWIIGTEGAGVVGLGIETLL FMVLDVTAKVGFGFILLRSRAILGDTEAPEPSAGADVSAAD | 1 |
| QuasAr1 | MDPIALQAGYDLLGDGRPETLWLGIGTLLMLIGTFYFLVRGWG VTDKDAREYYAVTILVSGIASAAYLSMFFGIGLTEVSVGGEML DIYYARYAHWLFTTPLLLLHLALLAKVDRVTIGTLVGVDALMI VTGLIGALSHTAIARYSWWLFSTICMIVVLYVLATSLRSAAKER GPEVASTFNTLTALVLVLWTAYPILWIIGTEGAGVVGLGIETLL FMVLDVTAKVGFGFILLRSRAILGDTEAPEPSAGADVSAAD | 2 |
| QuasAr2 | MDPIALQAGYDLLGDGRPETLWLGIGTLLMLIGTFYFLVRGWG VTDKDAREYYAVTILVSGIASAAYLSMFFGIGLTEVSVGGEML DIYYARYAQWLFTTPLLLLHLALLAKVDRVTIGTLVGVDALMI VTGLIGALSHTAIARYSWWLFSTICMIVVLYVLATSLRSAAKER GPEVASTFNTLTALVLVLWTAYPILWIIGTEGAGVVGLGIETLL FMVLDVTAKVGFGFILLRSRAILGDTEAPEPSAGADVSAAD | 3 |
| Arch 3 (WT) | ATGGACCCCATCGCTCTGCAGGCTGGTTACGACCTGCT GGGTGACGGCAGACCTGAAACTCTGTGGCTGGGCATC GGCACTCTGCTGATGCTGATTGGAACCTTCTACTTTCTG GTCCGCGGATGGGGAGTCACCGATAAGGATGCCCGGG AATATTACGCTGTGACTATCCTGGTGCCCGGAATCGCA TCCGCCGCATATCTGTCTATGTTCTTTGGTATCGGCTT ACTGAGGTGACCGTCGGGGGCGAAATGTTGGATATCT ATTATGCCAGGTACGCCGACTGGCTGTTTACCACCCCA CTTCTGCTGCTGGATCTGGCCCTTCTCGCTAAGGTGGA TCGGGTGACCATCGGCACCCTGGTGGGTGTGGACGCCC TGATGATCGTCACTGGCCTCATCGGAGCCTTGAGCCAC ACGGCCATAGCCAGATACAGTTGGTGGTTGTTCTCTAC AATTTGCATGATAGTGGTGCTCTATTTTCTGGCTACATC CCTGCGATCTGCTGCAAAGGAGCGGGGCCCCGAGGTG GCATCTACCTTTAACACCCTGACAGCTCTGGTCTTGGT GCTGTGGACCGCTTACCCTATCCTGTGGATCATAGGCA CTGAGGGCGCTGGCGTGGTGGGCCTGGGCATCGAAAC TCTGCTGTTTATGGTGTTGGACGTGACTGCCAAGGTCG GCTTTGGCTTTATCCTGTTGAGATCCCGGGCTATTCTGG GCGACACCGAGGCACCAGAACCCAGTGCCGGTGCCGA TGTCAGTGCCGCCGACTAA | 4 |
| QuasAr1 | ATGGACCCCATCGCTCTGCAGGCTGGITACGACCTGCTGGG TGACGGCAGACCTGAAACTCTGTGGCTGGGCATCGGCACTC TGCTGATGCTGATTGGAACCTTCTACTTTCTGGTCCGCGGAT GGGGAGTCACCGATAAGGATGCCCGGGAATATTACGCTGTG ACTATCCTGGTGTCNGGAATCGCATCCGCCGCATATCTGTCT ATGTTCTTTGGTATCGGCTTACTGAGGTGTCNGTCGGGGG CGAAATGTTGGATATCTATTATGCCAGGTACGCCCAYTGGC TGTTTACCACCCCACTTCTGCTGCTGCAYCTGGCCCTTCTCG CTAAGGTGGATCGGGTGACCATCGGCACCCTGGTGGGTGTG GACGCCCTGATGATCGTCACTGGCCTCATCGGAGCCTTGAG CCACACGGCCATAGCCAGATACAGTTGGTGGTTGTTCTCTAC AATTTGCATGATAGTGGTGCTCTATGTNCTGGCTACATCCCT GCGATCTGCTGCAAAGGAGCGGGGCCCCGAGGTGGCATCTA CCTTTAACACCCTGACAGCTCTGGTCTTGGTGCTGTGGACCG CTTACCCTATCCTGTGGATCATAGGCACTGAGGGCGCTGGC GTGGTGGGCCTGGGCATCGAAACTCTGCTGTTTATGGTGTTG GACGTGACTGCCAAGGTCGGCTTTGGCTTTATCCTGTTGAGA TCCCGGGCTATTCTGGGCGACACCGAGGCACCAGAACCCAG TGCCGGTGCCGATGTCAGTGCCGCCGACTAA | 5 |
| QuasAr1 | ATGGACCCCATCGCTCTGCAGGCTGGTTACGACCTGCTGGG TGACGGCAGACCTGAAACTCTGTGGCTGGGCATCGGCACTC TGCTGATGCTGATTGGAACCTTCTACTTTCTGGTCCGCGGAT GGGGAGTCACCGATAAGGATGCCCGGGAATATTACGCTGTG ACTATCCTGGTGTCNGGAATCGCATCCGCCGCATATCTGTCT ATGTTCTTTGGTATCGGCTTACTGAGGTGAGYGTCGGGGG CGAAATGTTGGATATCTATTATGCCAGGTACGCCCAYTGGC TGTTTACCACCCCACTTCTGCTGCTGCAYCTGGCCCTTCTCG CTAAGGTGGATCGGGTGACCATCGGCACCCTGGTGGGTGTG GACGCCCTGATGATCGTCACTGGCCTCATCGGAGCCTTGAG CCACACGGCCATAGCCAGATACAGTTGGTGGTTGTTCTCTAC AATTTGCATGATAGTGGTGCTCTATGTNCTGGCTACATCCCT GCGATCTGCTGCAAAGGAGCGGGGCCCCGAGGTGGCATCTA | 28 |

TABLE 2-continued

| Name: | Sequence | SEQ ID NO: |
|---|---|---|
| | CCTTTAACACCCTGACAGCTCTGGTCTTGGTGCTGTGGACCG CTTACCCTATCcrGTGGATCATAGGCACTGAGGGCGCTGGC GTGGTGGGCCTGGGCATCGAAACTCTGCTGTTTATGGTGTTG GACGTGACTGCCAAGGTCGGCTTTGGCTTTATCCTGTTGAGA TCCCGGGCTATTCTGGGCGACACCGAGGCACCAGAACCCAG TGCCGGTGCCGATGTCAGTGCCGCCGACTAA | |
| QuasAr1 | ATGGACCCCATCGCTCTGCAGGCTGGTTACGACCTGCTGGG TGACGGCAGACCTGAAACTCTGTGGCTGGGCATCGGCACTC TGCTGATGCTGATTGGAACCTTCTACTTTCTGGTCCGCGGAT GGGGAGTCACCGATAAGGATGCCCGGGAATATTACGCTGTG ACTATCCTGGTGAGYGGAATCGCATCCGCCGCATATCTGTCT ATGTTCTTTGGTATCGGGCTTACTGAGGTGTCNGTCGGGGG CGAAATGTTGGATATCTATTATGCCAGGTACGCCCAYTGGC TGTTTACCACCCCACTTCTGCTGCTGCAYCTGGCCCTTCTCG CTAAGGTGGATCGGGTGACCATCGGCACCCTGGTGGGTGTG GACGCCCTGATGATCGTCACTGGCCTCATCGGAGCCTTGAG CCACACGGCCATAGCCAGATACAGTTGGTGGTTGTTCTCTAC AATTTGCATGATAGTGGTGCTCTATGTNCTGGCTACATCCCT GCGATCTGCTGCAAAGGAGCGGGGCCCCGAGGTGGCATCTA CCTTTAACACCCTGACAGCTCTGGTCTTGGTGCTGTGGACCG CTTACCCTATCCTGTGGATCATAGGCACTGAGGGCGCTGGC GTGGTGGGCCTGGGCATCGAAACTCTGCTGTTTATGGTGTTG GACGTGACTGCCAAGGTCGGCTTTGGCTTTATCCTGTTGAGA TCCCGGGCTATTCTGGGCGACACCGAGGCACCAGAACCCAG TGCCGGTGCCGATGTCAGTGCCGCCGACTAA | 29 |
| QuasAr1 | ATGGACCCCATCGCTCTGCAGGCTGGTTACGACCTGCTGGG TGACGGCAGACCTGAAACTCTGTGGCTGGGCATCGGCACTC TGCTGATGCTGATTGGAACCTTCTACTTTCTGGTCCGCGGAT GGGGAGTCACCGATAAGGATGCCCGGGAATATTACGCTGTG ACTATCCTGGTGAGYGGAATCGCATCCGCCGCATATCTGTCT ATGTTCTTTGGTATCGGGCTTACTGAGGTGAGYGTCGGGGC CGAAATGTTGGATATCTATTATGCCAGGTACGCCCAYTGGC TGTTTACCACCCCACTTCTGCTGCTGCAYCTGGCCCTTCTCG CTAAGGTGGATCGGGTGACCATCGGCACCCTGGTGGGTGTG GACGCCCTGATGATCGTCACTGGCCTCATCGGAGCCTTGAG CCACACGGCCATAGCCAGATACAGTTGGTGGTTGTTCTCTAC AATTTGCATGATAGTGGTGCTCTATGTNCTGGCTACATCCCT GCGATCTGCTGCAAAGGAGCGGGGCCCCGAGGTGGCATCTA CCTTTAACACCCTGACAGCTCTGGTCTTGGTGCTGTGGACCG CTTACCCTATCCTGTGGATCATAGGCACTGAGGGCGCTGGC GTGGTGGGCCTGGGCATCGAAACTCTGCTGTTTATGGTGTTG GACGTGACTGCCAAGGTCGGCTTTGGCTTTATCCTGTTGAGA TCCCGGGCTATTCTGGGCGACACCGAGGCACCAGAACCCAG TGCCGGTGCCGATGTCAGTGCCGCCGACTAA | 30 |
| QuasAr2 | ATGGACCCCATCGCTCTGCAGGCTGGTTACGACCTGCTGGG TGACGGCAGACCTGAAACTCTGTGGCTGGGCATCGGCACTC TGCTGATGCTGATTGGAACCTTCTACTTTCTGGTCCGCGGAT GGGGAGTCACCGATAAGGATGCCCGGGAATATTACGCTGTG ACTATCCTGGTGTCNGGAATCGCATCCGCCGCATATCTGTCT ATGTTCTTTGGTATCGGGCTTACTGAGGTGTCNGTCGGGGG CGAAATGTTGGATATCTATTATGCCAGGTACGCCCARTGGC GTTTACCACCCCACTTCTGCTGCTGCAYCTGGCCCTTCTCGC TAAGGTGGATCGGGTGACCATCGGCACCCTGGTGGGTGTGG ACGCCCTGATGATCGTCACTGGCCTCATCGGAGCCTTGAGC CACACGGCCATAGCCAGATACAGTTGGTGGTTGTTCTCTAC AATTTGCATGATAGTGGTGCTCTATGTNCTGGCTACATCCCT GCGATCTGCTGCAAAGGAGCGGGGCCCCGAGGTGGCATCTA CCTTTAACACCCTGACAGCTCTGGTCTTGGTGCTGTGGACCG CTTACCCTATCCTGTGGATCATAGGCACTGAGGGCGCTGGC GTGGTGGGCCTGGGCATCGAAACTCTGCTGTTTATGGTGTTG GACGTGACTGCCAAGGTCGGCTTTGGCTTTATCCTGTTGAGA TCCCGGGCTATTCTGGGCGACACCGAGGCACCAGAACCCAG TGCCGGTGCCGATGTCAGTGCCGCCGACTAA | 6 |
| QuasAr2 | ATGGACCCCATCGCTCTGCAGGCTGGTTACGACCTGCTGGG TGACGGCAGACCTGAAACTCTGTGGCTGGGCATCGGCACTC TGCTGATGCTGATTGGAACCTTCTACTTTCTGGTCCGCGGAT GGGGAGTCACCGATAAGGATGCCCGGGAATATTACGCTGTG ACTATCCTGGTGTCNGGAATCGCATCCGCCGCATATCTGTCT ATGTTCTTTGGTATCGGGCTTACTGAGGTGAGYGTCGGGGG CGAAATGTTGGATATCTATTATGCCAGGTACGCCCARTGGCT GTTTACCACCCCACTTCTGCTGCTGCAYCTGGCCCTTCTCGC TAAGGTGGATCGGGTGACCATCGGCACCCTGGTGGGTGTGG | 31 |

TABLE 2-continued

| Name: | Sequence | SEQ ID NO: |
|---|---|---|
| | ACGCCCTGATGATCGTCACTGGCCTCATCGGAGCCTTGAGC<br>CACACGGCCATAGCCAGATACAGTTGGTGGTTGTTCTCTAC<br>AATTTGCATGATAGTGGTGCTCTATGTNCTGGCTACATCCCT<br>GCGATCTGCTGCAAAGGAGCGGGGCCCCGAGGTGGCATCTA<br>CCTTTAACACCCTGACAGCTCTGGTCTTGGTGCTGTGGACCG<br>CTTACCCTATCCTGTGGATCATAGGCACTGAGGGCGCTGGC<br>GTGGTGGGCCTGGGCATCGAAACTCTGCTGTTTATGGTGTTG<br>GACGTGACTGCCAAGGTCGGCTTTGGCTTTATCCTGTTGAGA<br>TCCCGGGCTATTCTGGGCGACACCGAGGCACCAGAACCCAG<br>TGCCGGTGCCGATGTCAGTGCCGCCGACTAA | |
| QuasAr2 | ATGGACCCCATCGCTCTGCAGGCTGGTTACGACCTGCTGGG<br>TGACGGCAGACCTGAAACTCTGTGGCTGGGCATCGGCACTC<br>TGCTGATGCTGATTGGAACCTTCTACTTTCTGGTCCGCGGAT<br>GGGGAGTCACCGATAAGGATGCCCGGGAATATTACGCTGTG<br>ACTATCCTGGTGAGYGGAATCGCATCCGCCGCATATCTGTCT<br>ATGTTCTTTGGTATCGGGCTTACTGAGGTGTCNGTCGGGGG<br>CGAAATGTTGGATATCTATTATGCCAGGTACGCCCARTGGCT<br>GTTTACCACCCCACTTCTGCTGCTGCAYCTGGCCCTTCTCGC<br>TAAGGTGGATCGGGTGACCATCGGCACCCTGGTGGGTGTGG<br>ACGCCCTGATGATCGTCACTGGCCTCATCGGAGCCTTGAGC<br>CACACGGCCATAGCCAGATACAGTTGGTGGTTGTTCTCTAC<br>AATTTGCATGATAGTGGTGCTCTATGTNCTGGCTACATCCCT<br>GCGATCTGCTGCAAAGGAGCGGGGCCCCGAGGTGGCATCTA<br>CCTTTAACACCCTGACAGCTCTGGTCTTGGTGCTGTGGACCG<br>CTTACCCTATCCTGTGGATCATAGGCACTGAGGGCGCTGGC<br>GTGGTGGGCCTGGGCATCGAAACTCTGCTGTTTATGGTGTTG<br>GACGTGACTGCCAAGGTCGGCTTTGGCTTTATCCTGTTGAGA<br>TCCCGGGCTATTCTGGGCGACACCGAGGCACCAGAACCCAG<br>TGCCGGTGCCGATGTCAGTGCCGCCGACTAA | 32 |
| QuasAr2 | ATGGACCCCATCGCTCTGCAGGCTGGTTACGACCTGCTGGG<br>TGACGGCAGACCTGAAACTCTGTGGCTGGGCATCGGCACTC<br>TGCTGATGCTGATTGGAACCTTCTACTTTCTGGTCCGCGGAT<br>GGGGAGTCACCGATAAGGATGCCCGGGAATATTACGCTGTG<br>ACTATCCTGGTGAGYGGAATCGCATCCGCCGCATATCTGTCT<br>ATGTTCTTTGGTATCGGGCTTACTGAGGTGAGYGTCGGGGG<br>CGAAATGTTGGATATCTATTATGCCAGGTACGCCCARTGGCT<br>GTTTACCACCCCACTTCTGCTGCTGCAYCTGGCCCTTCTCGC<br>TAAGGTGGATCGGGTGACCATCGGCACCCTGGTGGGTGTGG<br>ACGCCCTGATGATCGTCACTGGCCTCATCGGAGCCTTGAGC<br>CACACGGCCATAGCCAGATACAGTTGGTGGTTGTTCTCTAC<br>AATTTGCATGATAGTGGTGCTCTATGTNCTGGCTACATCCCT<br>GCGATCTGCTGCAAAGGAGCGGGGCCCCGAGGTGGCATCTA<br>CCTTTAACACCCTGACAGCTCTGGTCTTGGTGCTGTGGACCG<br>CTTACCCTATCCTGTGGATCATAGGCACTGAGGGCGCTGGC<br>GTGGTGGGCCTGGGCATCGAAACTCTGCTGTTTATGGTGTTG<br>GACGTGACTGCCAAGGTCGGCTTTGGCTTTATCCTGTTGAGA<br>TCCCGGGCTATTCTGGGCGACACCGAGGCACCAGAACCCAG<br>TGCCGGTGCCGATGTCAGTGCCGCCGACTAA | 33 |
| Trafficking sequence | SRITSEGEYIPLNIDINVGG | 7 |
| ER export motif from Kir2.1 | FCYENE | 8 |
| Trafficking sequence | agtagaatcacaagcgaagacgagtacatcccctggatcaaataaacataaatgtaggtgga | 9 |
| ER export motif from Kir2.1 | ttttgttatgagaatga | 10 |

*can be TCN or AGY where N is any nucleic acid, Y is t/u or c; R is g or a

BRIEF DESCRIPTION OF THE FIGURES

The accompanying drawings are not intended to be drawn to scale. In the Drawings, for purposes of clarity, not every component may be labeled in every drawing.

FIGS. 1A-1H show non-pumping Arch-derived voltage indicators with improved speed, sensitivity, and brightness. FIG. 1A shows the hierarchical screen to select improved Arch mutants. Five rounds of random mutagenesis and screening for brightness were performed in E. coli. The brightest mutants were subjected to targeted mutagenesis and screening for speed and voltage sensitivity in HeLa cells via induced transient voltage (FIG. 2). FIG. 1B shows the fluorescence of Arch mutants fused to eGFP and expressed in HEK cells, as a function of illumination intensity. The plot shows Arch fluorescence (640 nm exc., 660-760 nm em.) normalized by illumination intensity (640 nm) and by eGFP fluorescence (488 nm exc., 525-575 nm em.) to control for cell-to-cell variations in expression. A linear fluorophore (i.e., brightness proportional to illumination intensity) would appear as a horizontal line. Error bars represent s.e.m. (n=5-7 cells for each mutant). FIG. 1C shows fluorescence vs. membrane voltage for Arch, QuasAr1, and QuasAr2 expressed in HEK cells. FIG. 1D shows fluorescence responses to a step in membrane voltage from −70 to +30 mV. FIG. 1E shows simultaneous optical and electrical recording of APs in a rat hippocampal neuron expressing QuasAr1. Frame rate 1 kHz. FIG. 1F shows the overlay of mean optically and electrically recorded AP waveforms. Frame rate 2 kHz. FIGS. 1G and H show the same as FIGS. 1E and 1F in neurons expressing QuasAr2. Data in FIGS. 1B-H acquired on a 128×128 pixel EMCCD camera (see Examples).

FIG. 2A shows the experimental setup, showing two platinum electrodes placed on either side of a transfected cell. V(t) represents the pulse generator and high-voltage amplifier. FIG. 2B shows frames from a movie of a HeLa cell expressing QuasAr1. The cell was stimulated with an electrical pulse (20 ms, 50 V/cm). The images show the fluorescence response (ΔF/F). The arrow labeled 'E' indicates the direction of the electric field. FIG. 2C shows fluorescence of the cell poles during the ITV experiment shown in FIG. 2B. Gray marks above the fluorescence traces indicate timing and duration of the ITV pulses. FIG. 2D shows the zoomed in view of one fluorescence intensity peak from FIG. 2C.

FIG. 3A shows the locations of mutations in QuasAr1, modeled on the crystal structure of Arch-2 (PDB: 2EI4)[70]. Arch-2 has 90% amino acid identity with Arch-3. The retinal chromophore is colored blue and mutations are colored green. FIG. 3B (top) shows images of E. coli pellets expressing Arch, QuasAr1, and QuasAr2. FIG. 3B (bottom) shows images of solubilized protein. FIG. 3C shows the absorption spectra of Arch, QuasAr1 and QuasAr2, measured on solubilized protein. FIG. 3D shows the excitation and emission spectra measured on QuasAr1 and QuasAr2. Arch was too dim to measure in the fluorimeter. Emission spectra were recorded with $\lambda_{exc}$=600 nm. Excitation spectra were measured with $\lambda_{em}$=750 nm.

FIG. 4A shows wild-type Arch, expressed in cultured rat hippocampal neurons, generated substantial photocurrent of 220±30 pA (n=6 cells) under red (1 s, 640 nm, 300 W/cm2) and 140±25 pA under blue (1 s, 488 nm, 500 mW/cm²) illumination (n=5 cells). Steady state photocurrents were calculated by averaging the current over the last 0.25 seconds of light exposure and subtracting the holding current (cells held at −65 mV) in the dark. These currents hyperpolarized cells by 25±4 mV and 19±3 mV, respectively. Neither QuasAr1 (n=9 cells) nor QuasAr2 (n=7 cells) generated detectable photocurrents under either illumination condition, nor under red illumination at up to 900 W/cm². FIG. 4 B shows a Comparison of fluorescence between QuasAr mutants and Arch double mutants, expressed as eGFP fusions in HEK cells. The double mutants had mutations at the locations of the proton acceptor (Asp95) and proton donor (Asp106) to the Schiff base. QuasAr1 includes mutations D95H, D106H, and QuasAr2 includes mutations D95Q, D106H. The three additional backbone mutations in the QuasArs (P60S, T80S, F161V) increased brightness relative to the double mutants. Fluorescence of each Arch mutant was measured with excitation at 640 nm and emission from 660-760 nm. To control for variation in expression level, fluorescence was normalized by eGFP fluorescence ($\lambda_{exc}$=488 nm, $\lambda_{em}$=510-550 nm). Error bars represent s.e.m. for measurements on n=5-10 cells.

FIG. 5A shows the effect of blue illumination on QuasAr fluorescence. HEK293 cells expressing QuasAr1 or QuasAr2 were exposed to continuous excitation at 640 nm (300 W/cm²) and pulses of illumination at 488 nm (50 ms, 5 Hz). The intensity of the blue pulses increased from 0.06 to 1.8 W/cm². FIG. 5B shows quantification of crosstalk. Illumination with blue light at typical intensity used to excite a blue-light activator (CheRiff) (0.2 W/cm²) increased QuasAr1 fluorescence by 1.1% and QuasAr2 fluorescence by 0.6%. Illumination at with blue light at 1 W/cm² increased QuasAr1 fluorescence by 3.4% and QuasAr2 fluorescence by 2.4%. Error bars represent s.e.m. for n=5 cells for each QuasAr.

FIG. 6A is at depolarizing (positive) membrane voltage; the microbial rhodopsin absorbs strongly and quenches the fluorescence of the fluorescent protein. FIG. 6B is at hyperpolarizing (negative) membrane voltage, the microbial rhodopsin absorbs weakly, so the fluorescent protein emits strongly.

FIGS. 7A-7C show the voltage-indicating properties of five eFRET GEVIs spanning the visible spectrum. FIG. 7A shows images of HEK293 cells expressing the eFRET fusion of the indicated fluorescent protein to QuasAr2. Scale bar 10 µm. FIG. 7B shows fluorescence as a function of voltage. FIG. 7C shows the fluorescence response to a step in membrane voltage from −70 mV to +30 mV.

FIG. 8A shows images of cultured rat hippocampal neurons expressing eFRET GEVIs. FIG. 8B shows simultaneous patch clamp electrophysiology and fluorescence recordings of neuronal action potentials. FIG. 8C shows close-ups showing the action potential waveform as reported by patch clamp electrophysiology and as reported by the eFRET GEVI.

FIGS. 9A-9E shows a comparison of voltage-indicating properties of QuasArs and ArcLight A242 in culture. FIG. 9A shows fluorescence as a function of membrane voltage in HEK293T cells. ArcLight showed voltage sensitivity of −32±3% ΔF/F per 100 mV (n=7 cells), comparable in magnitude to QuasAr1 and 2.8-fold smaller than QuasAr2. FIG. 9B shows the response of ArcLight to steps in membrane voltage. ArcLight showed bi-exponential kinetics in response to rising or falling voltage steps (Table 6). Mean half-response times were 42±8 ms and 76±5 ms on rising and falling edges at 23° C. (n=6 cells) and 11±1 and 17±2 ms on rising and falling edges at 34° C. (n=7 cells). FIG. 9C shows step responses of ArcLight and QuasArs overlaid on the same time axis at 23° C. (top) and 34° C. (bottom). FIG. 9D shows Continuous illumination of a neuron expressing ArcLight (488 nm, 10 W/cm$^2$) led to photobleaching with a time constant of 70 s. Inset: Low-magnification image of the neuron. Scale bar 20 μm. Cyan box shows field of view used for high-speed (1 kHz frame rate) movies of fluorescence dynamics. Fluorescence was calculated by preferentially weighting the pixels whose intensity co-varies with the whole-field average. FIG. 9E shows single-trial fluorescence response of ArcLight and QuasAr2 to a single AP, recorded at 34° C. and a 1 kHz frame rate. ArcLight reported action potentials with an amplitude of ΔF/F=−2.7±0.5% (n=5 cells) and a single-trial signal-to-noise ratio (SNR) of 8.8±1.6 (488 nm, 10 W/cm$^2$). ArcLight distorted the AP waveforms to have a width of 14.5±3.0 ms at 70% maximal fluorescence deviation, compared to the true width of 1.3±0.1 ms simultaneously recorded with a patch pipette. QuasAr2 reported APs at 34° C. and 23° C. with comparable single-trial SNR (SNR at 34° C.: 41±3, 300 W/cm$^2$, n=8 cells).

DETAILED DESCRIPTION OF THE INVENTION

Figure 1E:
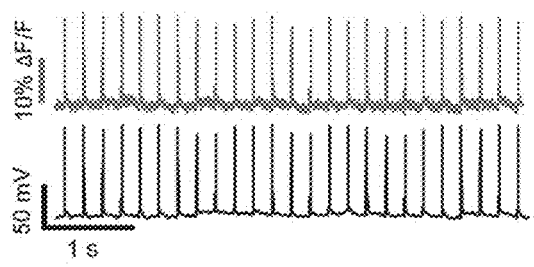

The present invention is based, at least in part, on the discovery of improved mutants of a microbial rhodopsin proteins (e.g., Archaerhodopsin) or modified microbial rhodopsin proteins that have reduced ion pumping activity, compared to the wild type microbial rhodopsin protein from which they are derived. The polypeptides provided herein can be used as an optically detectable sensor to sense voltage across membranous structures, such as cells and sub-cellular organelles. That is, the polypeptides provided herein can be used as voltage sensors to measure changes in membrane potential of cells and sub-cellular organelles, including prokaryotic and eukaryotic cells. The optical sensors described herein are not constrained by the need for electrodes and permit electrophysiological studies to be performed in, e.g., subcellular compartments (e.g., mitochondria) or in small cells (e.g., bacteria). The optical sensors described herein can be used in methods for drug screening, in research settings, and in in vivo imaging systems. The voltage indicators are generally referred to as genetically encoded voltage indicators (GEVIs).

Table 3 shows exemplary approximate characteristics of fluorescent voltage indicating proteins and contains representative members of the families of fluorescent indicators.

TABLE 3

Representative members of families of fluorescent indicators.

| Molecule | Approx ΔF/F per 100 mV | Approximate response time | Comments |
|---|---|---|---|
| VSFP 2.3, Knopfel, T. et al. J. Neurosci. 30, 14998-15004 (2010) | 9.5% | 78 ms | Ratiometric (ΔR/R) |
| VSFP 2.4 Knopfel, T. et al. J. Neurosci. 30, 14998-15004 (2010) | 8.9% | 72 ms | Ratiometric (ΔR/R) |
| VSFP 3.1, Lundby, A., et al., PLoS One 3, 2514 (2008) | 3% | 1-20 ms | Protein |
| Mermaid, Perron, A. et al. Front Mol Neurosci. 2, 1-8 (2009) | 9.2% | 76 | Ratiometric (ΔR/R) |
| SPARC, Ataka, K. & Pieribone, V. A. Biophys. J. 82, 509-516 (2002) | 0.5% | 0.8 ms | Protein |
| Flash, Siegel, M. S. & Isacoff, E. Y. Neuron 19, 735-741 (1997) | 5.1% | 2.8-85 ms | Protein |
| PROPS, described in U.S. patent application No. 2013/0224756 | 150% | 5 ms | Protein |
| Arch 3 WT, described in U.S. patent application No. 2013/0224756 | 66% | <0.5 ms | Protein |
| Arch D95N, described in U.S. patent application No. 2013/0224756 | 100% | 41 ms | Protein |

Generally, GEVIs should have at least one or more of the following general attributes including:

High speed: The reporter generally should not distort the waveform of action potentials in the cells. The action potentials depends on the cells being measured. For example, action potentials that rise and fall in less than 0.5 ms, 0.1 ms or 1 ms.

High sensitivity: The reporter generally exhibits a large change in fluorescence over the physiological voltage range (−70 mV to +30 mV). In certain cases, the change in fluorescent is linear.

High brightness and photostability: For high-speed imaging, many photons are generally recorded in a short interval. The reporter should generally maintain a stable level of baseline fluorescence throughout an experiment.

Efficient trafficking to and uniform distribution throughout the plasma membrane: reporters caught in internal structures contributes to background fluorescence and noise, but not to voltage sensitivity.

Absence of perturbation to endogenous neuronal dynamics: the reporter should generally preserve membrane electrical parameters, and generally should not affect expression or trafficking of other membrane proteins, patterns of gene expression, or cellular metabolism or physiology.

Far red excitation and emission spectra: Compared to blue light (typically used to excite GFP), red light offers:

far lower tissue autofluorescence: Brain autofluorescence, dominated by FAD-containing proteins, has excitation and emission spectral that are nearly indistinguishable from GFP;

better tissue penetration: Photons propagate through brain tissue with a mean free path of $d\sim\lambda^{-2.3}$, where $\lambda$ is the wavelength. Excitation light at 640 nm propagates nearly twice as far as excitation light at 488 nm.

lower phototoxicity. On account of fewer endogenous chromophores at the red end of the spectrum, red excitation tends to preserve cell health better than blue excitation.

Improved voltage indicators are useful in disease modeling, using various cells, such as but not limited to primary and human iPS and ES-derived cells; and in studies of intact tissue in, for example, mice, zebrafish, *C. elegans*, and *Drosophila* fruit flies. In certain embodiments, the cells are neurons or cardiomyocytes. Studies using the protein reporter, Archaerhodopsin 3 (Arch), indicated that Arch is a fast and sensitive voltage indicator[1] but had properties that could be improved upon.[2] Other GEVIs are based on fusion of transmembrane voltage-sensing domains to fluorescent proteins such as GFP. In some of these, voltage modulates the brightness of a single fluorescent fusion,[3,4] while in others, voltage modulates the efficiency of fluorescence resonance energy transfer (FRET) between a pair of fluorescent fusions.[5,6] Fluorescent protein-based voltage sensors tend to have high brightness, but limited speed and sensitivity, and photobleaching can be a concern. Thus, there is strong demand for improved GEVIs.

Provided herein are polypeptides useful as genetically encoded voltage indicators (GEVIs). As used herein, the inventive polypeptides are also referred to as GEVIs. In certain embodiments, the polypeptides are variants of archaerhodopsin. In certain embodiments, the polypeptides are variants of archaerhodopsin 3 (Arch) (SEQ ID NO: 1). In certain embodiments, the polypeptides are variants of an archaerhodopsin-based voltage indicator. The polypeptides provided herein are brighter than Arch with a brightness that is a linear function of illumination intensity.

The polypeptides provided herein were identified using directed evolution (using, e.g., error-prone PCR or PCR DNA shuffling) of Arch variants. About five rounds of directed evolution were used to prepare the Arch mutant library, followed by random mutagenesis. Site-directed mutagenesis is then used to further identify mutants with improved voltage sensitivity and speed. Using the foregoing methods, mutations of amino acids distant from the retinal chromophore were identified that resulted in polypeptides with improved brightness. In certain embodiments, the polypeptides comprise a C-terminal endoplasmic reticulum (ER) export motif and a trafficking sequence (TS). The TS comprises the amino acid sequence SRITSEGEYIPLDQIDIN-VGG (SEQ ID NO: 7), wherein the amino acid K is optionally found at the N-terminal end of the sequence. The ER comprises the amino acid sequence FCYENE (SEQ ID NO: 8), wherein the amino acid V is optionally found at the C-terminal end of the sequence. An exemplary nucleic acid coding sequence for the TS sequence is: agtagaatcacaagcgaaggcgagtacatcccctggatcaaatagacataaatgtaggtgga (SEQ ID NO: 9), wherein the sequence optionally comprises the nucleotides aag at the 5'-end that encodes for the optional K residue. An exemplary nucleic acid coding sequence for the ER sequence is: ttttgttatgagaatgaa (SEQ ID NO: 10), wherein the sequence optionally comprises nucleotides gtg at the 3'-end that encodes for the optional V residue.

Polypeptides and Polynucleotides

The polypeptides provided herein are derived from archaerhodopsin modified to reduce or inhibit the light-induced ion pumping activity. Thus, the polypeptides and polynucleotides encoding the polypeptides provided herein are non-naturally occurring. Such modifications permit the modified Archaerhodopsin to sense voltage without altering the membrane potential of the cell with its native ion pumping activity and thus altering the voltage of the system. It is contemplated herein that other archaerhodopsin protein or variants thereof can be engineered as described herein to serve as voltage-indicating proteins.

In certain embodiments, the polypeptides described herein are based on archaerhodopsin-3 (Arch 3). Mutation of D95 in Arch3 reduces or inhibits ion pumping activity. Other mutations impart other advantageous properties to the archaerhodopsin-based GEVIs, including increased fluorescence brightness, improved photostability, tuning of the sensitivity and dynamic range of the voltage response, increased response speed, and tuning of the absorption and emission spectra. Amino acids at positions 95 and 106 are associated with the proton translocation during photocycle and at least one amino acid at position 60, 80, or 161 of Arch 3 were are associated with improved properties such as brightness. The amino acid at position 60 is in close proximity to the Schiff base and is likely involved in directly influencing the photophysical properties of the GEVIs. Thus, in certain embodiments, the amino acid at position 60 is mutated to provide increased brightness. The inventive polypeptides herein have a red-shifted absorption and fluorescence spectrum, with minimal overlap with other reporters such as channelrhodopsin actuators and GFP-based reporters.

The starting sequences from which these inventive polypeptides can be engineered are based on archaerhodopsin protein or variant thereof. In certain embodiments, the voltage sensor is selected from an archaerhodopsin protein or variant thereof that provides a voltage-induced shift in its absorption or fluorescence.

Provided herein is a polypeptide comprising an amino acid sequence of wild-type archaerhodopsin 3 (SEQ ID NO: 1), wherein at least one of the amino acids at positions 60, 80, 95, 106, or 161 has been mutated. In certain embodiments, the polypeptide comprises an amino acid sequence of SEQ ID NO: 1, wherein at least two of the amino acids at positions 60, 80, 95, 106, or 161 have been mutated. In certain embodiments, the polypeptide comprises an amino acid sequence of SEQ ID NO: 1, wherein at least three of the amino acids at positions 60, 80, 95, 106, or 161 have been mutated. In certain embodiments, the polypeptide comprises an amino acid sequence of SEQ ID NO: 1, wherein at least four of the amino acids at positions 60, 80, 95, 106, or 161 have been mutated. In certain embodiments, the polypeptide comprises an amino acid sequence of SEQ ID NO: 1, wherein at the amino acids at positions 60, 80, 95, 106, or 161 have been mutated.

Provided herein is an polypeptide comprising an amino acid sequence of SEQ ID NO: 1, wherein the amino acid at position 60 is P or S, the amino acid at position 80 is T or S, the amino acid at position 95 is Asn, His, Gin, Cys, or Tyr, the amino acid at position 106 is Asn, Cys, Gin, Met, Ser, Thr, Asp, Glu, His or Lys, and the amino acid at position 161 is Phe or Val. Also provided herein are polynucleotides that encode the polypeptide.

In certain embodiments, the amino acids involved in proton translocation are mutated. Such mutations around the proton translocation network around the Schiff base could affect the voltage sensitivity, response kinetics, or other photophysical aspects of the GEVIs. In certain embodiments, the brightness of the GEVIs is improved relative to the wild-type protein. For example, amino acids at position 95 or position 106 of SEQ ID NO: 1 can be mutated. The amino acids corresponding to amino acids at position 95 or position 106 in another Archaerhodopsin or other microbial rhodopsins can also be similarly mutated.

In certain embodiments, the amino acid at position 60 is P. In certain embodiments, the amino acid at position 60 is S. In certain embodiments, the amino acid at position 80 is T. In certain embodiments, the amino acid at position 80 is S. In certain embodiments, the amino acid at position 95 is Asn, His, Gin, Cys, or Tyr. In certain embodiments, the amino acid at position 95 is Asn, Gin, or Cys. In certain embodiments, a Asn, Gin, or Cys at position 95 improves the voltage sensitivity. In certain embodiments, the amino acid at position 95 is Asn. In certain embodiments, the amino acid at position 95 is His. In certain embodiments, the amino acid at position 95 is Gin. In certain embodiments, the amino acid at position 95 is Cys. In certain embodiments, the amino acid at position 95 is Tyr. In certain embodiments, the amino acid at position 106 is Asn. In certain embodiments, the amino acid at position 106 is Cys. In certain embodiments, the amino acid at position 106 is Gin. In certain embodiments, the amino acid at position 106 is Met. In certain embodiments, the amino acid at position 106 is Ser. In certain embodiments, the amino acid at position 106 is Thr. In certain embodiments, the amino acid at position 106 is Asp. In certain embodiments, the amino acid at position 106 is Glu. In certain embodiments, the amino acid at position 106 is His. In certain embodiments, His at position 106 improves the voltage sensitivity and fast kinetics. In certain embodiments, the amino acid at position 106 is Lys. In certain embodiments, the amino acid at position 95 is His and the amino acid at position 106 is His. In certain embodiments, the amino acid at position 95 is Gin and the amino acid at position 106 is His. In certain embodiments, the amino acid at position 95 is either His or Gin.

Mutations that eliminate ion pumping in the inventive polypeptides generally comprise mutations to the Schiff base counterion, specifically a carboxylic amino acid (Asp) conserved on the third transmembrane helix (helix C) of archaerhodopsin. The amino acid sequence is RYX(DE) where X is a non-conserved amino acid. Mutations of the carboxylic amino acid directly affect the proton conduction pathway, eliminating the proton pumping property of the archaerhodopsin. The conserved Asp is located at position 95 of the Arch 3 amino acid sequence or variants thereof. Polypeptide variants that are at least about 80% homologous or at least about 80% identical to the polypeptides herein are contemplated to be within the scope of the invention. Thus, for polypeptide variants wherein the conserved Asp is not located at position 95 due to, for example, additions or deletions in the amino acid sequence, one of ordinary skill in the art would understand that the Asp in the polypeptide variant to be mutated for purposes of eliminating proton pumping is the Asp in the polypeptide variant that corresponds to the conserved Asp95 of the wild-type Arch 3.

To eliminate proton pumping, the conserved Asp is typically mutated to Asn or Gin, although other mutations are possible such as to a His. In certain embodiments, the inventive polypeptide comprises the substitution of the conserved Asp to Asn, Gin, or His in the Arch 3 amino acid sequence. In certain embodiments, the conserved Asp is located at position 95 of the Arch 3 amino acid sequence. In certain embodiments, the inventive polypeptide comprises the substitution of the conserved Asp to Asn in the Arch 3 amino acid sequence. In certain embodiments, the conserved Asp is located at position 95 of the Arch 3 amino acid sequence. In certain embodiments, the inventive polypeptide comprises the substitution of the conserved Asp to Gin in the Arch 3 amino acid sequence. In certain embodiments, the conserved Asp is located at position 95 of the Arch 3 amino acid sequence in the Arch 3 amino acid sequence. In certain embodiments, the inventive polypeptide comprises the substitution of the conserved Asp to His in the Arch 3 amino acid sequence. In certain embodiments, the conserved Asp is located at position 95 of the Arch 3 amino acid sequence. In certain embodiments, the inventive polypeptide comprises substitution of the conserved Asp to Cys in the Arch 3 amino acid sequence. In certain embodiments, the conserved Asp is located at position 95 of the Arch 3 amino acid sequence.

In certain embodiments, the polypeptide comprises an amino acid sequence of SEQ ID NO: 1, wherein the amino acid sequence comprises a mutation at position 95, resulting in the polypeptide having reduced ion pumping activity compared to a wild type member of the archaerhodopsin family of proteins from which it is derived. In certain embodiments, the amino acid at position 95 is mutated from a Asp to His, Gln, Cys, or Asn. In certain embodiments, the amino acid at position 95 is mutated from a Asp to Gln, Cys or Asn. In certain embodiments, the amino acid at position 95 is mutated from a Asp to Gin. In certain embodiments, the amino acid at position 95 is mutated from a Asp to Cys. In certain embodiments, the amino acid at position 95 is mutated from a Asp to Asn, wherein the polypeptide has an additional mutation as described herein. In certain embodiments where the amino acid at position 95 is mutated from a Asp to Asn, the polypeptide has at least one mutation at an amino acid residue selected from positions 60, 80, 106, and 161.

Provided herein are also polypeptides based on the amino acid sequence of wild-type archaerhodopsin 3. In certain embodiments, the polypeptide comprises an amino acid sequence of wild-type archaerhodopsin 3 (SEQ ID NO: 1), wherein the amino acid sequence for the polypeptide comprises at least one mutation selected from P60S, T80S, D95H, D106H, and F161V. In certain embodiments, the amino acid sequence for the polypeptide comprises at least two mutations selected from P60S, T80S, D95H, D106H, and F161V. In certain embodiments, the amino acid sequence for the polypeptide comprises at least three mutations selected from P60S, T80S, D95H, D106H, and F161V. In certain embodiments, the amino acid sequence for the polypeptide comprises at least four mutations selected from P60S, T80S, D95H, D106H, and F161V. In certain embodiments, the amino acid sequence for the polypeptide comprises at least five mutations selected from P60S, T80S, D95H, D106H, and F161V. In certain embodiments, the polypeptide comprises an amino acid sequence of SEQ ID NO: 2.

In certain embodiments, the polypeptide comprises an amino acid sequence of wild-type archaerhodopsin 3 (SEQ ID NO: 1), wherein the amino acid sequence for the polypeptides comprises at least one mutation selected from P60S, T80S, D95Q, D106H, and F161V. In certain embodiments, the polypeptide comprises an amino acid sequence of SEQ ID NO: 1 comprising at least two mutations selected from P60S, T80S, D95Q, D106H, and F161V. In certain embodiments, the polypeptide comprises an amino acid sequence of SEQ ID NO: 1 comprising at least three mutations selected from P60S, T80S, D95Q, D106H, and F161V. In certain embodiments, the polypeptide comprises an amino acid sequence of SEQ ID NO: 1 comprising at least four mutations selected from P60S, T80S, D95Q, D106H, and F161V. In certain embodiments, the polypeptide comprises an amino acid sequence of SEQ ID NO: 1 comprising the P60S, T80S, D95Q, D106H, and F161V mutations. In certain embodiments, the polypeptide comprises an amino acid sequence of SEQ ID NO: 3.

In certain embodiments, the polypeptide comprises an amino acid sequence of SEQ ID NO: 1, wherein the amino acid sequence comprises a mutation at position 95, and at least one mutation selected from P60S, T80S, D106H, and F161V. In certain embodiments, the polypeptide comprises an amino acid sequence of SEQ ID NO: 1, wherein the amino acid sequence comprises a mutation at position 95, and at least two mutations selected from P60S, T80S, D106H, and F161V. In certain embodiments, the polypeptide comprises an amino acid sequence of SEQ ID NO: 1, wherein the amino acid sequence comprises a mutation at position 95 and least three mutations selected from P60S, T80S, D106H, and F161V. In certain embodiments, the polypeptide comprises an amino acid sequence of SEQ ID NO: 1, wherein the amino acid sequence comprises a mutation at position 95 and the P60S, T80S, D106H, and F161V mutations.

In certain embodiments, the polypeptide comprises an amino acid sequence of SEQ ID NO: 1, wherein the amino acid sequence comprises a mutation at position 106 to a polar or charged amino acid. In certain embodiments, the polypeptide comprises an amino acid sequence of SEQ ID NO: 1, wherein the amino acid sequence comprises a mutation at position 106 to a polar amino acid selected from Asn, Cys, Gln, Met, Ser, and Thr. In certain embodiments, the polypeptide comprises an amino acid sequence of SEQ ID NO: 1, wherein the amino acid sequence comprises a mutation at position 106 to a charged amino acid selected from Asp and Glu. In certain embodiments, the polypeptide comprises an amino acid sequence of SEQ ID NO: 1, wherein the amino acid sequence comprises a mutation at position 106 to a charged amino acid selected from Arg, His, and Lys. In certain embodiments, the polypeptide comprises an amino acid sequence of SEQ ID NO: 1, wherein the amino acid sequence comprises a mutation at position 106 to His.

In certain embodiments, the polypeptide comprises an amino acid sequence of SEQ ID NO: 1, wherein the amino acid sequence comprises a mutation at position 106, and at least one mutation selected from P60S, T80S, D95(N/H/Q/C), and F161V. In certain embodiments, the polypeptide comprises an amino acid sequence of SEQ ID NO: 1, wherein the amino acid sequence comprises a mutation at position 106 and a mutation at position 60. In certain embodiments, position 106 is mutated to His. In certain embodiments, the polypeptide comprises an amino acid sequence of SEQ ID NO: 1, wherein the amino acid sequence comprises a mutation at position 106, and at least two mutations selected from P60S, T80S, D95(N/H/Q/C), and F161V. In certain embodiments, position 106 is mutated to His. In certain embodiments, the polypeptide comprises an amino acid sequence of SEQ ID NO: 1, wherein the amino acid sequence comprises a mutation at position 106, and at least three mutation selected from P60S, T80S, D95(N/H/Q/C), and F161V. In certain embodiments, position 106 is mutated to His. In certain embodiments, the polypeptide comprises an amino acid sequence of SEQ ID NO: 1, wherein the amino acid sequence comprises a mutation at position 106 and the P60S, T80S, D106H, and F161V mutations. In certain embodiments, position 106 is mutated to His.

In certain embodiments, the polypeptide comprises an amino acid sequence of SEQ ID NO: 1, wherein the amino acid sequence comprises a mutation at position 95, a mutation at position 106, and at least one mutation selected from P60S, T80S, and F161V. In certain embodiments, the polypeptide comprises an amino acid sequence of SEQ ID NO: 1, wherein the amino acid sequence comprises a mutation at position 95, a mutation at position 106, and least two mutations selected from P60S, T80S, and F161V. In certain embodiments, the polypeptide comprises an amino acid sequence of SEQ ID NO: 1, wherein the amino acid sequence comprises a mutation at position 95, a mutation at position 106, and the P60S, T80S, or F161V mutations. In certain embodiments, the amino acid at position 95 is mutated to Asn, His, Gln, Cys, or Tyr. In certain embodiments, the amino acid at position 95 is mutated to Asn, Gln, or Cys. In certain embodiments, the amino acid at position 95 is mutated to His. In certain embodiments, the amino acid at position 95 is mutated to Gln. In certain embodiments, the amino acid at position 106 is mutated to His or Tyr. In certain embodiments, the amino acid at position 106 is mutated to His. In certain embodiments, the amino acid at position 106 is mutated to Tyr.

In certain embodiments, the polypeptide comprising an amino acid sequence of SEQ ID NO: 1, wherein the amino acid sequence comprises a mutation at position 106 and least one mutation selected from P60S, T80S, and F161V. In certain embodiments, the polypeptide comprising an amino acid sequence of SEQ ID NO: 1, wherein the amino acid sequence comprises a mutation at position 106 and least two mutation selected from P60S, T80S, and F161V. In certain embodiments, the polypeptide comprising an amino acid sequence of SEQ ID NO: 1, wherein the amino acid sequence comprises a mutation at position 106 and the P60S, T80S, and F161V mutations. In certain embodiments, the amino acid at position 106 is mutated to His or Tyr. In certain embodiments, the amino acid at position 106 is mutated to His. In certain embodiments, the amino acid at position 106 is mutated to Tyr. In certain embodiments, the polypeptide comprising an amino acid sequence of SEQ ID NO: 1, wherein the amino acid sequence comprises a His at position 106 and least one mutation selected from P60S, T80S, and F161V.

In certain embodiments, the polypeptide comprises an amino acid sequence of SEQ ID NO: 1, wherein the amino acid sequence comprises a mutation at position 95, a mutation at position 106, and a mutation at position 60. In certain embodiments, the polypeptide comprises an amino acid sequence of SEQ ID NO: 1, wherein the amino acid sequence comprises a mutation at position 95, a mutation at position 106, a mutation at position 60, and least one mutation from T80S or F161V. In certain embodiments, the polypeptide comprises an amino acid sequence of SEQ ID NO: 1, wherein the amino acid sequence comprises a mutation at position 95, a mutation at position 106, a mutation at position 60, and the T80S or F161V mutations. In certain embodiments, the amino acid at position 95 is His, the amino acid at position 106 is His, and the amino acid at position 60 is Ser.

Provided herein is a polypeptide comprising an amino acid sequence of SEQ ID NO: 2. SEQ ID NO: 2 differs from the sequence of the wild-type Arch 3 with respect to the following mutations: P60S, T80S, D95H, D106H, and F161V. Also contemplated is a polypeptide variant of SEQ ID NO: 2 comprising the P60S, T80S, D95H, D106H, and F161V mutations but comprises an alteration, i.e., a substitution, insertion, and/or deletion, at one or more other positions of the polypeptide. Polypeptides that are homologous to SEQ ID NO: 2 are also contemplated.

In certain embodiments, the polypeptide comprises a sequence that is at least about 80% homologous to the amino acid sequence of SEQ ID NO: 2. In certain embodiments, the polypeptide comprises a sequence that is at least about 85% homologous to the amino acid sequence of SEQ ID NO: 2. In certain embodiments, the polypeptide comprises a sequence that is at least about 90% homologous to the amino acid sequence of SEQ ID NO: 2. In certain embodiments, the polypeptide comprises a sequence that is at least about 95% homologous to the amino acid sequence of SEQ ID NO: 2. In certain embodiments, the polypeptide comprises a sequence that is at least about 96% homologous to the amino acid sequence of SEQ ID NO: 2. In certain embodiments, the polypeptide comprises a sequence that is at least about 97% homologous to the amino acid sequence of SEQ ID NO: 2. In certain embodiments, the polypeptide comprises a sequence that is at least about 98% homologous to the amino acid sequence of SEQ ID NO: 2. In certain embodiments, the polypeptide comprises a sequence that is at least about 99% homologous to the amino acid sequence of SEQ ID NO: 2. In certain embodiments, the polypeptide comprises a sequence that is at least about 80%, at least about 85%, at least about 90%, at least about 95%, at least about 96%, at least about 97%, at least about 98%, or at least about 99% homologous to the amino acid sequence of SEQ ID NO: 2.

In certain embodiments, the polypeptide comprises a sequence that is at least about 80% identical to the amino acid sequence of SEQ ID NO: 2. In certain embodiments, the polypeptide comprises a sequence that is at least about 85% identical to the amino acid sequence of SEQ ID NO: 2. In certain embodiments, the polypeptide comprises a sequence that is at least about 90% identical to the amino acid sequence of SEQ ID NO: 2. In certain embodiments, the polypeptide comprises a sequence that is at least about 95% identical to the amino acid sequence of SEQ ID NO: 2. In certain embodiments, the polypeptide comprises a sequence that is at least about 96% identical to the amino acid sequence of SEQ ID NO: 2. In certain embodiments, the polypeptide comprises a sequence that is at least about 97% identical to the amino acid sequence of SEQ ID NO: 2. In certain embodiments, the polypeptide comprises a sequence that is at least about 98% identical to the amino acid sequence of SEQ ID NO: 2. In certain embodiments, the polypeptide comprises a sequence that is at least about 99% identical to the amino acid sequence of SEQ ID NO: 2. In certain embodiments, the polypeptide comprises a sequence that is at least about 80%, at least about 85%, at least about 90%, at least about 95%, at least about 96%, at least about 97%, at least about 98%, or at least about 99% identical to the amino acid sequence of SEQ ID NO: 2.

Provided herein is a polypeptide comprising an amino acid sequence of SEQ ID NO: 3. SEQ ID NO: 3 differs from the sequence of the wild-type Arch 3 with respect to the following mutations: P60S, T80S, D95Q, D106H, and F161V. Also contemplated is a polypeptide variant of SEQ ID NO: 3 comprising the P60S, T80S, D95Q, D106H, and F161V mutations but comprises an alteration, i.e., a substitution, insertion, and/or deletion, at one or more other positions of the polypeptide. Polypeptides that are homologous to SEQ ID NO: 3 are also contemplated.

In certain embodiments, the polypeptide comprises a sequence that is at least about 80% homologous to the amino acid sequence of SEQ ID NO: 3. In certain embodiments, the polypeptide comprises a sequence that is at least about 85% homologous to the amino acid sequence of SEQ ID NO: 3. In certain embodiments, the polypeptide comprises a sequence that is at least about 90% homologous to the amino acid sequence of SEQ ID NO: 3. In certain embodiments, the polypeptide comprises a sequence that is at least about 95% homologous to the amino acid sequence of SEQ ID NO: 3. In certain embodiments, the polypeptide comprises a sequence that is at least about 96% homologous to the amino acid sequence of SEQ ID NO: 3. In certain embodiments, the polypeptide comprises a sequence that is at least about 97% homologous to the amino acid sequence of SEQ ID NO: 3. In certain embodiments, the polypeptide comprises a sequence that is at least about 98% homologous to the amino acid sequence of SEQ ID NO: 3. In certain embodiments, the polypeptide comprises a sequence that is at least about 99% homologous to the amino acid sequence of SEQ ID NO: 3. In certain embodiments, the polypeptide comprises a sequence that is at least about 80%, at least about 85%, at least about 90%, at least about 95%, at least about 96%, at least about 97%, at least about 98%, or at least about 99% homologous to the amino acid sequence of SEQ ID NO: 3.

In certain embodiments, the polypeptides comprise a sequence that is at least about 80% identical to the amino acid sequence of SEQ ID NO: 3. In certain embodiments, the polypeptide comprises a sequence that is at least about 85% identical to the amino acid sequence of SEQ ID NO: 3. In certain embodiments, the polypeptide comprises a sequence that is at least about 90% identical to the amino acid sequence of SEQ ID NO: 3. In certain embodiments, the polypeptide comprises a sequence that is at least about 95% identical to the amino acid sequence of SEQ ID NO: 3. In certain embodiments, the polypeptide comprises a sequence that is at least about 96% identical to the amino acid sequence of SEQ ID NO: 3. In certain embodiments, the polypeptide comprises a sequence that is at least about 97% identical to the amino acid sequence of SEQ ID NO: 3. In certain embodiments, the polypeptide comprises a sequence that is at least about 98% identical to the amino acid sequence of SEQ ID NO: 3. In certain embodiments, the polypeptide comprises a sequence that is at least about 99% identical to the amino acid sequence of SEQ ID NO: 3. In certain embodiments, the polypeptide comprises a sequence that is at least about 80%, at least about 85%, at least about 90%, at least about 95%, at least about 96%, at least about 97%, at least about 98%, or at least about 99% identical to the amino acid sequence of SEQ ID NO: 3.

In certain embodiments, the polypeptides are encoded by a nucleic acid sequence that is at least about 80% identical to the nucleic acid sequence of SEQ ID NO: 5. In certain embodiments, the polypeptides are encoded by a nucleic acid sequence that is at least about 85% identical to the nucleic acid sequence of SEQ ID NO: 5. In certain embodiments, the polypeptides are encoded by a nucleic acid sequence that is at least about 90% identical to the nucleic acid sequence of SEQ ID NO: 5. In certain embodiments, the polypeptides are encoded by a nucleic acid sequence that is at least about 95% identical to the nucleic acid sequence of SEQ ID NO: 5. In certain embodiments, the polypeptides are encoded by a nucleic acid sequence that is at least about 96% identical to the nucleic acid sequence of SEQ ID NO: 5. In certain embodiments, the polypeptides are encoded by a nucleic acid sequence that is at least about 97% identical to the nucleic acid sequence of SEQ ID NO: 5. In certain embodiments, the polypeptides are encoded by a nucleic acid sequence that is at least about 98% identical to the nucleic acid sequence of SEQ ID NO: 5. In certain embodiments, the polypeptides are encoded by a nucleic acid sequence that is at least about 99% identical to the nucleic acid sequence of SEQ ID NO: 5. In certain embodiments, the polypeptides are encoded by a nucleic acid sequence that is at least about 80%, at least about 85%, at least about 90%, at least about 95%, at least about 96%, at least about 97%, at least about 98%, or at least about 99% identical to the nucleic acid sequence of SEQ ID NO: 5.

In certain embodiments, the polypeptides are encoded by a nucleic acid sequence that is at least about 80% identical to the nucleic acid sequence of SEQ ID NO: 6. In certain embodiments, the polypeptides are encoded by a nucleic acid sequence that is at least about 85% identical to the nucleic acid sequence of SEQ ID NO: 6. In certain embodiments, the polypeptides are encoded by a nucleic acid sequence that is at least about 90% identical to the nucleic acid sequence of SEQ ID NO: 6. In certain embodiments, the polypeptides are encoded by a nucleic acid sequence that is at least about 95% identical to the nucleic acid sequence of SEQ ID NO: 6. In certain embodiments, the polypeptides are encoded by a nucleic acid sequence that is at least about 96% identical to the nucleic acid sequence of SEQ ID NO: 6. In certain embodiments, the polypeptides are encoded by a nucleic acid sequence that is at least about 97% identical to the nucleic acid sequence of SEQ ID NO: 6. In certain embodiments, the polypeptides are encoded by a nucleic acid sequence that is at least about 98% identical to the nucleic acid sequence of SEQ ID NO: 6. In certain embodiments, the polypeptides are encoded by a nucleic acid sequence that is at least about 99% identical to the nucleic acid sequence of SEQ ID NO: 6. In certain embodiments, the polypeptides are encoded by a nucleic acid sequence that is at least about 80%, at least about 85%, at least about 90%, at least about 95%, at least about 96%, at least about 97%, at least about 98%, or at least about 99% identical to the nucleic acid sequence of SEQ ID NO: 6.

Also contemplated are nucleic acid sequences that are homologous to the nucleic acid sequence of SEQ ID NO: 5 or SEQ ID NO: 6. Two nucleotide sequences are considered to be homologous if the polypeptides they encode are at least about 50% identical, at least about 60% identical, at least about 70% identical, at least about 80% identical, at least about 90% identical, or at least about 95% identical for at least one stretch of at least 20 amino acids. Generally, homologous nucleotide sequences are also characterized by the ability to encode a stretch of at least 4-5 uniquely specified amino acids. Both the identity and the approximate spacing of these amino acids relative to one another are considered for nucleotide sequences to be considered homologous. For example, nucleotide sequences less than 60 nucleotides in length, homology is determined by the ability to encode a stretch of at least about 4-5 uniquely specified amino acids.

In certain embodiments, the polypeptides provided herein have deletions, substitutions, and/or additions of 1 to 25 amino acids. In certain embodiments, the polypeptides provided herein have deletions, substitutions, and/or additions of 1 to 5 amino acids. In certain embodiments, the polypeptides provided herein have deletions, substitutions, and/or additions of 5 to 10 amino acids. In certain embodiments, the polypeptides provided herein have deletions, substitutions, and/or additions of 10 to 15 amino acids. In certain embodiments, the polypeptides provided herein have deletions, substitutions, and/or additions of 15 to 20 amino acids. In certain embodiments, the polypeptides provided herein have deletions, substitutions, and/or additions of 20 to 25 amino acids.

Provided herein are polynucleotides encoding any inventive polypeptide provided herein. Also provided herein are polynucleotides encoding a polypeptide comprising an amino acid sequence of SEQ ID NO: 2 or variant thereof. Further provided herein are polynucleotides encoding a polypeptide comprising an amino acid sequence of SEQ ID NO: 3 or variant thereof.

With respect to polynucleotide sequences herein, degeneracy of the genetic code provides the possibility to substitute at least one base of the base sequence of a gene with a different base without causing the amino acid sequence of the polypeptide produced from the gene to be changed. Hence, the polynucleotides of the present invention may also have any base sequence that has been changed from a sequence recited herein, e.g., in Table 2, by substitution in accordance with degeneracy of genetic code. References describing codon usage include Carels et al. (1998) *J. Mol. Evol.*, 46:45 and Fennoy et al. (1993) *Nuci. Acids Res.* 21(23):5294.

Provided herein are polynucleotide comprising an nucleic acid sequence of SEQ ID NO: 4, or complement thereof, wherein the nucleic acid sequence encodes a polypeptide with at least one mutation selected from positions 60, 80, 95, 106, and 161. In certain embodiments, the polynucleotide comprising an nucleic acid sequence of SEQ ID NO: 4, wherein the nucleic acid sequence encodes a polypeptide with at least two mutations selected from positions 60, 80, 95, 106, and 161. In certain embodiments, the polynucleotide comprising an nucleic acid sequence of SEQ ID NO: 4, wherein the nucleic acid sequence encodes a polypeptide with at least three mutations selected from positions 60, 80, 95, 106, and 161. In certain embodiments, the polynucleotide comprising an nucleic acid sequence of SEQ ID NO: 4, wherein the nucleic acid sequence encodes a polypeptide with at least four mutations selected from positions 60, 80, 95, 106, and 161. In certain embodiments, the polynucleotide comprising an nucleic acid sequence of SEQ ID NO: 4, wherein the nucleic acid sequence encodes a polypeptide with mutations at positions 60, 80, 95, 106, and 161.

In certain embodiments, the polynucleotide comprises an nucleic acid sequence of SEQ ID NO: 4, or the complement thereof, wherein the nucleic acid sequence encodes a polypeptide with at least one mutations selected from P60S, T80S, D95(H/Q), D106H, and F161V. In certain embodiments, the polynucleotide comprises a nucleic acid sequence of SEQ ID NO: 4, wherein the nucleic acid sequence encodes a polypeptide with at least two mutations selected from P60S, T80S, D95(H/Q), D106H, and F161V. In certain embodiments, the polynucleotide comprises an nucleic acid sequence of SEQ ID NO: 4, wherein the nucleic acid sequence encodes a polypeptide with at least three mutations selected from P60S, T80S, D95(H/Q), D106H, and F161V. In certain embodiments, the polynucleotide comprises an nucleic acid sequence of SEQ ID NO: 4, wherein the nucleic acid sequence encodes a polypeptide with at least four mutations selected from P60S, T80S, D95(H/Q), D106H, and F161V. In certain embodiments, the polynucleotide comprises a nucleic acid sequence of SEQ ID NO: 4, wherein the nucleic acid sequence encodes a polypeptide with the mutations P60S, T80S, D95H, D106H, and F161V. In certain embodiments, the polynucleotide comprises a nucleic acid sequence of SEQ ID NO: 4, wherein the nucleic acid sequence encodes a polypeptide with the mutations P60S, T80S, D95Q, D106H, and F161V.

Provided herein are polynucleotides comprising a nucleic acid sequence of SEQ ID NO: 5, or the complement thereof. In certain embodiments, polynucleotides comprises a nucleic acid sequence that is at least about 80% identical to the nucleic acid sequence of SEQ ID NO: 5. In certain embodiments, polynucleotides comprises a nucleic acid sequence that is at least about 85% identical to the nucleic acid sequence of SEQ ID NO: 5. In certain embodiments, polynucleotides comprises a nucleic acid sequence that is at least about 90% identical to the nucleic acid sequence of SEQ ID NO: 5. In certain embodiments, polynucleotides comprises a nucleic acid sequence that is at least about 95% identical to the nucleic acid sequence of SEQ ID NO: 5. In certain embodiments, polynucleotides comprises a nucleic acid sequence that is at least about 97% identical to the nucleic acid sequence of SEQ ID NO: 5. In certain embodiments, polynucleotides comprises a nucleic acid sequence that is at least about 98% identical to the nucleic acid sequence of SEQ ID NO: 5. In certain embodiments, polynucleotides comprises a nucleic acid sequence that is at least about 80%, at least about 85%, at least about 90%, at least about 95%, at least about 97%, at least about 98%, or at least about 99% identical to the nucleic acid sequence of SEQ ID NO: 5.

Provided herein are polynucleotides comprising a nucleic acid sequence of SEQ ID NO: 6, or the complement thereof. In certain embodiments, polynucleotides comprises a nucleic acid sequence that is at least about 80% identical to the nucleic acid sequence of SEQ ID NO: 6. In certain embodiments, polynucleotides comprises a nucleic acid sequence that is at least about 85% identical to the nucleic acid sequence of SEQ ID NO: 6. In certain embodiments, polynucleotides comprises a nucleic acid sequence that is at least about 90% identical to the nucleic acid sequence of SEQ ID NO: 6. In certain embodiments, polynucleotides comprises a nucleic acid sequence that is at least about 95% identical to the nucleic acid sequence of SEQ ID NO: 6. In certain embodiments, polynucleotides comprises a nucleic acid sequence that is at least about 97% identical to the nucleic acid sequence of SEQ ID NO: 6. In certain embodiments, polynucleotides comprises a nucleic acid sequence that is at least about 98% identical to the nucleic acid sequence of SEQ ID NO: 6. In certain embodiments, polynucleotides comprises a nucleic acid sequence that is at least about 80%, at least about 85%, at least about 90%, at least about 95%, at least about 97%, at least about 98%, or at least about 99% identical to the nucleic acid sequence of SEQ ID NO: 6.

Properties of the Inventive Polypeptides

The inventive polypeptides provided herein are fluorescent with reduced ion pumping activity compared to a natural member of the archaerhodopsin family of proteins from which it is derived. In certain embodiments, the polypeptide of any one of the preceding claims, wherein the polypeptide is activated by contact with light having a non-blue light wavelength. In certain embodiments, the polypeptide is activated by contact with at least one or all of yellow light, orange, or red light. In certain embodiments, the polypeptide is minimally activated or not at all activated by contact with blue light. In certain embodiments, the polypeptide is activated by contact with red light having a wavelength of at least about 590 nm. In certain embodiments, the polypeptide is activated by contact with red light having a wavelength of at least about 600 nm. In certain embodiments, the polypeptide is activated by contact with red light having a wavelength of at least about 620 nm. In certain embodiments, the polypeptide is activated by contact with red light having a wavelength of at least about 630 nm. In certain embodiments, the polypeptide is activated by contact with red light having a wavelength of at least about 640 nm. In certain embodiments, the polypeptide is activated by contact with red light having a wavelength of at least about 650 nm. In certain embodiments, the polypeptide is activated by contact with red light having a wavelength of about 600 nm to about 700 nm. In certain embodiments, the polypeptide is activated by contact with red light having a wavelength of about 620 nm to about 690 nm.

In certain embodiments, the polypeptide when contacted with blue light, the polypeptide is activated not at all, or at least less than 1%, 2%, 3%, 4%, 5%, 6%, 7%, 8%, 9%, 10%, 11%, 12, 13%, 14%, 15%, 16%, 17%, 18%, 19%, or 20% of the level of activation of the polypeptide when contacted with red light.

In certain embodiments, the inventive polypeptide does not distort the waveform of action potentials in various cells, for example, in mammalian neurons, skeletal myocytes, cardiac cells, glial cells, pancreatic beta cells, or in endothelial cell, for example in mammalian cardiomyocytes (e.g., human induced pluripotent stem cell (iPS)-derived cardiomyocytes). In certain embodiments, the inventive polypeptide does not distort the waveform of action potentials of neurons. In certain embodiments, the inventive polypeptide does not distort the waveform of action potentials of cardiac cells. In certain embodiments, the inventive polypeptide does not distort the waveform of action potentials of skeletal muscle cells. In certain embodiments, the inventive polypeptide does not distort the waveform of action potentials that rise and fall in greater than or equal to about 0.05 ms, greater than or equal to about 0.1 ms, greater than or equal to about 1 ms, greater than or equal to about 1.5 ms, greater than or equal to about 5 ms, greater than or equal to about 10 ms, or greater than or equal to about 12 ms. In certain embodiments, the inventive polypeptide does not distort the waveform of action potentials that rise and fall in greater than or equal to about 0.05 ms. In certain embodiments, the inventive polypeptide does not distort the waveform of action potentials that rise and fall in greater than or equal to about 0.1 ms. In certain embodiments, the inventive polypeptide does not distort the waveform of action potentials that rise and fall in greater than or equal to about 1 ms. In certain embodiments, the inventive polypeptide does not distort the waveform of action potentials that rise and fall in greater than or equal to about 1.5 ms. In certain embodiments, the inventive polypeptide does not distort the waveform of action potentials that rise and fall in greater than or equal to about 5 ms. In certain embodiments, the inventive polypeptide does not distort the waveform of action potentials that rise and fall in about 0.05 ms to 1.5 ms, or about 1.5 ms to 5 ms, or about 5 ms to 12 ms. For example, the fluorescence of QuasAr1 responds to a step in voltage in <0.05 ms, while QuasAr2 responds to a step in voltage in about 1.2 ms at room temperature. Thus QuasAr1 does not distort the waveform of action potentials that rise and fall in 0.1 ms, such as those occurring in fast-spiking interneurons; and QuasAr2 does not distort action potentials that occur in about 1 millisecond or longer, such as cardiac action potentials.

In certain embodiments, the polypeptide shows a change in fluorescence over the physiological voltage range of about −70 mV to about +30 mV. In certain embodiments, the polypeptide shows a change in fluorescence over the physiological voltage range of about −50 mV to about +30 mV. In certain embodiments, the polypeptide shows a change in fluorescence over the physiological voltage range of about −100 mV to about +50 mV. In certain embodiments, the polypeptide shows a change in fluorescence over the physiological voltage range of about −80 mV to about +50 mV. In certain embodiments, the polypeptide shows a change in fluorescence over the physiological voltage range of about −70 mV to about +30 mV. In certain embodiments, the polypeptide shows a change in fluorescence over the physiological voltage range of about −30 mV to about +30 mV. In certain embodiments, the polypeptide shows a change in fluorescence over the physiological voltage range of the subthreshold voltage dynamics in neurons. In certain embodiments, the polypeptide shows a change in fluorescence over the physiological voltage range of about −80 mV to about −40 mV. In certain embodiments, the polypeptide shows a change in fluorescence over the physiological voltage range of inhibitory and excitatory post-synaptic potentials. In certain embodiments, the polypeptide shows a change in fluorescence over the physiological voltage range of about −70 mV to about −50 mV. In certain embodiments, the change in flouorescence is large, e.g., at least about 20% per 100 mV, at least about 30% per 100 mV, is at least about 40% per 100 mV, is at least about 50% per 100 mV, is at least about 60% per 100 mV, is at least about 70% per 100 mV, is at least about 80% per 100 mV, or is at least about 90% per 100 mV. In certain embodiments, the change in flouorescence is large and approximately linear.

In certain embodiments, the inventive polypeptide exhibits a fluorescent quantum yield of about $1\times10^{-3}$ to about $30\times10^{-3}$. In certain embodiments, the inventive polypeptide exhibits a fluoresecent quantum yield of about $1\times10^{-3}$ to about $15\times10^{-3}$. In certain embodiments, the inventive polypeptide exhibits a fluorescent quantum yield of about $15\times10^{-3}$ to about $30\times10^{-3}$. In certain embodiments, the inventive polypeptide exhibits a fluoresecent quantum yield of about $3\times10^{-3}$ to about $5\times10^{-3}$. In certain embodiments, the inventive polypeptide exhibits a fluoresecent quantum yield of about $5\times10^{-3}$ to about $7\times10^{-3}$. In certain embodiments, the inventive polypeptide exhibits a fluoresecent quantum yield of about $7\times10^{-3}$ to about $9\times10^{-3}$. In certain embodiments, the inventive polypeptide exhibits a fluoresecent quantum yield of about $4\times10^{-3}$. In certain embodiments, the inventive polypeptide exhibit a fluoresecent quantum yield of about $8\times10^{-3}$.

In certain embodiments, the inventive polypeptide exhibits a fluoresecent quantum yield enhanced by about 10-fold to about 20-fold compared to Arch (D95N), which is described in US Patent Application No. 2013/0224756, incorporated herein by reference in its entirety. In certain embodiments, the inventive polypeptide exhibits a fluoresecent quantum yield enhanced by about 10-fold to about 15-fold compared to Arch (D95N). In certain embodiments, the inventive polypeptide exhibits a fluoresecent quantum yield enhanced by about 15-fold to about 20-fold compared to Arch (D95N). In certain embodiments, the inventive polypeptide exhibits a fluoresecent quantum yield enhanced by about 10-fold. In certain embodiments, the inventive polypeptide exhibits a fluoresecent quantum yield enhanced by about 19-fold.

In certain embodiments, the inventive polypeptide exhibits a fluoresecent quantum yield enhanced by about 2-fold to about 20-fold compared to wild-type Arch, when excited at at a wavelength of 640 nm and under an intensity of 500 mW/cm². In certain embodiments, the inventive polypeptide exhibits a fluoresecent quantum yield enhanced by about 3-fold to about 17-fold compared to wild-type Arch. In certain embodiments, the inventive polypeptide exhibits a fluoresecent quantum yield enhanced by about 3-fold to about 15-fold compared to wild-type Arch. In certain embodiments, the inventive polypeptide exhibits a fluoresecent quantum yield enhanced by about 2-fold to about 5-fold compared to wild-type Arch. In certain embodiments, the inventive polypeptide exhibits a fluoresecent quantum yield enhanced by about 13-fold to about 17-fold compared to wild-type Arch. In certain embodiments, the inventive polypeptide exhibits a fluoresecent quantum yield enhanced by about 3-fold to about 4-fold compared to wild-type Arch. In certain embodiments, the inventive polypeptide exhibits a fluoresecent quantum yield enhanced by about 15-fold compared to wild-type Arch.

In certain embodiments, the inventive polypeptide exhibits a fluoresecent quantum yield is enhanced by about 1.5-fold to about 5-fold compared to wild-type Arch when excited at at a wavelength of 640 nm and under an intensity of at least 100 W/cm². In certain embodiments, the inventive polypeptide exhibits a fluoresecent quantum yield enhanced by about 2-fold to about 3-fold compared to wild-type Arch. In certain embodiments, the inventive polypeptide exhibits a fluoresecent quantum yield enhanced by about 2.5-fold compared to wild-type Arch.

In certain embodiments, the inventive polypeptide exhibits a brightness that is linear with the illumination intensity.

In certain embodiments, the inventive polypeptide exhibits a sensitivity of about 1.25-fold to 2.5-fold higher than the sensitivity of Arch or Arch (D95N) between −100 mV and +50 mV. In certain embodiments, the inventive polypeptide exhibits a sensitivity of about 25% to about 100% per 100 mV. In certain embodiments, the inventive polypeptide exhibits a sensitivity of about 25% to about 35% per 100 mV. In certain embodiments, the inventive polypeptide exhibits a sensitivity of about 30% to about 40% per 100 mV. In certain embodiments, the inventive polypeptide exhibits a sensitivity of about 35% to about 50% per 100 mV. In certain embodiments, the inventive polypeptide exhibits a sensitivity of about 50% to about 70% per 100 mV. In certain embodiments, the inventive polypeptide exhibits a sensitivity of about 70% to about 100% per 100 mV. In certain embodiments, the inventive polypeptide exhibits a sensitivity of about 85% to about 95% per 100 mV. In certain embodiments, the inventive polypeptide exhibits a sensitivity of about 90% per 100 mV.

In certain embodiments, the inventive polypeptide has a step response time constant of less than about 41 ms when measured at room temperature. In certain embodiments, the inventive polypeptide has a step response time constant of less than about 15 ms when measured at room temperature. In certain embodiments, the inventive polypeptides has a step response time constant of less than about 6 ms when measured at room temperature. In certain embodiments, the inventive polypeptides has a step response time constant of less than about 1.5 ms when measured at room temperature. In certain embodiments, the inventive polypeptides has a step response time constant of less than about 1 ms when measured at room temperature. In certain embodiments, the inventive polypeptides has a step response time constant of less than about 0.6 ms when measured at room temperature. In certain embodiments, the inventive polypeptide has a step response time constant of about 0.1 ms to about 15 ms when measured at room temperature. In certain embodiments, the inventive polypeptides has a step response time constant of about 0.05 ms to about 0.6 ms when measured at room temperature. In certain embodiments, the inventive polypeptides has a step response time constant of about 0.3 ms when measured at about 34° C. In certain embodiments, the inventive polypeptides has a step response time constant that is mono-exponential. In certain embodiments, the inventive polypeptides has a step response time constant that is bi-exponential.

In certain embodiments, the inventive polypeptides has a photobleaching time constant of about 400 s to about 1200 s. In certain embodiments, the inventive polypeptides has a photobleaching time constant of about 400 s to about 500 s. In certain embodiments, the inventive polypeptides has a photobleaching time constant of about 900 s to about 1100 s.

The inventive polypeptides also show far red excitation spectrum, which means that the inventive polypeptides absorb wavelength in the red light end of the spectrum. In certain embodiments, the inventive polypeptides can be excited with light ranging from 600 nm to 690 nm light, and the emission is in the near infrared region, peaked at 750 nm. The emission is farther to the red than any existing fluorescent protein. These wavelengths coincide with low cellular autofluorescence and good transmission through tissue. This feature makes these proteins particularly useful in optical measurements of action potential as the spectrum facilitates imaging with high signal-to-noise, as well as multi-spectral imaging in combination with other fluorescent probes.

The GEVIs also exhibit high targetability. GEVIs can be imaged in primary neuronal cultures, cardiomyocytes (HL-1 and human iPSC-derived), HEK cells, and Gram positive and Gram negative bacteria. In certain embodiments, the GEVIs have been targeted to the endoplasmic reticulum and mitochondria. The GEVIs can be used for in vivo imaging in *C. elegans*, zebrafish, and mice.

With the microbial rhodopsin constructs of the invention further comprising a cell type- and/or a time-specific promotors, one can image membrane potential in any optically accessible cell type or organelle in a living organism.

In certain embodiments, an inventive polypeptides comprises, consists of, or consists essentially of at least three elements: a promoter, an inventive polypeptide, one or more targeting motifs, and an optional second fluorescent protein.

In certain embodiment, at least one element from each group of promoter, voltage indicator, and targeting motif are selected to create an VIP with the desired properties. A second polypeptide is optionally selected to create a fusion protein with the voltage indicators provided herein. In some embodiments, methods and compositions for voltage sensing as described herein involves selecting: 1) an archaerhodopsin protein or variant thereof; 2) one or more mutations to imbue the protein with sensitivity to voltage or to other quantities of interest (e.g., increased brightness) and to eliminate light-driven charge pumping; 3) codon usage appropriate to the host species; 4) a promoter and targeting sequences to express the protein in cell types of interest and to target the protein to the sub-cellular structure of interest; 5) an optional fusion with a second fluorescent protein to provide ratiometric imaging; 6) a chromophore comprising, e.g., retinal, dimethylamino retinal, or 3,4 dehydro retinal, to optionally insert into the archaerhodopsin protein or variant thereof; and 7) an optical imaging scheme.

Fusion Proteins and FRET Pairs

The inventive polypeptides are termed genetically encoded voltage indicators (GEVIs). Provide herein are GEVIs with improved brightness, that function through electrochromic fluorescence resonance energy transfer (eFRET) between an appended fluorescent protein and the Archaerhodopsin-based chromophore, retinal (i.e., a FRET pair).

Figure 6:
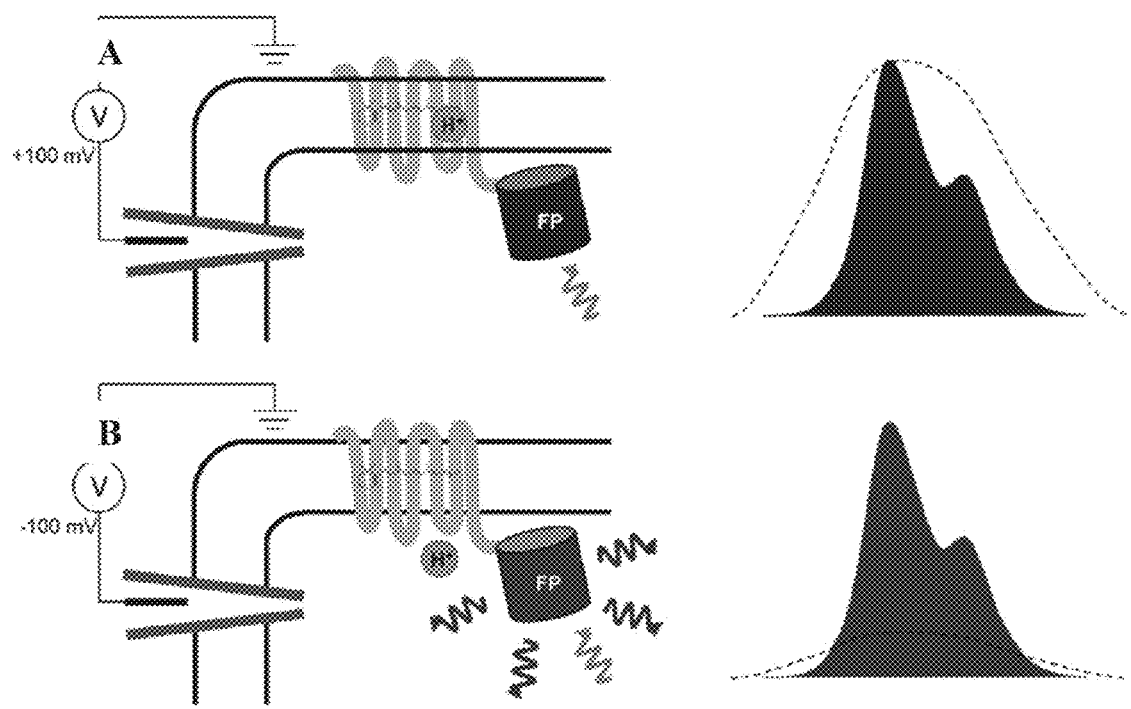
FIG. 6 shows the mechanism of voltage-dependent fluorescence in eFRET-based voltage indicators. Images to the left show cartoons of the protein structure in a cell plasma membrane. Images to the right show the voltage-dependent absorption spectrum of the microbial rhodopsin (dashed line) and emission spectrum of the attached fluorescent protein.
Figure 8A:
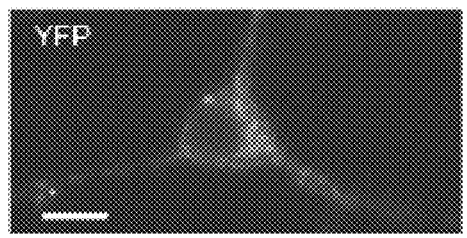
FIGS. 8A-8C show single-trial detection of neuronal action potentials with three eFRET GEVIs.
Figure 8A:
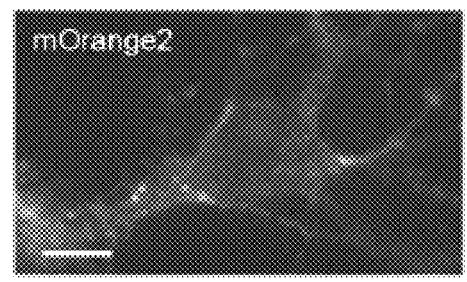
Figure 8A:
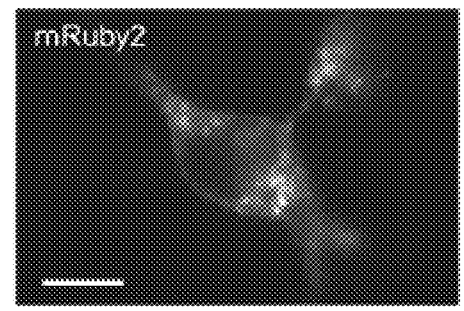
Figure 8B:
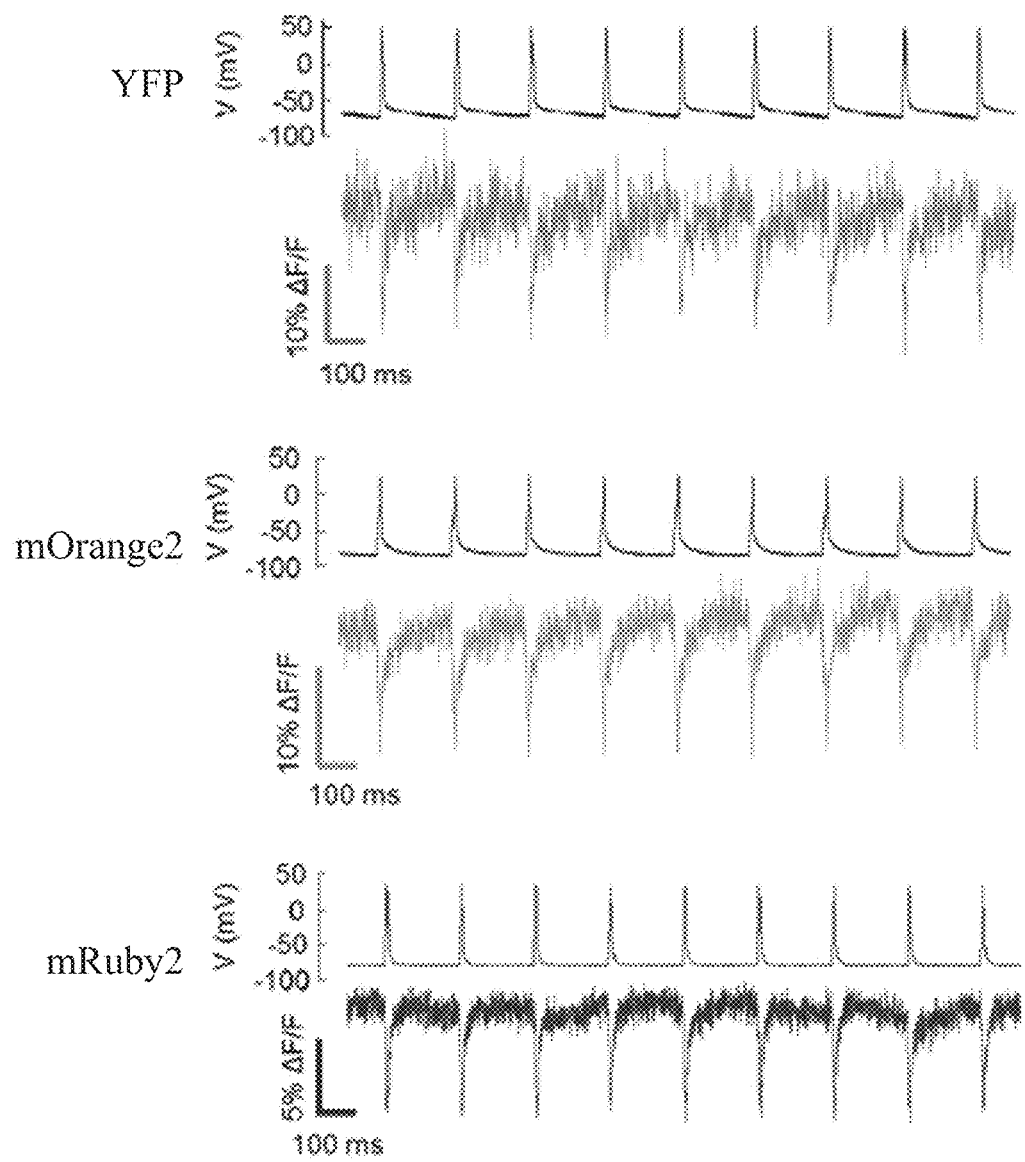
Figure 8C:
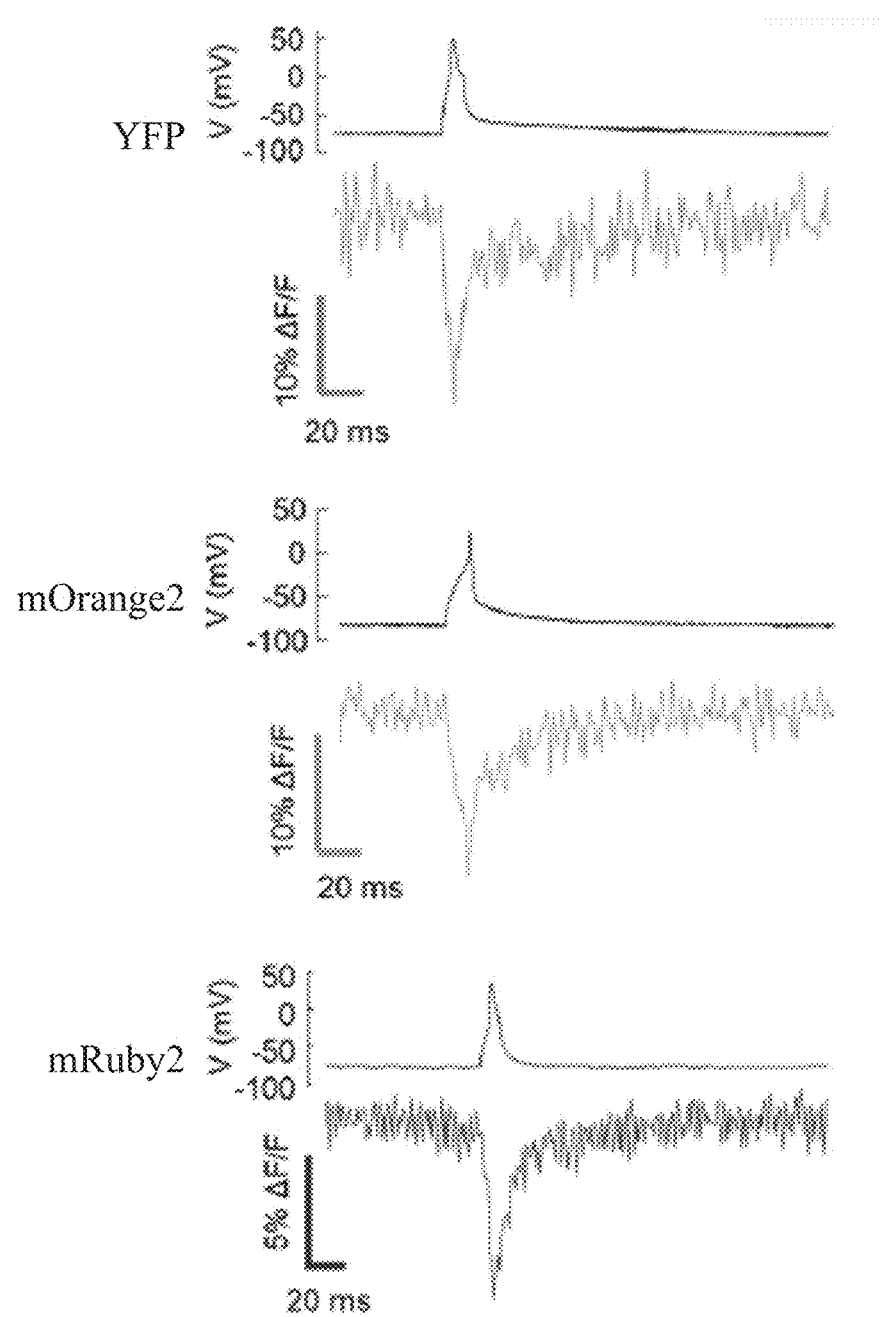

These eFRET-based GEVIs have enhanced brightness and comparable speed relative to the direct fluorescence of the individual GEVIs. In eFRET, the electronic shifts of an acceptor polypeptide can be used to alter the degree of spectral overlap between the emission of the donor polypeptide and the absorption of the acceptor polypeptide, thereby altering the degree of nonradiative quenching of an acceptor polypeptide by the donor polypeptide. For example, the more overlap between the donor emission spectrum with the acceptor absorption spectrum means a higher efficiency of donor fluorescence quenching by the acceptor. The less overlap between the donor emission spectrum with the acceptor absorption spectrum means a lower efficiency of donor fluorescence quenching by the acceptor. FIG. 6 generally illustrates eFRET-based voltage indicators. In the FRET pairs provided herein, the GEVIs are the electrochromic quencher, which exhibit changes in absorbance in response to changes in membrane voltage due (voltage-dependent absorption). Voltage-dependent changes in the absorption spectrum of the GEVI's retinal chromophore lead to voltage-dependent rates of nonradiative FRET between a fluorescent protein and the retinal. Retinal in its absorbing, fluorescent (protonated) state quenches the GFP, while retinal in the non-absorbing, non-fluorescent state does not quench the GFP. The fluorescence of a donor polypeptide would be decreased or increased depending on how weakly or strongly the acceptor polypeptide absorbs the fluorescence of a donor polypeptide, which is dependent on the spectral overlap. It has been observed that membrane voltage changes the fluorescence of the GEVIs provided herein. In view of this observation, the fluorescence changes of the GEVIs are a result of changes in its absorbance spectrum, and therefore, the GEVIs are useful for voltage-dependent quenching of a second fluorescent protein appended to a GEVI.

Provided herein are fusion proteins comprising the inventive polypeptides described herein (i.e., the GEVIs). In certain embodiments, the fusion proteins comprises the inventive polypeptide or variant thereof provided herein and a second polypeptide. In certain embodiments, the second polypeptide is a fluorescent polypeptide or homologues thereof. In certain embodiments, the fusion proteins form an electrochromic FRET pair (i.e., spectral shift FRET (ss-FRET)). The fluorescence of the second polypeptide is blue-shifted compared to the absorbance of the polypeptide or variant thereof provided herein. In certain embodiments, the fluorescence of the second polypeptide is within the orange light, yellow light, green light, blue light, indigo light, or violet light region of the visible spectrum.

The fusion proteins provided herein have enhanced brightness and can be used in 2-photon imaging, ratiometric voltage imaging, and multimodal sensors for simultaneous measurement of voltage and concentration. The fusion proteins provided herein can be used in any of the methods of the present invention. The fusion proteins provided herein can be prepared using a nucleic acid encoding the inventive polypeptides that is operably linked to or fused with an additional fluorescent protein. In certain embodiments, the second fluorescent protein is GFP, YFP, citrine, mOrange2, mKate2, mRuby2, or a variant thereof. In certain embodiments, the fusion proteins can be covalently joined together. In certain embodiments, the fusion proteins can be non-covalently joined together. In certain embodiments, the fusion proteins are joined together using standard protein linkers.

In certain embodiments, the fusion proteins comprise an amino acid sequence of SEQ ID NO: 2, and an amino acid sequence of a second fluorescent protein. In certain embodiments, the fusion protein comprises a variant of an amino acid sequence of SEQ ID NO: 2, and an amino acid sequence of a second fluorescent protein. In certain embodiments, the second fluorescent protein is GFP, YFP, citrine, mOrange2, mKate2, mRuby2, or a variant thereof. In certain embodiments, the second fluorescent protein has an emission wavelength range that is blue-shifted compared to the GEVIs. In certain embodiments, the fusion proteins comprise an amino acid sequence of SEQ ID NO: 2, or a variant thereof, and an amino acid sequence of GFP, or a variant thereof. In certain embodiments, the fusion proteins comprise an amino acid sequence of SEQ ID NO: 2, or a variant thereof, and an amino acid sequence of YFP, or a variant thereof. In certain embodiments, the fusion proteins comprise an amino acid sequence of SEQ ID NO: 2, or a variant thereof, and an amino acid sequence of citrine, or a variant thereof. In certain embodiments, the fusion proteins comprise an amino acid sequence of SEQ ID NO: 2, or a variant thereof, and an amino acid sequence of mOrange2, or a variant thereof. In certain embodiments, the fusion proteins comprise an amino acid sequence of SEQ ID NO: 2, or a variant thereof, and an amino acid sequence of mKate2, or a variant thereof. In certain embodiments, the fusion proteins comprise an amino acid sequence of SEQ ID NO: 2, or a variant thereof, and an amino acid sequence of mRuby2, or a variant thereof.

In certain embodiments, the fusion proteins comprise an amino acid sequence of SEQ ID NO: 3 and an amino acid sequence of a second fluorescent protein. In certain embodiments, the fusion protein comprises a variant of an amino acid sequence of SEQ ID NO: 3. In certain embodiments, the second fluorescent protein is GFP, YFP, citrine, mOrange2, mKate2, mRuby2, or a variant thereof. In certain embodiments, the second fluorescent protein has an emission wavelength range that is blue-shifted compared to the GEVIs. In certain embodiments, the fusion proteins comprise an amino acid sequence of SEQ ID NO: 3, or a variant thereof, and an amino acid sequence of GFP, or a variant thereof. In certain embodiments, the fusion proteins comprise an amino acid sequence of SEQ ID NO: 3, or a variant thereof, and an amino acid sequence of YFP, or a variant thereof. In certain embodiments, the fusion proteins comprise an amino acid sequence of SEQ ID NO: 3, or a variant thereof, and an amino acid sequence of citrine, or a variant thereof. In certain embodiments, the fusion proteins comprise an amino acid sequence of SEQ ID NO: 3, or a variant thereof, and an amino acid sequence of mOrange2, or a variant thereof. In certain embodiments, the fusion proteins comprise an amino acid sequence of SEQ ID NO: 3, or a variant thereof, and an amino acid sequence of mKate2, or a variant thereof. In certain embodiments, the fusion proteins comprise an amino acid sequence of SEQ ID NO: 3, or a variant thereof, and an amino acid sequence of mRuby2, or a variant thereof.

In certain embodiments, the fusion proteins comprise an amino acid sequence having at least about 80%, at least about 85%, at least about 90%, at least about 95%, at least about 96%, at least about 97%, at least about 98%, or at least about 99% sequence homology to SEQ ID NO: 2, and an amino acid sequence of a second fluorescent protein. In certain embodiments, the fusion proteins comprise an amino acid sequence having at least about 80%, at least about 85%, at least about 90%, at least about 95%, at least about 97%, at least about 98%, or at least about 99% sequence homology to SEQ ID NO: 3, and an amino acid sequence of a second fluorescent protein.

In certain embodiments, the fusion proteins comprise an amino acid sequence having at least about 80%, at least about 85%, at least about 90%, at least about 95%, at least about 96%, at least about 97%, at least about 98%, or at least about 99% sequence identity to SEQ ID NO: 2, and an amino acid sequence of a second fluorescent protein. In certain embodiments, the fusion proteins comprise an amino acid sequence having at least about 80%, at least about 85%, at least about 90%, at least about 95%, at least about 96%, at least about 97%, at least about 98%, or at least about 99% sequence identity to SEQ ID NO: 3, and an amino acid sequence of a second fluorescent protein.

It is useful to have fusion proteins wherein the fused proteins span the visible spectrum. In certain embodiments, the second fluorescent protein has an emission wavelength range that is blue-shifted compared to the GEVIs. In certain embodiments, the second fluorescent protein is GFP, YFP, Citrine, mOrange2, mKate2, mRuby2, or a variant thereof. In certain embodiments, the second fluorescent protein is GFP or a variant thereof. In certain embodiments, the second fluorescent protein is YFP or a variant thereof. In certain embodiments, the second fluorescent protein is citrine or a variant thereof. In certain embodiments, the second fluorescent protein is mOrange2 or a variant thereof. In certain embodiments, the second fluorescent protein is mKate2 or a variant thereof. In certain embodiments, the second fluorescent protein is mRuby2 or a variant thereof.

In certain embodiments, the second fluorescent protein is fused to the GEVIs at either the N-terminus or the C-terminus of the GEVI. In certain embodiments, the second fluorescent protein is fused to the GEVIs at the C-terminus of the GEVI. In certain embodiments, the fusion protein comprises a polypeptide comprising an amino acid sequence of SEQ ID NO: 2 or SEQ ID NO: 3 fused at its C-terminus to a second fluorescent protein. In certain embodiments, the two polypeptides of the fusion protein are linked via a short linker. In certain embodiments, the short linker comprises 2 to 5 amino acids. In certain embodiments, the short linker comprises the amino acids Leu and Arg. In certain embodiments, the short linker comprises 2 or 3 amino acids. In certain embodiments, the short linker comprises 2 amino acids. In certain embodiments, the short linker is Leu and Arg.

In certain embodiments, the fusion protein comprises a polypeptide comprising an amino acid sequence of SEQ ID NO: 2 fused at its C-terminus to a second fluorescent protein. In certain embodiments, the fusion protein comprises a polypeptide comprising an amino acid sequence of SEQ ID NO: 2 fused at its C-terminus to a second fluorescent protein selected from GFP, YFP, citrine, mOrange2, mKate2, mRuby2 and variants thereof. In certain embodiments, the fusion protein comprises a polypeptide comprising an amino acid sequence of SEQ ID NO: 2 fused at its C-terminus to a GFP or a variant thereof. In certain embodiments, the fusion protein comprises a polypeptide comprising an amino acid sequence of SEQ ID NO: 2 fused at its C-terminus to a YFP or a variant thereof. In certain embodiments, the fusion protein comprises a polypeptide comprising an amino acid sequence of SEQ ID NO: 2 fused at its C-terminus to citrine or a variant thereof. In certain embodiments, the fusion protein comprises a polypeptide comprising an amino acid sequence of SEQ ID NO: 2 fused at its C-terminus to a mOrange2 or a variant thereof. In certain embodiments, the fusion protein comprises a polypeptide comprising an amino acid sequence of SEQ ID NO: 2 fused at its C-terminus to mKate2 or a variant thereof. In certain embodiments, the fusion protein comprises a polypeptide comprising an amino acid sequence of SEQ ID NO: 2 fused at its C-terminus to mRuby2 or a variant thereof.

In certain embodiments, the fusion protein comprises a polypeptide comprising an amino acid sequence of SEQ ID NO: 3 fused at its C-terminus to a second fluorescent protein. In certain embodiments, the fusion protein comprises a polypeptide comprising an amino acid sequence of SEQ ID NO: 3 fused at its C-terminus to a second fluorescent protein selected from GFP, YFP, citrine, mOrange2, mKate2, mRuby2 and variants thereof. In certain embodiments, the fusion protein comprises a polypeptide comprising an amino acid sequence of SEQ ID NO: 3 fused at its C-terminus to a GFP or a variant thereof. In certain embodiments, the fusion protein comprises a polypeptide comprising an amino acid sequence of SEQ ID NO: 3 fused at its C-terminus to a YFP or a variant thereof. In certain embodiments, the fusion protein comprises a polypeptide comprising an amino acid sequence of SEQ ID NO: 3 fused at its C-terminus to a citrine or a variant thereof. In certain embodiments, the fusion protein comprises a polypeptide comprising an amino acid sequence of SEQ ID NO: 3 fused at its C-terminus to a mOrange2 or a variant thereof. In certain embodiments, the fusion protein comprises a polypeptide comprising an amino acid sequence of SEQ ID NO: 3 fused at its C-terminus to a mKate2 or a variant thereof. In certain embodiments, the fusion protein comprises a polypeptide comprising an amino acid sequence of SEQ ID NO: 3 fused at its C-terminus to a mRub2 or a variant thereof.

Since the GEVI fusion proteins (i.e., eFRET GEVIs) span the visible spectrum, the GEVI fusion proteins provided herein are useful in multicolor voltage imaging. The high brightness of the eFRET GEVIs also makes these fusion proteins useful for voltage imaging in vivo. The high brightness of the eFRET GEVIs also makes these proteins useful for voltage imaging with two-photon excitation. Accordingly, provided is a method of detecting action potentials in various cells, for example, in mammalian neurons, skeletal myocytes, cardiac cells, glial cells, pancreatic beta cells, or in endothelial cell, for example in mammalian cardiomyocytes (e.g., human induced pluripotent stem cell (iPS)-derived cardiomyocytes). Cardiomyocytes include ventricular, atrial, and nodal cells. Such methods comprises transfecting neurons or cardiac cells with the GEVI fusion proteins. In certain embodiments, the fusion protein trafficks to sub-cellular compartments. In certain embodiments, the fusion protein trafficks to the endoplasmic reticulum. In certain embodiments, the fusion protein localizes to a membrane of the cell. In certain embodiments, the fusion protein localizes to the plasma membrane. In certain embodiments, the fusion protein localizes to the membrane of sub-cellular compartments.

In certain embodiments, the fusion proteins enables ratiometric determination of membrane potential. Since it has been observed that rate of eFRET decreases with increasing distance between the polypeptides, such embodiments employ the use of a long linker between the two polypeptides being fused such that the polypeptides do not under go eFRET. Since the fluorescence of the second fluorescent protein is independent of membrane potential, the ratio of fluorescence for the inventive polypeptides to the fluorescene of the second fluorescent protein provides a measure of membrane potential that is independent of variations in expression level, illumination, or movement.

Membrane potential is only one of several mechanisms of signaling within cells. In certain applications, it is desirable to correlate changes in membrane potential with changes in concentration of other species, such as $Ca^{2+}$, $H^+$ (i.e., pH), $Na^+$, $K^+$, $Cl^-$, ATP, and cAMP. The GEVIs provided herein can also be useful in multimodal sensor applications where the visible spectrum is used for other imaging modalities such as simultaneously measuring the concentrations of these other ions. Examples of other fusion proteins include the GEVIs provided herein fused with a fluorescent pH indicator (e.g., pHluorin) or with a fluorescent $Ca^{2+}$ indicator (e.g., GCaMP6). In such applications, the second fluorescent polypeptide would interfere with such applications. However, the removal of the second fluorescent polypeptide may interfere with, for example, trafficking properties of the GEVIs. Thus, the second fluorescent polypeptide of the fusion protein can be modified to the corresponding non-fluorescent variant. Accordingly, in certain embodiments, the fusion proteins comprise an amino acid sequence of SEQ ID NO: 2 and a second fluorescent polypeptide, wherein second fluorescent polypeptide is modified to the corresponding non-fluorescent variant. In certain embodiments, the fusion proteins comprise an amino acid sequence of SEQ ID NO: 3 and a second fluorescent polypeptide, wherein second fluorescent polypeptide is modified to the corresponding non-fluorescent variant. In certain embodiments, the second fluorescent polypeptide is mOrange2. In certain embodiments, the mOrange2 polypeptide is mutated to the non-fluorescent form. In certain embodiments, the mOrange2 polypeptide mutant comprises a Y72A mutation. The protein ID number of mOrange is D0VWW2.

Additional second fluorescent proteins include Venus, EGFP, EYFP, EBFB, DsRed, RFP, and fluorescent variants thereof.

Nucleic Acid Constructs and Expression Vectors

Provided herein are nucleic acid constructs comprising the inventive polynucleotides. In certain embodiments, the nucleic acid construct comprises a polynucleotide encoding an amino acid sequence of SEQ ID NO: 1, wherein at least one of the amino acids at positions 60, 80, 95, 106, or 161 have been mutated. In certain embodiments, the nucleic acid construct comprises a polynucleotide encoding an amino acid sequence of SEQ ID NO: 1, wherein the amino acids at positions 60, 80, 95, 106, and 161 have been mutated. In certain embodiments, the nucleic acid construct comprises a polynucleotide encoding an amino acid sequence of SEQ ID NO: 2. In certain embodiments, the nucleic acid construct comprises a polynucleotide encoding an amino acid sequence of SEQ ID NO: 3.

In certain embodiments, the nucleic acid construct comprises a polynucleotide of SEQ ID NO: 4, wherein the polynucleotide encodes for at least one amino acid mutation at positions 60, 80, 95, 106, or 161 of the encoded polypeptide. In certain embodiments, the nucleic acid construct comprises a polynucleotide of SEQ ID NO: 4, wherein the polynucleotide encodes for amino acid mutation at positions 60, 80, 95, 106, and 161 of the encoded polypeptide. In certain embodiments, the nucleic acid construct comprises a polynucleotide of SEQ ID NO: 5. In certain embodiments, the nucleic acid construct comprises a polynucleotide of SEQ ID NO: 6.

In certain embodiments, the nucleic acid construct comprises a second polynucleotide encoding a second polypeptide as described herein. In certain embodiments, the second polypeptide is fluorescent. In certain embodiments, the second fluorescent polypeptide is GFP, YFP, citrine, mOrange2, mKate2, mRuby2, or a variant thereof. In certain embodiments, the second fluorescent polypeptide is capable of indicating ion concentration. In certain embodiments, the ion concentration indicated is calcium or pH. In certain embodiments, the two polypeptides are connected to encode a fusion protein comprising the inventive polypeptides and a second fluorescent protein.

In certain embodiments, the nucleic acid construct comprises a promoter sequence to control the expression of the polynucleotide or polynucleotides. The promoter sequence is operatively linked to the polynucleotide sequence that encode the inventive GEVIs. In certain embodiments, the nucleic acid construct comprises a pan cellular promoter. In certain embodiments, the pan cellular promoter is a CAG enhancer, CMB, or ubiquitin, as described in US Patent Publication No. 2013/0224756, incorporated by reference. In certain embodiments, the nucleic acid construct comprises a neuron specific promoter sequence. In certain embodiments, the neuron specific promoter is $Ca^{2+}$-calmodulin-dependent protein kinase II (CaMKIIα) promoter. In certain embodiments, the nucleic acid construct comprises a promoter that is a human synapsin (hSyn) promoter. In certain embodiments, the nucleic acid construct comprises a promoter that is a GAD67 promoter.

In certain embodiments, the nucleic acid construct comprises a first promoter sequence to control the expression of the inventive polynucleotides described herein, and a second promoter sequence to control the expression of the second polynucleotides described herein, said first promoter sequence and said second promoter sequence are different from each other. In certain embodiments, the second polynucleotides encode the fluorescent polypeptides or the non-fluorescent version such as GFP, YFP, citrine, mOrange2, mKate2, mRuby2, or a variant thereof.

Further provided herein are expression vectors comprising any of the aforementioned inventive polynucleotides or the nucleic acid constructs. The term "vector" refers to a carrier DNA molecule into which a nucleic acid sequence can be inserted for introduction into a host cell. Vectors useful in the methods provided may include additional sequences including, but not limited to one or more signal sequences and/or promoter sequences, or a combination thereof. An "expression vector" is a specialized vector that contains the necessary regulatory regions needed for expression of a gene of interest in a host cell such as transcription control elements (e.g. promoters, enhancers, and termination elements). Expression vectors and methods of their use are well known in the art. Non-limiting examples of suitable expression vectors and methods for their use are provided herein. Nucleic acid constructs may be integrated and packaged into non-replicating, defective viral genomes like Adenovirus, Adeno-associated virus (AAV), or Herpes simplex virus (HSV) or others, including retroviral and lentiviral vectors, for infection or transduction into cells.

In certain embodiments, the vector comprises a trafficking sequence. The inventive polypeptides described herein can be targeted to intracellular organelles, including mitochondria, the endoplasmic reticulum, the sarcoplasmic reticulum, synaptic vesicles, and phagosomes. In certain embodiments, the vector comprises a membrane-targeting nucleic acid sequence operatively linked to to the polynucleotide encoding the inventive polypeptide. In certain embodiments, the membrane-targeting nucleic acid is a plasma membrane targeting nucleic acid sequence. In certain embodiments, the membrane-targeting nucleic acid sequence is a subcellular compartment-targeting nucleic acid sequence. In certain embodiments, the subcellular compartment is selected from a mitochondrial membrane, an endoplasmic reticulum, a sarcoplastic reticulum, a nuclear membrane, a synaptic vesicle, an endosome, and a phagosome. In certain embodiments, the subcellular compartment is the endoplasmic reticulum, the mitochondrial inner membrane, the nuclear membrane, or a synaptic vesicle. In certain embodiments, the inventive polypeptides described herein can be targeted to membrane regions such as the plasma membrane or to membranes of sub-cellular compartments.

In certain embodiments, the vector also includes one, two, or more nucleic acid signal sequences operatively linked to the polynucleotide sequence encoding the inventive polypeptides. In certain embodiments, the vector is a plasmid vector, cosmid vector, viral vector, or an artificial chromosome.

In certain embodiments, the vector is a lentiviral vector. In certain embodiments, the nucleic acid constructs comprising the inventive polynucleotides are incorporated into a lentiviral vector under the CaMKIIα promoter, adapted from Addgene plasmid 22217.

A vector can also further comprises at least one of the following: a marker gene, a reporter gene, an antibiotic-resistance gene, an enhancer sequence, a gene encoding a selected gene product, a polyadenylation site, and a regulatory sequence.

Vectors useful in methods of the invention may include additional sequences including, but not limited to, one or more signal sequences and/or promoter sequences, or a combination thereof. Expression vectors and methods of their use are well known in the art. Non-limiting examples of suitable expression vectors and methods for their use are provided herein.

In certain embodiments of the invention, a vector may be a lentivirus comprising the gene for a light-activated ion channel polypeptide of the invention, such as ChR64, ChR86, or a variant thereof. A lentivirus is a non-limiting example of a vector that may be used to create stable cell line.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of a light-activated ion channel polypeptide in a wide variety of cell types—thus a promoter for a gene that is widely expressed in a variety of cell types, for example, a "housekeeping gene" can be used to express a light-activated ion channel polypeptide in a variety of cell types. Non-limiting examples of general promoters are provided elsewhere herein and suitable alternative promoters are well known in the art.

In certain embodiment, the inventive polypeptides are encoded by a delivery vector. Non-liminting exemplary vectors include: plasmids (e.g. pBADTOPO, pCI-Neo, pcDNA3.0), cosmids, and viruses (such as a lentivirus, an adeno-associated virus, or a baculovirus). In certain embodiments, the vectors are bicistronic vectors for co-expression of the inventive polypeptides and another fluorescent protein. In certain embodiments, the separate vectors are used for the separate expression of the inventive polypeptides and another fluorescent protein.

In certain embodiments, to express a fusion protein such as Arch-mOrange2 variants in HeLa cells, the polynucleotide in the pBAD vector was first amplified by PCR using primers Fw_BamHI_Kozak_Arch and RV_FP_ERex_stp_XbaI. This reverse primer encodes the endoplasmic reticulum (ER) export sequence from the inward-rectifier potassium channel Kir2.1 (FCYENE) (SEQ ID NO: 8), which has been reported to be effective for improving the membrane trafficking of Arch in mammalian cells. In certain embodiments, the purified polynucleotide DNA was digested with BamHI and XbaI restriction enzymes and ligated into a purified plasmid, such as the pcDNA3.1 plasmid, that had been digested with the same two enzymes.

The ligation reaction was used for the transformation of electrocompetent *E. coli* strain, such as DH10B cells. Cells were plated, individual colonies were picked and grown, followed by a small-scale isolation of plasmid DNA. Each gene in the plasmid was fully sequenced using T7_FW and BGH_RV primers. Plasmid DNA was then used for subsequent cell transfection. In certain embodiments, the cells being transfected are HeLa cells.

In certain embodiments, the vector used is a lentivirus vector. To enable more accurate electrophysiological characterization via patch clamp in HEK cells and primary neuron cultures, the inventive polynucleotides can be cloned into restriction enzyme sites, such as the BamHI/EcoRI sites, of a lentivirus vector such as FCK-Arch-GFP (Addgene: 22217). This vector contains a CaMKIIα promoter and a Woodchuck Hepatitis Virus Posttranscriptional Regulatory Element (WPRE) after the 3' end of the open reading frame. The Arch cDNA was generated by PCR using forward primer FW_BamHI_Kozak_Arch_ValSer and overlapping reverse primers RV_FP_TS and RV_TS_ERex_st-p_EcoRI. These reverse primers introduce a trafficking signal (TS) motif and endoplasmic reticulum (ER) export signal peptide sequence at the C-terminus of the inventive polypeptide.

Table 4 summarizes exemplary embodiments that can be used to create viral constructs that express the genetically encoded voltage indicators provided herein. The sequence listings can be found in US Patent Application No. 2013/0224756, which is herein incorporated by reference in its entirety.

TABLE 4

Exemplary embodiments that can be used to gene constructs with the inventive polypeptides.

| Virus backbone | Lentivirus |
| --- | --- |
| Promoter | CamKII (neuron specific) |
|  | CAG enhancer (pan cellular) |
|  | CMV (pan cellular) |
|  | Ubiquitin (pan cellular) |
| Voltage-sensing domain | Inventive polypeptides provided herein |

An "inducible promoter" is a promoter that is capable of directly or indirectly activating transcription of one or more DNA sequences or genes in response to a "regulatory agent" (e.g., doxycycline), or a "stimulus" (e.g., heat). In the absence of a "regulatory agent" or "stimulus", the DNA sequences or genes will not be substantially transcribed. The term "not substantially transcribed" or "not substantially expressed" means that the level of transcription is at least 100-fold lower than the level of transcription observed in the presence of an appropriate stimulus or regulatory agent; generally at least 200-fold, 300-fold, 400-fold, 500-fold or more. As used herein, the terms "stimulus" and/or "regulatory agent" refers to a chemical agent, such as a metabolite, a small molecule, or a physiological stress directly imposed upon the organism such as cold, heat, toxins, or through the action of a pathogen or disease agent. A recombinant cell containing an inducible promoter may be exposed to a regulatory agent or stimulus by externally applying the agent or stimulus to the cell or organism by exposure to the appropriate environmental condition or the operative pathogen. Inducible promoters initiate transcription only in the presence of a regulatory agent or stimulus. Examples of inducible promoters include the tetracycline response element and promoters derived from the β-interferon gene, heat shock gene, metallothionein gene or any obtainable from steroid hormone-responsive genes. Inducible promoters which may be used in performing the methods of the present invention include those regulated by hormones and hormone analogs such as progesterone, ecdysone and glucocorticoids as well as promoters which are regulated by tetracycline, heat shock, heavy metal ions, interferon, and lactose operon activating compounds. For review of these systems see Gingrich and Roder, 1998, Annu Rev Neurosci 21, 377-405. Tissue specific expression has been well characterized in the field of gene expression and tissue specific and inducible promoters are well known in the art. These promoters are used to regulate the expression of the foreign gene after it has been introduced into the target cell.

The promoter sequence may be a "cell-type specific promoter" or a "tissue-specific promoter" which means a nucleic acid sequence that serves as a promoter, i.e., regulates expression of a selected nucleic acid sequence operably linked to the promoter, and which affects expression of the selected nucleic acid sequence in specific cells or tissues where membrane potential is desired to be measured. In some embodiments, the cell-type specific promoter is a leaky cell-type specific promoter. The term "leaky" promoter refers to a promoter which regulates expression of a selected nucleic acid primarily in one cell type, but cause expression in other cells as well. For expression of an exogenous gene specifically in neuronal cells, a neuron-specific enolase promoter can be used (see Forss-Petter et al., 1990, Neuron 5: 187-197). For expression of an exogenous gene in dopaminergic neurons, a tyrosine hydroxylase promoter can be used. For expression in pituitary cells, a pituitary-specific promoter such as POMC may be used (Hammer et al., 1990, Mol. Endocrinol. 4:1689-97). Examples of muscle specific promoters include, for example α-myosin heavy chain promoter, and the MCK promoter. Other cell specific promoters active in mammalian cells are also contemplated herein. Such promoters provide a convenient means for controlling expression of the exogenous gene in a cell of a cell culture or within a mammal.

In some embodiments, the expression vector is a lentiviral vector. Lentiviral vectors useful for the methods and compositions described herein can comprise a eukaryotic promoter. The promoter can be any inducible promoter, including synthetic promoters, that can function as a promoter in a eukaryotic cell. For example, the eukaryotic promoter can be, but is not limited to, ecdysone inducible promoters, E1a inducible promoters, tetracycline inducible promoters etc., as are well known in the art. In addition, the lentiviral vectors used herein can further comprise a selectable marker, which can comprise a promoter and a coding sequence for a selectable trait. Nucleotide sequences encoding selectable markers are well known in the art, and include those that encode gene products conferring resistance to antibiotics or anti-metabolites, or that supply an auxotrophic requirement. Examples of such sequences include, but are not limited to, those that encode thymidine kinase activity, or resistance to methotrexate, ampicillin, kanamycin, chloramphenicol, puromycinor zeocin, among many others.

In some embodiments the viral vector is an adeno-associated virus (AAV) vector. AAV can infect both dividing and non-dividing cells and may incorporate its genome into that of the host cell.

The type of vector one selects will also depend on whether the expression is intended to be stable or transient.

The invention also provides cells that are genetically engineered to express the microbial rhodopsin VIPs. The cell may be engineered to express the VIP transiently or stably.

The invention provides methods of making both transiently expressing cells and cells and cell lines that express the microbial rhodopsins stably.

Transient Expression.

One of ordinary skill in the art is well equipped to engineer cells that are transiently transfected to express the VIPs or PROPS as described herein. Transduction and transformation methods for transient expression of nucleic acids are well known to one skilled in the art.

Transient transfection can be carried out, e.g., using calcium phosphate, by electroporation, or by mixing a cationic lipid with the material to produce liposomes, cationic polymers or highly branched organic compounds. All these are in routine use in genetic engineering.

One of ordinary skill in the art is well equipped to engineer cells that stably express the VIPs or PROPS as described herein. These methods are also in routine use in genetic engineering. Exemplary protocols can be found, e.g., in Essential Stem Cell Methods, edited by Lanza and Klimanskaya, published in 2008, Academic Press. For example, one can generate a virus that integrates into the genome and comprises a selectable marker, and infect the cells with the virus and screen for cells that express the marker, which cells are the ones that have incorporated the virus into their genome. For example, one can generate a VSV-g psuedotyped lenti virus with a puromycin selectable marker in HEK cells according to established procedures. Generally, one can use a stem cell specific promoter to encode a GFP if FACS sorting is necessary. The hiPS cultures are cultivated on embryonic fibroblast (EF) feeder layers or on Matrigel in fibroblast growth factor supplemented EF conditioned medium. The cells are dissociated by trypsinization to a single cell suspension The cells can be plated, e.g., $1\times10^5$ cells on a tissue culture 6-well plate pretreated with, e.g., Matrigel. To maintain the cells in an undifferentiated state, one can use, e.g., EF conditioned medium. About 6 hours after plating, one can add virus supernatant to adhered cells (use $5\times10^6$ IU virus per $1\times10^5$ cells). Add 6 µg/mL protamine sulfate to enhance virus infection. Cells are cultured with the virus for 24 hours; washed, typically with PBS, and fresh media is added with a selection marker, such as 1 µg/mL puromycin. The medium is replaced about every 2 days with additional puromycin. Cells surviving after 1 week are re-plated, e.g., using the hanging drop method to form EBs with stable incorporation of gene.

In some embodiments, it is advantageous to express a VIP (e.g., Arch 3 D95N) in only a single cell-type within an organism, and further, if desired, to direct the sensor to a particular subcellular structure within the cell. Upstream promoters control when and where the gene is expressed. Constructs are made that optimize expression in all eukaryotic cells. In one embodiment, the VIP is under the control of a neuron-specific promoter.

The promoter sequence can be selected to restrict expression of the protein to a specific class of cells and environmental conditions. Common promoter sequences include, but are not limited to, CMV (cytomegalovirus promoter; a universal promoter for mammalian cells), 14xUAS-E1b (in combination with the transactivator Gal4, this promoter allows combinatorial control of transgene expression in a wide array of eukaryotes. Tissue-specific expression can be achieved by placing Gal4 under an appropriate promoter, and then using Gal4 to drive the UAS-controlled transgene), HuC (drives pan-neuronal expression in zebrafish and other teleosts), ara (allows regulation of expression with arabinose in bacteria) and lac (allows regulation of expression with IPTG in bacteria).

In some embodiments, the VIP further comprises a localization or targeting sequence to direct or sort the sensor to a particular face of a biological membrane or subcellular organelle. Useful localization sequences provide for highly specific localization of the protein, with minimal accumulation in other subcellular compartments. Example localization sequences that direct proteins to specific subcellular structures are provided in US Patent Publication No. 2013/0224756 (incorporated by reference) and include nuclear (import signal), endoplasmic reticulum (import signal), endoplasmic reticulum (retention signal), peroxisome (import signal), peroxisome (import signal), mitochondrial inner membrane, mitochondrial outer membrane, plasma membrane (cytosolic face), plasma membrane (cytosolic face), mitochondrial targeting sequence: human PINK1, mitochondrial targeting sequence: human serine protease HTRA2, mitochondrial targeting sequence: human cytochrome oxidase 1, mitochondrial targeting sequence: human cytochrome oxidase 2, mitochondrial targeting sequence: human protein phospatase 1K, mitochondrial targeting sequence: human ATP synthase alpha, and mitochondrial targeting sequence: human frataxin.

Other examples of localization signals are described in, e.g., "Protein Targeting", chapter 35 of Stryer, L., Biochemistry (4th ed.). W. H. Freeman, 1995 and Chapter 12 (pages 551-598) of Molecular Biology of the Cell, Alberts et al. third edition, (1994) Garland Publishing Inc. In some embodiments, more than one discrete localization motif is used to provide for correct sorting by the cellular machinery. For example, correct sorting of proteins to the extracellular face of the plasma membrane can be achieved using an N-terminal signal sequence and a C-terminal GPI anchor or transmembrane domain.

Typically, localization sequences can be located almost anywhere in the amino acid sequence of the protein. In some cases the localization sequence can be split into two blocks separated from each other by a variable number of amino acids. The creation of such constructs via standard recombinant DNA approaches is well known in the art, as for example described in Maniatis et al., *Molecular Cloning A Laboratory Manual*, Cold Spring Harbor Laboratory, N.Y, 1989).

Targeting to the Plasma Membrane:

In some embodiments, constructs are designed to include signaling sequences to optimize localization of the protein to the plasma membrane. These can include e.g., a C-terminal signaling sequence from the nicotinic acetylcholine receptor, and/or an endoplasmic reticulum export motif from Kir2.1 comprising the sequence FCYENE (SEQ ID NO: 8). Examples of targeting sequences are provided in US Patent Publication No. 2013/0224756, incorporated herein by reference.

Additional improvements in plasma localization can be obtained by adding Golgi export sequences (e.g., from Kir2.1) and membrane localization sequences (e.g., from Kir2.1) (Gradinaru et al. *Cell* (2010)). In some embodiments, the targeting sequence is selected to regulate intracellular transport of the protein to the desired subcellular structure. In one embodiment the protein is targeted to the plasma membrane of a eukaryotic cell. In this case the targeting sequence can be designed following the strategy outlined in, e.g., Gradinaru et al., "Molecular and Cellular Approaches for Diversifying and Extending Optogenetics,"

Cell 141, 154-165 (2010). The term "signal sequence" refers to N-terminal domains that target proteins into a subcellular locale e.g., the endoplasmic reticulum (ER), and thus are on their way to the plasma membrane. Signal sequences used in optogenetic voltage sensors can be derived from the proteins 132-n-acetylcholine receptor (SS B2nAChR) and PPL. In addition, there is an endogenous signaling sequence on microbial rhodopsin proteins that can be harnessed for appropriate subcellular targeting. A trafficking signal (TS) can optionally be inserted into the genome C-terminal to the microbial rhodopsin and N-terminal to the accessory fluorescent protein. In one embodiment, the trafficking signal is derived from the Kir2.1 protein as specified in Gradinaru et al. In another embodiment, an ER export motif is inserted at the C-terminus of the accessory fluorescent protein.

Targeting Mitochondria:

For measuring mitochondrial membrane potential or for studying mitochondria, one may wish to localize PROPS to the mitochondrial inner membrane or mitochondrial outer membrane, in which case appropriate signaling sequences can be added to the rhodopsin protein.

Optogenetic voltage sensors can be targeted to the inner mitochondrial membrane, following a procedure such as that described in, e.g., A. Hoffmann, V. Hildebrandt, J. Heberle, and G. Büldt, "Photoactive mitochondria: in vivo transfer of a light-driven proton pump into the inner mitochondrial membrane of *Schizosaccharomyces pombe*," Proc. Natl. Acad. Sci. USA 91, PNAS 9367-9371 (1994).

Codon Usage:

A large number of mammalian genes, including, for example, murine and human genes, have been successfully expressed in various host cells, including bacterial, yeast, insect, plant and mammalian host cells. Nevertheless, despite the burgeoning knowledge of expression systems and recombinant DNA technology, significant obstacles remain when one attempts to express a foreign or synthetic gene in a selected host cell. For example, translation of a synthetic gene, even when coupled with a strong promoter, often proceeds much more slowly than would be expected. The same is frequently true of exogenous genes that are foreign to the host cell. This lower than expected translation efficiency is often due to the protein coding regions of the gene having a codon usage pattern that does not resemble those of highly expressed genes in the host cell. It is known in this regard that codon utilization is highly biased and varies considerably in different organisms and that biases in codon usage can alter peptide elongation rates. It is also known that codon usage patterns are related to the relative abundance of tRNA isoacceptors, and that genes encoding proteins of high versus low abundance show differences in their codon preferences.

Codon-optimization techniques have been developed for improving the translational kinetics of translationally inefficient protein coding regions. These techniques are based on the replacement of codons that are rarely or infrequently used in the host cell with those that are host-preferred. Codon frequencies can be derived from literature sources for the highly expressed genes of many organisms (see, for example, Nakamura et al., 1996, Nucleic Acids Res. 24: 214-215). These frequencies are generally expressed on an 'organism-wide average basis' as the percentage of occasions that a synonymous codon is used to encode a corresponding amino acid across a collection of protein-encoding genes of that organism, which are preferably highly expressed. In one embodiment, the codons of a microbial rhodopsin protein are optimized for expression in a eukaryotic cell. In one embodiment, the eukaryotic cell is a human cell.

It is preferable but not necessary to replace all the codons of the microbial polynucleotide with synonymous codons having higher translational efficiencies in eukaryotic (e.g., human) cells than the first codons. Increased expression can be accomplished even with partial replacement. Typically, the replacement step affects at least about 5%, 10%, 15%, 20%, 25%, 30%, more preferably at least about 35%, 40%, 50%, 60%, 70% or more of the first codons of the parent polynucleotide. Suitably, the number of, and difference in translational efficiency between, the first codons and the synonymous codons are selected such that the protein of interest is produced from the synthetic polynucleotide in the eukaryotic cell at a level which is at least about 110%, suitably at least about 150%, preferably at least about 200%, more preferably at least about 250%, even more preferably at least about 300%, even more preferably at least about 350%, even more preferably at least about 400%, even more preferably at least about 450%, even more preferably at least about 500%, and still even more preferably at least about 10000%, of the level at which the protein is produced from the parent polynucleotide in the eukaryotic cell.

Generally, if a parent polynucleotide has a choice of low and intermediate translationally efficient codons, it is preferable in the first instance to replace some, or more preferably all, of the low translationally efficient codons with synonymous codons having intermediate, or preferably high, translational efficiencies. Typically, replacement of low with intermediate or high translationally efficient codons results in a substantial increase in production of the polypeptide from the synthetic polynucleotide so constructed. However, it is also preferable to replace some, or preferably all, of the intermediate translationally efficient codons with high translationally efficient codons for optimized production of the polypeptide.

Replacement of one codon for another can be achieved using standard methods known in the art. For example codon modification of a parent polynucleotide can be effected using several known mutagenesis techniques including, for example, oligonucleotide-directed mutagenesis, mutagenesis with degenerate oligonucleotides, and region-specific mutagenesis. Exemplary in vitro mutagenesis techniques are described for example in U.S. Pat. Nos. 4,184,917, 4,321, 365 and 4,351,901 or in the relevant sections of Ausubel et al. (Current Protocols in Molecular Biology, John Wiley & Sons, Inc. 1997) and of Sambrook et al., (Molecular Cloning. A Laboratory Manual, Cold Spring Harbor Press, 1989). Instead of in vitro mutagenesis, the synthetic polynucleotide can be synthesized de novo using readily available machinery as described, for example, in U.S. Pat. No. 4,293,652. However, it should be noted that the present invention is not dependent on, and not directed to, any one particular technique for constructing the synthetic polynucleotide.

The genes for microbial rhodopsins (e.g., GPR) express well in *E. coli*, but less well in eukaryotic hosts. In one embodiment, to enable expression in eukaryotes a version of the gene with codon usage appropriate to eukaryotic (e.g., human) cells is designed and synthesized. This procedure can be implemented for any gene using publicly available software, such as e.g., the Gene Designer 2.0 package (available on the world wide web at dna20.com/genedesigner2/). Some of the "humanized" genes are referred to herein by placing the letter "h" in front of the name, e.g.

hGPR. The Arch 3 rhodopsins and mutants thereof described herein and in the examples are all optimized for human codon usage.

Methods of Measuring Membrane Potential

Further provided herein are methods of measuring membrane potential changes in cells comprising the nucleic acid constructs or the vectors provided herein.

In certain embodiments, a method for measuring membrane potential in a cell expressing a polynucleotide encoding the inventive polypeptides comprises the steps of: a) exciting, in vitro, at least one cell comprising a nucleic acid encoding an inventive polypeptide with light of at least one wavelength; and b) detecting, in vitro, at least one optical signal from the at least one cell, wherein the level of fluorescence emitted by the at least one cell compared to a reference is indicative of the membrane potential of the cell.

In certain embodiments, the inventive polypeptide is an archaerhodopsin variant with reduced ion pumping activity compared to a natural archaerhodopsin from which it is derived and possesses improved properties as described herein.

In certain embodiments, the archaerhodopsin variant comprises a mutated proton acceptor proximal to the Schiff Base. In certain embodiments, the at least one wavelength is a wavelength between 590 to 690 nm. In certain embodiments, the at least one wavelength is a wavelength between 600 to 690 nm. In certain embodiments, the at least one wavelength is a wavelength between 620 to 690 nm. In certain embodiments, the at least one wavelength is a wavelength between 640 to 690 nm. In certain embodiments, the at least one wavelength is a wavelength between 650 to 690 nm.

In certain embodiments, the cell is a prokaryotic cell. In certain embodiments, the cell is a eukaryotic cell. In certain embodiments, the eukaryotic cell is a mammalian cell. In certain embodiments, the eukaryotic cell is a stem cell or a pluripotent or a progenitor cell. In certain embodiments, the eukaryotic cell is an induced pluripotent cell. In certain embodiments, the eukaryotic cell is a neuron. In certain embodiments, the eukaryotic cell is a cardiomyocyte. In certain embodiments, the method comprises a plurality of cells.

In certain embodiments, the method comprises a step of transfecting, in vitro, the at least one cell with a vector comprising the polynucleotides encoding the inventive polypeptides herein. In certain embodiments, the method comprises the polynucleotides encoding the inventive polypeptides herein is operably linked to a cell-type specific promoter. In certain embodiments, the method comprises the polynucleotides encoding the inventive polypeptides herein is operably linked to a membrane-targeting nucleic acid sequence. In certain embodiments, the membrane-targeting nucleic acid is a plasma membrane targeting nucleic acid sequence. In certain embodiments, the membrane-targeting nucleic acid sequence is a subcellular compartment-targeting nucleic acid sequence. In certain embodiments, the subcellular compartment is selected from a mitochondrial membrane, an endoplasmic reticulum, a sarcoplastic reticulum, a synaptic vesicle, an endosome and a phagosome.

In certain embodiments, the method comprises the polynucleotides encoding the inventive polypeptides herein is operably linked to a second polynucleotide sequence encoding at least one additional fluorescent protein. In certain embodiments, the at least one additional fluorescent protein is a fluorescent protein capable of indicating the ion concentration in the cell. In certain embodiments, the fluorescent protein capable of indicating ion concentration is a calcium indicator. In certain embodiments, the fluorescent protein capable of indicating ion concentration is a pH indicator.

In certain embodiments, the at least one additional fluorescent protein is capable of undergoing nonradiative fluorescence resonance energy transfer to the inventive polypeptide, with a rate of energy transfer dependent on the membrane potential. In certain embodiments, the at least one additional fluorescent protein is GFP, YFP, citrine, mOrange2, mKate2, mRuby2, or a variant thereof.

In certain embodiments, the brightness of the fluorescent protein is insensitive to membrane potential and local chemical environment.

In certain embodiments, the method further comprising steps of exciting, in vitro, the at least one cell with light of at least a first and a second wavelength; and detecting, in vitro, the at least first and the second optical signal resulting from the excitation with the at least the first and the second wavelength from the at least one cell. In certain embodiments, the at least second wave length is between 447-594 nm. In certain embodiments, method further comprises a step of calculating the ratio of the fluorescence emission from the GEVIs to the fluorescence emission of the at least one additional fluorescent protein to obtain a measurement of membrane potential independent of variations in expression level.

In certain embodiments, the method further comprises the step of exposing, in vitro, the at least one cell to a stimulus capable of, or suspected to be capable of changing membrane potential.

In certain embodiments, the stimulus a candidate agent. In certain embodiments, the stimulus is a change to the composition of the cell culture medium.

In certain embodiments, the stimulus is an electrical current. In certain embodiments, the method further comprises the step of measuring, in vitro, the at least one optical signal at a first and at least at a second time point.

Cells

According to another aspect of the invention, a cell that expresses any of the aforementioned embodiments of a vector or nucleic acid construct is provided. In another aspect, also provided are cells comprising the inventive polypeptides. Cells that are useful according to the invention include eukaryotic and prokaryotic cells. Eukaryotic cells include cells of non-mammalian invertebrates, such as yeast, plants, and nematodes, as well as non-mammalian vertebrates, such as fish and birds. The cells also include mammalian cells, including human cells. The cells also include immortalized cell lines such as HEK, HeLa, CHO, 3T3, which may be particularly useful in applications of the methods for drug screens. The cells also include stem cells, pluripotent cells, progenotir cells, and induced pluripotent cells. Differentiated cells including cells differentiated from the stem cells, pluripotent cells and progenitor cells are included as well.

In some embodiments, the cells are cultured in vitro or ex vivo. In some embodiments, the cells are part of an organ or an organism.

The methods can also be applied to any other membrane-bound structure, which may not necessarily be classified as a cell. Such membrane bound structures can be made to carry the microbial rhodopsin proteins of the invention by, e.g., fusing the membranes with cell membrane fragments that carry the microbial rhodopsin proteins of the invention.

Cells include also zebrafish cardiomyocytes; immune cells (primary murine and human cultures and iPS-derived lines for all, in addition to the specific lines noted below), including B cells (e.g., human Raji cell line, and the DT40 chicken cell line), T cells (e.g., human Jurkat cell line), Macrophages, Dendritic cells, and Neutrophils (e.g., HL-60 line). Additionally, one can use glial cells: astrocytes and oligodendrocytes; pancreatic beta cells; hepatocytes; non-cardiac muscle cells; endocrine cells such as parafollicular and chromaffin; and yeast cells. Cells also include neuronal cells, such as neurons, and skeletal cells.

The cell can also be a Gram positive or a Gram negative bacteria, as well as pathogenic bacteria of either Gram type. The pathogenic cells are useful for applications of the method to, e.g., screening of novel antibiotics that affect membrane potential to assist in destruction of the bacterial cell or that affect membrane potential to assist destruction of the bacterial cell in combination with the membrane potential affecting agent; or in the search for compounds that suppress efflux of antibiotics.

The membrane potential of essentially any cell, or any phospholipid bilayer enclosed structure, can be measured using the methods and compositions described herein. Examples of the cells that can be assayed are a primary cell e.g., a primary hepatocyte, a primary neuronal cell, a primary myoblast, a primary mesenchymal stem cell, primary progenitor cell, or it may be a cell of an established cell line. It is not necessary that the cell be capable of undergoing cell division; a terminally differentiated cell can be used in the methods described herein. In this context, the cell can be of any cell type including, but not limited to, epithelial, endothelial, neuronal, adipose, cardiac, skeletal muscle, fibroblast, immune cells, hepatic, splenic, lung, circulating blood cells, reproductive cells, gastrointestinal, renal, bone marrow, and pancreatic cells. The cell can be a cell line, a stem cell, or a primary cell isolated from any tissue including, but not limited to, brain, liver, lung, gut, stomach, fat, muscle, testes, uterus, ovary, skin, spleen, endocrine organ and bone, etc. Where the cell is maintained under in vitro conditions, conventional tissue culture conditions and methods can be used, and are known to those of skill in the art. Isolation and culture methods for various cells are well within the knowledge of one skilled in the art. The cell can be a prokaryotic or eukaryotic cell. In certain embodiments, the cell is a mammalian cell. In certain embodiments, the cell is a human cell. In one embodiment, the cell is a neuron or other cell of the brain. In some embodiment, the cell is a cardiomyocyte. In some embodiments, the cell is cardiomyocyte that has been differentiated from an induced pluripotent cell.

Uses with Spectrally Orthogonal Polypeptides

The inventive polypeptides provided herein can be used alone or in combination with other polypeptides, such as blue-shifted optical reporters or optical actuators. In certain embodiments, the polypeptides provided herein are used in combination with second polypeptide that is spectrally orthogonal, for example, another polypeptide that is excitable with a different range of wavelengths such as blue light, thereby making the combination of the polypeptides useful as tools for all-optical electrophysiology. In certain embodiments, the the polypeptides provided herein can be co-expressed with a blue light-activated polypeptide. In certain embodiments, the two polypeptides are co-expressed in the cell membrane. In certain embodiments, the second polypeptide is blue-shifted optical actuator.

For example, the inventive polypeptides used in combination with a spectrally orthogonal polypeptide would be useful to probe neuronal excitation across spatial and temporal scales, for example, in cellular systems ranging from single dendritic spines to fields containing dozens of neurons measured in parallel, and from microsecond delays associated with action potential propagation to days-long changes in excitability.

In certain embodiments, the polypeptides provided herein, alone or in combination with other polypeptides, are useful for studying the excitability in human induced pluripotent stem cell (hiPSC)-derived neurons and in tissue such as brain tissue.

Provided herein are methods for characterizing cellular physiology by incorporating into an electrically excitable cell an optical reporter of, and an optical actuator of, electrical activity. A signal is obtained from the optical reporter in response to a stimulation of the cell. Either or both of the optical reporter and actuator may be based on genetically-encoded rhodopsins incorporated into the cell. Provided are all optical methods that may be used instead of, or as a complement to, traditional patch clamp technologies and that can provide rapid, accurate, and flexible assays of cellular physiology.

In certain embodiments, provided is a method for characterizing a cell, the method comprising incorporating into an electrically excitable cell an optical actuator of, and an optical reporter of, electrical activity; obtaining a signal from the optical reporter in response to a stimulation of the cell; and evaluating the signal, thereby characterizing the cell. In certain embodiments, provided is a method for characterizing a cell, the method comprising incorporating into an electrically excitable cell an optical actuator of, and an optical reporter of, electrical activity; obtaining a signal from the optical reporter in response to a stimulation of the cell; and evaluating the signal, thereby characterizing the cell, wherein the optical reporter is any one of the inventive polypeptides described herein.

In certain embodiments, the optical reporter is a polypeptide comprising an amino acid sequence of SEQ ID NO: 1, wherein the amino acid sequence comprises at least one mutation selected from P60S, T80S, D95H, D106H, and F161V. In certain embodiments, the optical reporter is a polypeptide comprising an amino acid sequence of SEQ ID NO: 1, wherein the amino acid sequence comprises at least one mutation selected from P60S, T80S, D95Q, D106H, and F161V. In certain embodiments, the optical reporter is a polypeptide comprising an amino acid sequence of SEQ ID NO: 1, wherein the amino acid sequence comprises a mutation at position 95, and at least one mutation selected from P60S, T80S, D106H, and F161V. In certain embodiments, the optical reporter is a polypeptide comprising an amino acid sequence of SEQ ID NO: 1, a D106H mutation, and at least one mutation selected from P60S, T80S, and F161V. In certain embodiments, the optical reporter is a polypeptide comprising an amino acid sequence of SEQ ID NO: 2 or a sequence that is at least about 80% homologous or identical to SEQ ID NO: 2. In certain embodiments, the optical reporter is a polypeptide comprising an amino acid sequence of SEQ ID NO: 3 or a sequence that is at least about 80% homologous or identical to SEQ ID NO: 3. In certain embodiments, incorporating the actuator and reporter into the cell comprises transforming the electrically active cell with a vector that includes a nucleic acid encoding the optical actuator of, and the optical reporter of, electrical activity. In certain embodiments, the method further comprises obtaining a somatic cell and converting the somatic cell into the electrically excitable cell.

In certain embodiments, converting the somatic cell into the electrically active cell comprises one selected from the list consisting of: direct conversion; and via an iPS intermediary. In certain embodiments, the electrically excitable cell is derived from a human embryonic stem cell. In certain embodiments, the electrically excitable cell is one selected from the list consisting of a neuron, a cardiomyocyte, and a glial cell. In certain embodiments, the optical actuator initiates an action potential in response to the stimulation. In certain embodiments, the stimulation comprises illuminating the cell. In certain embodiments, illuminating the cell is done using spatially resolved light from a digital micromirror array. In certain embodiments, the excitation of, and the signal from, the optical reporter comprise light that does not stimulate the cell. In certain embodiments, illuminating the cell and obtaining the signal are done simultaneously.

The optical actuator may be a genetically-encoded rhodopsin or modified rhodopsin such as a microbial channelrhodopsin. For example, sdChR, a channelrhodopsin from *Scherffelia dubia*, may be used or an improved version of sdChR—dubbed CheRiff—may be used as an optical actuator. "CheRiff" refers to a version of sdChR that uses mouse codon optimization, a trafficking sequence, and the mutation E154A. CheRiff is a blue-light activated channelrhopdopsin (excitation peak of 474 nm). CheRiff has been described in U.S. patent application Ser. No. 14/303,178, incorporated herein by reference in its entirety. The optical actuator generally carries current densities sufficient to induce action potentials (APs) when only a subsection of a cell is excited. For example, light used for imaging the reporter generally does not activate the actuator, and light used for activating the actuator generally does not confound the fluorescence signal of the reporter. Thus in an embodiment, an optical actuator and an optical reporter are spectrally orthogonal to avoid crosstalk and allow for simultaneous use.

In certain embodiments, the optical actuator comprises a modified rhodopsin. In certain embodiments, the optical actuator comprises CheRiff. In certain embodiments, the optical reporter comprises a rhodopsin that has been modified for voltage-sensitive fluorescence and absence of a steady-state photocurrent. In certain embodiments, the optical reporter comprises an inventive polypeptide as described herein.

In certain embodiments, the method further comprises obtaining a control cell and observing a control signal generated by a control optical reporter in the control cell. In certain embodiments, obtaining the control cell comprises editing a genome from the cell such that the control cell and the cell are isogenic but for a mutation. In certain embodiments, obtaining the signal comprises observing a cluster of different cells with a microscope and using a computer to isolate the signal generated by the optical reporter from a plurality of signals from the different cells. In certain embodiments, the computer isolates the signal by performing an independent component analysis and identifying a spike train associated with the cell. In certain embodiments, further comprising using the microscope to obtain an image of a plurality of clusters of cells.

In certain embodiments, the observed signal comprises a probability of a voltage spike in response to the stimulation of the cell. In certain embodiments, the observed signal comprises a changed probability of a voltage spike in response to the stimulation of the cell relative to a control. In certain embodiments, the observed signal comprises a change in the waveform of a voltage spike. In certain embodiments, the observed signal comprises a sub-threshold increase in the membrane potential. In certain embodiments, the observed signal comprises a decrease in the membrane potential.

In certain embodiments, characterizing the cell comprises diagnosing a disease. In certain embodiments, the disease is selected from the group consisting of Cockayne syndrome, Down Syndrome, Dravet syndrome, familial dysautonomia, Fragile X Syndrome, Friedreich's ataxia, Gaucher disease, hereditary spastic paraplegias, Machado-Joseph disease, Phelan-McDermid syndrome (PMDS), polyglutamine (polyQ)-encoding CAG repeats, spinal muscular atrophy, Timothy syndrome, Alzheimer's disease, frontotemporal lobar degeneration, Huntington's disease, multiple sclerosis, Parkinson's disease, spinal and bulbar muscular atrophy, and amyotrophic lateral sclerosis.

In certain embodiments, characterizing the cell comprises evaluating a response of the cell to exposure to a compound. In certain embodiments, characterizing the cell further comprises measuring a concentration of an ion. In certain embodiments, characterizing the cell comprises determining progress of a treatment. In certain embodiments, the method further comprising editing the genome of the electrically active cells.

Also provided herein is a method for characterizing an interaction between cells, the method comprising: incorporating into a first electrically excitable cell an optical actuator of electrical activity incorporating into a second electrically excitable cell an optical reporter of electrical activity; culturing the first electrically excitable cell and the second electrically excitable cell in proximity to one another, obtaining a signal from the optical reporter in response to a stimulation of the first electrically excitable cell; and evaluating the signal, thereby characterizing an interaction between the first electrically excitable cell and the second electrically excitable cell.

In certain embodiments, the first electrically excitable cell and the second electrically excitable cell are of the same cell type. In certain embodiments, the cell type is one selected from the list consisting of a neuron, a cardiomyocyte, and a glial cell.

In certain embodiments, the first electrically excitable cell and the second electrically excitable cell are each of a different cell type.

In certain embodiments, the characterized interaction comprises excitatory neurotransmission. In certain embodiments, the characterized interaction comprises inhibitory neurotransmission. In certain embodiments, characterizing the interaction comprises measurement of conduction velocity of cardiac action potential. In certain embodiments, incorporating the actuator into the first electrically excitable cell comprises transforming first electrically excitable cell with a vector that includes a nucleic acid encoding the optical actuator of electrical activity.

In certain embodiments, incorporating the reporter into the second electrically excitable cell comprises transforming the second electrically excitable cell with a vector that includes a nucleic acid encoding the optical reporter of, electrical activity.

In certain embodiments, the method further comprising obtaining somatic cells and converting the somatic cells into the first electrically excitable cell and the second electrically excitable cell.

In certain embodiments, converting the somatic cells comprises one selected from the list consisting of: direct conversion; and via an iPS intermediary. In certain embodiments, the first electrically excitable cell and the second electrically excitable cell are derived from a human embryonic stem cell.

In certain embodiments, the optical actuator initiates an action potential in response to the stimulation. In certain embodiments, the stimulation comprises illuminating the first electrically excitable cell. In certain embodiments, the illuminating is done using spatially resolved light from a digital micromirror array. In certain embodiments, the excitation of, and the signal from, the optical reporter comprise light that does not stimulate the first electrically excitable cell. In certain embodiments, the illuminating and obtaining the signal are done simultaneously. In certain embodiments, the optical actuator comprises a modified rhodopsin. In certain embodiments, the optical actuator comprises CheRiff.

In certain embodiments, the optical reporter comprises a rhodopsin that has been modified for voltage-sensitive fluorescence and absence of a steady-state photocurrent. In certain embodiments, the optical reporter comprises an inventive polypeptide as described herein.

In certain embodiments, obtaining the signal comprises observing a cluster of different cells with a microscope and using a computer to isolate the signal generated by the optical reporter from a plurality of signals from the different cells.

In certain embodiments, the computer isolates the signal by performing an independent component analysis and identifying a spike train associated with the second electrically excitable cell. In certain embodiments, the method further comprising using the microscope to obtain an image of a plurality of clusters of cells.

In certain embodiments, the observed signal comprises a probability of a voltage spike in response to the stimulation of the cell. In certain embodiments, the observed signal comprises a changed probability of a voltage spike in response to the stimulation of the cell relative to a control. In certain embodiments, the observed signal comprises a change in the waveform of a voltage spike.

In certain embodiments, the observed signal comprises a sub-threshold increase in the membrane potential. In certain embodiments, the observed signal comprises a decrease in the membrane potential.

In certain embodiments, characterizing the interaction comprises diagnosing a disease. In certain embodiments, characterizing the interaction comprises evaluating a cellular response to exposure to a compound. In certain embodiments, characterizing the interaction comprises determining progress of a treatment. In certain embodiments, the method further comprising editing the genome of the electrically active cells.

Other Uses of the Inventive Polypeptides

The polypeptides provided herein are useful for studying bioelectric phenomena such as neuronal or cardiac activity. For example, the proteins are useful in reporting action potentials in cultured neurons.

The constructs disclosed in the present application can be used in methods for drug screening, e.g., for drugs targeting the nervous system or for agents that affect the membrane potential of one or more of the intracellular membranes. In a culture of cells expressing specific ion channels, one can screen for agonists or antagonists without the labor of applying patch clamp to cells one at a time. In neuronal cultures one can probe the effects of drugs on action potential initiation, propagation, and synaptic transmission. Application in human induced pluripotent stem cells (iPSC)-derived neurons will enable studies on genetically determined neurological diseases, as well as studies on the response to environmental stresses (e.g., anoxia).

Similarly, the optical voltage sensing using the constructs provided herein provides a new and much improved methods to screen for drugs that modulate the cardiac action potential and its intercellular propagation. These screens will be useful both for determining safety of candidate drugs and to identify new cardiac drug leads. Identifying drugs that interact with the hERG channel is a particularly promising direction because inhibition of hERG is associated with ventricular fibrillation in patients with long QT syndrome. Application in human iPSC-derived cardiomyocytes will enable studies on genetically determined cardiac conditions, as well as studies on the response to environmental stresses (e.g., anoxia).

Additionally, the constructs of the present invention can be used in methods to study of development and wound healing. The role of electrical signaling in normal and abnormal development, as well as tissue repair, is poorly understood. VIPs enable studies of voltage dynamics over long times in developing or healing tissues, organs, and organisms, and lead to drugs that modulate these dynamics.

In yet another embodiment, the invention provides methods to screen for drugs that affect membrane potential of mitochondria. Mitochondria play an essential role in ageing, cancer, and neurodegenerative diseases. Currently there is no good probe for mitochondrial membrane potential. VIPs provide such a probe, enabling searches for drugs that modulate mitochondrial activity.

The invention further provides methods to screen for drugs that modulate the electrophysiology of a wide range of medically, industrially, and environmentally significant microorganisms.

Prior to our discovery of VIPs, no measurement of membrane potential had been made in any intact prokaryote. We discovered that bacteria have complex electrical dynamics. VIPs enable screens for drugs that modulate the electrophysiology of a wide range of medically, industrially, and environmentally significant microorganisms. For instance, we found that electrical activity is correlated with efflux pumping in *E. coli*.

Changes in membrane potential are also associated with activation of macrophages. However, this process is poorly understood due to the difficulty in applying patch clamp to motile cells. VIPs enable studies of the electrophysiology of macrophages and other motile cells, including sperm cells for fertility studies. Thus the VIPs of the invention can be used in methods to screen for drugs or agents that affect, for example, immunity and immune diseases, as well as fertility.

The examples describe expression of VIPs in rat hippocampal neurons, mouse HL-1 cardiomyocytes, and human iPS-derived cardiomyocytes. In all cell types, single action potentials (APs) were readily observed. We tested the effects of drugs on the AP waveform.

For example, in one embodiment, the invention provides a method wherein the cell expressing a microbial rhodopsin is further exposed to a stimulus capable of or suspected to be capable of changing membrane potential.

Stimuli that can be used include candidate agents, such as drug candidates, small organic and inorganic molecules, larger organic molecules and libraries of molecules and any combinations thereof. One can also use a combination of a known drug, such as an antibiotic with a candidate agent to screen for agents that may increase the effectiveness of the one or more of the existing drugs, such as antibiotics.

The methods of the invention are also useful for vitro toxicity screening and drug development. For example, using the methods described herein one can make a human cardiomyocyte from induced pluripotent cells that stably express a modified archaerhodopsin wherein the proton pumping activity is substantially reduced or abolished. Such cells are particularly useful for in vitro toxicity screening in drug development.

General Experimental Methods

The invention provides method for measuring membrane potential in a cell expressing a nucleic acid encoding a microbial rhodopsin protein, the method comprising the steps of (a) exciting at least one cell comprising a nucleic acid encoding a microbial rhodopsin protein with light of at least one wavelength; and (b) detecting at least one optical signal from the at least one cell, wherein the level of fluorescence emitted by the at least one cell compared to a reference is indicative of the membrane potential of the cell.

The term "reference" as used herein refers to a baseline value of any kind that one skilled in the art can use in the methods. In some embodiments, the reference is a cell that has not been exposed to a stimulus capable of or suspected to be capable of changing membrane potential. In one embodiment, the reference is the same cell transfected with the microbial rhodopsin but observed at a different time point.

In the methods of the invention, the cells are excited with a light source so that the emitted fluorescence can be detected. The wavelength of the excitation light depends on the fluorescent molecule. For example, the archerhodopsin constructs in the examples are all excitable using light with wavelengths varying between 594 nm and 690 nm or 594 nm to 645 nm. Alternatively, the range may be between 630 nm to 645 nm. For example a commonly used Helium Neon laser emits at 632.8 nm and can be used in excitation of the fluorescent emission of these molecules.

In some embodiments a second light is used. For example, if the cell expresses a reference fluorescent molecule or a fluorescent molecule that is used to detect another feature of the cell, such a pH or Calcium concentration. In such case, the second wavelength differs from the first wavelength. Examples of useful wavelengths include wavelengths in the range of 447-594 nm, for example, 473 nm, 488 nm, 514 nm, 532 nm, and 561 nm.

The hardware and software needed to take maximal advantage of VIPs depends on the type of assay, and can be easily optimized and selected by a skilled artisan based on the information provided herein. Existing instrumentation can be easily used or adapted for the detection of VIPs. The factors that determine the type of instrumentation include, precision and accuracy, speed, depth penetration, multiplexing and throughput. A general discussion is provided in US Publication No. 20130224756, incorporated herein by reference in its entirety.

The spectroscopic states of microbial rhodopsins are typically classified by their absorption spectrum. However, in some cases there is insufficient protein in a single cell to detect spectral shifts via absorbance alone. Any of the exemplary several optical imaging techniques known in the art (see, e.g., US Publication No. 20130224756, incorporated herein by reference in its entirety) can be used to probe other state-dependent spectroscopic properties.

Uses and Applications of the Voltage-Indicating Proteins

Provided herein are areas in which the voltage-indicating proteins, the polynucleotides, the nucleic acid constructs, the vectors, and cells can be applied both in commercial and scientific endeavors.

The present invention can be useful in screening drugs. A recent article reported that "Among the 100 top-selling drugs, 15 are ion-channel modulators with a total market value of more than \$15 billion." (Molokanova, E. & Savchenko, A. *Drug Discov. Today* 13, 14-22 (2008)). However, searches for new ion-channel modulators are limited by the absence of good indicators of membrane potential (Przybylo, M., et al. *J. Fluoresc.*, 1-19 (2010)). In some embodiments, the optical sensors described herein are used to measure or monitor membrane potential changes in response to a candidate ion channel modulator. Such screening methods can be performed in a high throughput manner by simultaneously screening multiple candidate ion channel modulators in cells.

The present invention can be useful with stem cells. Many genetically determined diseases of the nervous system and heart lack good animal models. In some embodiments, the VIPs described herein are expressed in stem cells, either induced pluripotent or stem cells isolated from cord blood or amniotic fluid, or embryonic stem cells derived from humans or fetuses known to carry or be affected with a genetic defect. In some embodiments, the embryonal stem cells are of non-human origin. Alternatively the VIPs are expressed in progeny of the stem cells, either progenitor cells or differentiated cell types, such as cardiac or neuronal cells. Expression of voltage indicators in these cell types provides information on the electrophysiology of these cells and the response of membrane potential to candidate agents or to changes in ambient conditions (e.g., anoxia). Additionally, expression of VIPs in stem cells enables studies of the differentiation and development of stem cells into electrically active cell types and tissues.

Stem cells may be isolated and manipulated according to methods known to one skilled in the art. Patents describing methods of making and using, e.g., primate embryonic stem cells are described in, e.g., U.S. Pat. Nos. 7,582,479; 6,887,706; 6,613,568; 6,280,718; 6,200,806; and 5,843,780. Additionally, for example, human cord blood derived unrestricted somatic stem cells are described in U.S. Pat. No. 7,560,280 and progenitor cells from wharton's jelly of human umbilical cord in U.S. Pat. No. 7,547,546.

Induced pluripotent stem cells may be produced by methods described, for example, in U.S. Patent Application Publication No. 20110200568, European Patent Application Publication No. 01970446, and U.S. Patent Application Publication No. US2008/0233610. Additional methods for making and using induced pluripotent stem cells are also described in application U.S. Ser. No. 10/032,191, titled "Methods for cloning mammals using reprogrammed donor chromatin or donor cells," and Ser. No. 10/910,156, "Methods for altering cell fate." These patent applications relate to technology to alter the state of a cell, such as a human skin cell, by exposing the cell's DNA to the cytoplasm of another reprogramming cell with differing properties. Detailed description of the reprogramming factors used in making induced pluripotent stem cells, including expression of genes OCT4, SOX2, NANOG, cMYC, LIN28 can also be found, for example, in PCT/US2006/030632.

Methods for differentiating stem cells or pluripotent cells into differentiated cells are also well known to one skilled in the art.

The present invention is also useful in brain imaging. The human brain functions by sending electrical impulses along its $\sim 10^{11}$ neurons. These patterns of firing are the origin of every human thought and action. Yet there is currently no good way to observe large-scale patterns of electrical activity in an intact brain (Baker, B. J. et al. *J. Neurosci. Methods* 161, 32-38 (2007); Baker, B. J. et al. *Brain Cell Biology* 36, 53-67 (2008)).

The VIPs can lead to unprecedented insights in neuroscience. The device can allow mapping of brain activity in patients and/or cells of patients with psychiatric and neurological diseases, and in victims of traumatic injuries or animal models modeling such diseases and injuries.

Optical imaging of neuronal activity can also form the basis for improved brain-machine interfaces for people with disabilities. For imaging in the brain, the VIP is administered by direct injection into the site to be analyzed (with or without accompanying electroporation) or the VIP is delivered using a viral vector. Alternatively the optical sensor may be administered through the formation of a transgenic organism, or through application of the Cre-Lox recombination system.

The present invention also has uses in microbiology. Bacteria are host to dozens of ion channels of unknown function (Martinac, B., et al. *Physiol. Rev.* 88, 1449 (2008)). Most bacteria are too small for direct electrophysiological measurements, so their electrical properties are almost entirely unknown.

Upon expressing PROPS (see, e.g., US 2013/0224756, incorporated by reference in its entirety) in *E. coli*, it was found that *E. coli* undergo a previously unknown electrical spiking behavior. The data described herein in the Examples section is the first report of spontaneous electrical spiking in any bacterium. This result establishes the usefulness of voltage sensors in microbes.

Furthermore, the electrical spiking in *E. coli* was found to be coupled to efflux of a cationic membrane permeable dye. It is thus plausible that electrical spiking is correlated to efflux of other cationic compounds, including antibiotics. VIPs may prove useful in screens for inhibitors of antibiotic efflux.

VIPs will unlock the electrophysiology of the millions of species of microorganisms which have proven too small to probe via conventional electrophysiology. This information will be useful for understanding the physiology of bacteria with medical, industrial, and ecological applications.

The present invention is also useful in the area of mitochondria and metabolic diseases. Mitochondria are membrane-bound organelles which act as the ATP factories in eukaryotic cells. A membrane voltage powers the mitochondrial ATP synthase. Dysfunction of mitochondria has been implicated in a variety of neurodegenerative diseases, diabetes, cancer, cardiovascular disease, and aging. Thus there is tremendous interest in measuring mitochondrial membrane potential in vivo, although currently available techniques are severely limited (Verburg, J. & Hollenbeck, P. *J. J. Neurosci.* 28, 8306 (2008); Ichas, F., et al. *Cell* 89, 1145-1154 (1997); Johnson, L. V., et al. *Proc. Natl. Acad. Sci. U.S.A.* 77, 990 (1980)).

The exemplary VIPs described herein (PROPS) can be tagged with peptide sequences that direct it to the mitochondrial inner membrane (Hoffmann, A., et al. *Proc. Nat. Acad. Sci. U.S.A.* 91, 9367 (1994)) or the mitochondrial outer membrane, where it serves as an optical indicator of mitochondrial membrane potential.

The present invention is also useful for imaging purposes in cells, such as human cells and vertebrate models (e.g., rat, mouse, zebrafish). For example, The membrane potential of a mammalian cell can be detected using the archaerhodopsin variants of the inventive polypeptides.

The present invention is also useful in gene delivery methods. The polynucleotides encoding the archaerhodopsin polypeptides of the invention are introduced to the cell or organ or organism of interest using routine gene delivery methods. They are administered to a subject for the purpose of imaging membrane potential changes in cells of a subject. In one embodiment, the optical sensors are introduced to the cell via expression vectors.

The various gene delivery methods currently being applied to stem cell engineering include viral and non viral vectors, as well as biological or chemical methods of transfection. The methods can yield either stable or transient gene expression in the system used.

The present invention can also be used in viral gene delivery systems. Because of their high efficiency of transfection, genetically modified viruses have been widely applied for the delivery of genes into stem cells.

The present invention can also be used in DNA virus vectors, for example, adenovirus and adeno-associated virus. Adenoviruses are double stranded, nonenveloped and icosahedral viruses containing a 36 kb viral genome (Kojaoghlanian et al., 2003). Their genes are divided into early (E1A, E1B, E2, E3, E4), delayed (IX, IVa2) and major late (L1, L2, L3, L4, L5) genes depending on whether their expression occurs before or after DNA replication. More than 51 human adenovirus serotypes have been described which can infect and replicate in a wide range of organs. The viruses are classified into the following subgroups: A—induces tumor with high frequency and short latency, B—are weakly oncogenic, and C—are non-oncogenic (Cao et al., 2004; Kojaoghlanian et al., 2003).

These viruses have been used to generate a series of vectors for gene transfer cellular engineering. The initial generation of adenovirus vectors were produced by deleting the E1 gene (required for viral replication) generating a vector with a 4 kb cloning capacity. An additional deletion of E3 (responsible for host immune response) allowed an 8 kb cloning capacity (Bett et al., 1994; Danthinne and Imperiale, 2000; Danthinne and Werth, 2000). The second generation of vectors was produced by deleting the E2 region (required for viral replication) and/or the E4 region (participating in inhibition of host cell apoptosis) in conjunction with E1 or E3 deletions. The resultant vectors have a cloning capacity of 10-13 kb (Armentano et al., 1995). The third "gutted" generation of vectors was produced by deletion of the entire viral sequence with the exception of the inverted terminal repeats (ITRs) and the cis acting packaging signals. These vectors have a cloning capacity of 25 kb (Kochanek et al., 2001) and have retained their high transfection efficiency both in quiescent and dividing cells.

Importantly, the adenovirus vectors do not normally integrate into the genome of the host cell, but they have shown efficacy for transient gene delivery into adult stem cells. These vectors have a series of advantages and disadvantages. An important advantage is that they can be amplified at high titers and can infect a wide range of cells (Benihoud et al., 1999; Kanerva and Hemminki, 2005). The vectors are generally easy to handle due to their stability in various storing conditions. Adenovirus type 5 (Ad5) has been successfully used in delivering genes in human and mouse stem cells (Smith-Arica et al., 2003). The lack of adenovirus integration into host cell genetic material can in many instances be seen as a disadvantage, as its use allows only transient expression of the therapeutic gene.

The following provides examples to show that a skilled artisan can readily transducer cells with contructs expressing microbial rhodopsins of the present invention to eukaryotic, such as mammalian cells. For example in a study evaluating the capacity of mesenchymal stem cells to undergo chondrogenesis when TGF-beta1 and bone morphogencic protein-2 (BMP-2) were delivered by adenoviral-mediated expression, the chondrogenesis was found to closely correlated with the level and duration of the transiently expressed proteins. Transgene expression in all aggregates was highly transient, showing a marked decrease after 7 days. Chondrogenesis was inhibited in aggregates modified to express >100 ng/ml TGF-beta1 or BMP-2; however, this was partly due to the inhibitory effect of exposure to high adenoviral loads (Mol. Ther. 2005 August; 12 (2):219-28. Gene-induced chondrogenesis of primary mesenchymal stem cells in vitro. Palmer G D, Steinert A, Pascher A, Gouze E, Gouze J N, Betz O, Johnstone B, Evans C H, Ghivizzani S C). In a second model using rat adipose derived stem cells transduced with adenovirus carrying the recombinant human bone morphogenic protein-7 (BMP-7) gene showed promising results for an autologous source of stem cells for BMP gene therapy. However, activity assessed by measuring alkaline phosphatase in vitro was transient and peaked on day 8. Thus the results were similar to those found in the chondrogenesis model (Cytotherapy. 2005; 7 (3):273-81).

Thus for experiments that do not require stable gene expression adenovirus vectors is a good option.

Adenovirus vectors based on Ad type 5 have been shown to efficiently and transiently introduce an exogenous gene via the primary receptor, coxsackievirus, and adenovirus receptor (CAR). However, some kinds of stem cells, such as MSC and hematopoietic stem cells, cannot be efficiently transduced with conventional adenovirus vectors based on Ad serotype 5 (Ad5), because of the lack of CAR expression. To overcome this problem, fiber-modified adenovirus vectors and an adenovirus vector based on another serotype of adenovirus have been developed. (Mol. Pharm. 2006 March-April; 3 (2):95-103. Adenovirus vector-mediated gene transfer into stem cells. Kawabata K, Sakurai F, Koizumi N, Hayakawa T, Mizuguchi H. Laboratory of Gene Transfer and Regulation, National Institute of Biomedical Innovation, Osaka 567-0085, Japan).

Such modifications can be readily applied to the use of the microbial rhodopsin constructs described herein, particularly in the applications relating to stem cells.

Other applications include adeno-associated viruses (AAV), which are ubiquitous, noncytopathic, replication-incompetent members of ssDNA animal virus of parvoviridae family (G. Gao et al., New recombinant serotypes of AAV vectors. Curr Gene Ther. 2005 June; 5 (3):285-97). AAV is a small icosahedral virus with a 4.7 kb genome. These viruses have a characteristic termini consisting of palindromic repeats that fold into a hairpin. They replicate with the help of helper virus, which are usually one of the many serotypes of adenovirus. In the absence of helper virus they integrate into the human genome at a specific locus (AAVS1) on chromosome 19 and persist in latent form until helper virus infection occurs (Atchison et al., 1965, 1966). AAV can transduce cell types from different species including mouse, rat and monkey. Among the serotypes, AAV2 is the most studied and widely applied as a gene delivery vector. Its genome encodes two large opening reading frames (ORFs) rep and cap. The rep gene encodes four proteins Rep 78, Rep 68, Rep 52 and Rep 40 which play important roles in various stages of the viral life cycle (e.g. DNA replication, transcriptional control, site specific integration, accumulation of single stranded genome used for viral packaging). The cap gene encodes three viral capsid proteins VP1, VP2, VP3 (Becerra et al., 1988; Buning et al., 2003). The genomic 3' end serves as the primer for the second strand synthesis and has terminal resolution sites (TRS) which serve as the integration sequence for the virus as the sequence is identical to the sequence on chromosome 19 (Young and Samulski, 2001; Young et al., 2000).

These viruses are similar to adenoviruses in that they are able to infect a wide range of dividing and non-dividing cells. Unlike adenovirus, they have the ability to integrate into the host genome at a specific site in the human genome. Unfortunately, due to their rather bulky genome, the AAV vectors have a limited capacity for the transfer of foreign gene inserts (Wu and Ataai, 2000).

The present invention can be used in RNA virus vectors such as retroviruses and lentiviruses. Retroviral genomes consist of two identical copies of single stranded positive sense RNAs, 7-10 kb in length coding for three genes; gag, pol and env, flanked by long terminal repeats (LTR) (Yu and Schaffer, 2005). The gag gene encodes the core protein capsid containing matrix and nucleocapsid elements that are cleavage products of the gag precursor protein. The pol gene codes for the viral protease, reverse transcriptase and integrase enzymes derived from gag-pol precursor gene. The env gene encodes the envelop glycoprotein which mediates viral entry. An important feature of the retroviral genome is the presence of LTRs at each end of the genome. These sequences facilitate the initiation of viral DNA synthesis, moderate integration of the proviral DNA into the host genome, and act as promoters in regulation of viral gene transcription. Retroviruses are subdivided into three general groups: the oncoretroviruses (Maloney Murine Leukenmia Virus, MoMLV), the lentiviruses (HIV), and the spumaviruses (foamy virus) (Trowbridge et al., 2002).

Retroviral based vectors are the most commonly used integrating vectors for gene therapy. These vectors generally have a cloning capacity of approximately 8 kb and are generated by a complete deletion of the viral sequence with the exception of the LTRs and the cis acting packaging signals.

The retroviral vectors integrate at random sites in the genome. The problems associated with this include potential insertional mutagenesis, and potential oncogenic activity driven from the LTR. The U3 region of the LTR harbors promoter and enhancer elements, hence this region when deleted from the vector leads to a self-inactivating vector where LTR driven transcription is prevented. An internal promoter can then be used to drive expression of the transgene.

The initial studies of stem cell gene transfer in mice raised the hope that gene transfer into humans would be equally as efficient (O'Connor and Crystal, 2006). Gene transfer using available retroviral vector systems to transfect multi-lineage long-term repopulating stem cells is still significantly more efficient in the mouse.

Lentiviruses are members of Retroviridae family of viruses (M. Scherr et al., Gene transfer into hematopoietic stem cells using lentiviral vectors. Curr Gene Ther. 2002 February; 2 (1):45-55). They have a more complex genome and replication cycle as compared to the oncoretroviruses (Beyer et al., 2002). They differ from simpler retroviruses in that they possess additional regulatory genes and elements, such as the tat gene, which mediates the transactivation of viral transcription (Sodroski et al., 1996) and rev, which mediates nuclear export of unspliced viral RNA (Cochrane et al., 1990; Emerman and Temin, 1986).

Lentivirus vectors are derived from the human immunodeficiency virus (HIV-1) by removing the genes necessary for viral replication rendering the virus inert. Although they are devoid of replication genes, the vector can still efficiently integrate into the host genome allowing stable expression of the transgene. These vectors have the additional advantage of a low cytotoxicity and an ability to infect diverse cell types. Lentiviral vectors have also been developed from Simian, Equine and Feline origin but the vectors derived from Human Immunodeficiency Virus (HIV) are the most common (Young et al., 2006).

Lentivirus vectors are generated by deletion of the entire viral sequence with the exception of the LTRs and cis acting packaging signals. The resultant vectors have a cloning capacity of about 8 kb. One distinguishing feature of these vectors from retroviral vectors is their ability to transduce dividing and non-dividing cells as well as terminally differentiated cells (Kosaka et al., 2004). The lentiviral delivery system is capable of high infection rates in human mesenchymal and embryonic stem cells. In a study by Clements et al., the lentiviral backbone was modified to express mono- and bi-cistronic transgenes and was also used to deliver short hairpin ribonucleic acid for specific silencing of gene expression in human stem cells. (*Tissue Eng.* 2006 July; 12 (7):1741-51. Lentiviral manipulation of gene expression in human adult and embryonic stem cells. Clements M O, Godfrey A, Crossley J, Wilson S J, Takeuchi Y, Boshoff C).

The table below summarizes various characteristics of the viral vectors.

| Vector | Insert capacity (kb) | Tropism | Vector genome form | Expression | Efficiency |
|---|---|---|---|---|---|
| Enveloped | | | | | |
| Retrovirus | 8 | Dividing cells only | Integrated | Stable | High |
| Lentivirus | 8 | Dividing and non-dividing | Integrated | Stable | High |
| Non-enveloped | | | | | |
| Adeno-associated virus | <5 | Dividing and non-dividing | Episomal and integrated | Stable | High |
| Adenovirus | 2-24 | Dividing and non-dividing | Episomal | Transient | High |

The present invention can also be used in non-viral gene delivery systems. For example, they are useful in methods for the facilitated integration of genes. In addition to the viral based vectors discussed above, other vector systems that lack viral sequence can be used. The alternative strategies include conventional plasmid transfer and the application of targeted gene integration through the use of integrase or transposase technologies. These represent important new approaches for vector integration and have the advantage of being both efficient, and often site specific in their integration. Currently three recombinase systems are available for genetic engineering: cre recombinase from phage P1 (Lakso et al., 1992; Orban et al., 1992), FLP (flippase) from yeast 2 micron plasmid (Dymecki, 1996; Rodriguez et al., 2000), and an integrase isolated from streptomyses phage I C31 (Ginsburg and Calos, 2005). Each of these recombinases recognize specific target integration sites. Cre and FLP recombinase catalyze integration at a 34 bp palindromic sequence called lox P (locus for crossover) and FRT (FLP recombinase target) respectively. Phage integrase catalyzes site-specific, unidirectional recombination between two short att recognition sites in mammalian genomes. Recombination results in integration when the att sites are present on two different DNA molecules and deletion or inversion when the att sites are on the same molecule. It has been found to function in tissue culture cells (in vitro) as well as in mice (in vivo).

The Sleeping Beauty (SB) transposon is comprised of two inverted terminal repeats of 340 base pairs each (Izsvak et al., 2000). This system directs the precise transfer of specific constructs from a donor plasmid into a mammalian chromosome. The excision and integration of the transposon from a plasmid vector into a chromosomal site is mediated by the SB transposase, which can be delivered to cells as either in a cis or trans manner (Kaminski et al., 2002). A gene in a chromosomally integrated transposon can be expressed over the lifetime of a cell. SB transposons integrate randomly at TA-dinucleotide base pairs although the flanking sequences can influence integration.

Methods to Introduce or Deliver Vectors into Cells

There are various methods known in the art for introducing vectors into cells. For example, electroporation relies on the use of brief, high voltage electric pulses which create transient pores in the membrane by overcoming its capacitance. One advantage of this method is that it can be utilized for both stable and transient gene expression in most cell types. The technology relies on the relatively weak nature of the hydrophobic and hydrophilic interactions in the phospholipid membrane and its ability to recover its original state after the disturbance. Once the membrane is permeabilized, polar molecules can be delivered into the cell with high efficiency. Large charged molecules like DNA and RNA move into the cell through a process driven by their electrophoretic gradient. The amplitude of the pulse governs the total area that would be permeabilized on the cell surface and the duration of the pulse determines the extent of permeabilization (Gabriel and Teissie, 1997). The permeabilized state of the cell depends on the strength of the pulses. Strong pulses can lead to irreversible permeabilization, irreparable damage to the cell and ultimately cell death. For this reason electroporation is probably the harshest of gene delivery methods and it generally requires greater quantities of DNA and cells. The effectiveness of this method depends on many crucial factors like the size of the cell, replication and temperature during the application of pulse (Rols and Teissie, 1990).

The most advantageous feature of this technique is that DNA can be transferred directly into the nucleus increasing its likelihood of being integrated into the host genome. Even cells difficult to transfect can be stably transfected using this method (Aluigi et al., 2005; Zernecke et al., 2003). Modification of the transfection procedure used during electroporation has led to the development of an efficient gene transfer method called nucleofection. The Nucleofector™ technology, is a non-viral electroporation-based gene transfer technique that has been proven to be an efficient tool for transfecting hard-to-transfect cell lines and primary cells including MSC (Michela Aluigi, Stem Cells Vol. 24, No. 2, February 2006, pp. 454-461).

Biomolecule-based methods can also be used to introduce the polypeptides, polynucleotides, nucleic acid constructs and vectors into cells. For example, protein transduction domains (PTD) are short peptides that are transported into the cell without the use of the endocytotic pathway or protein channels. The mechanism involved in their entry is not well understood, but it can occur even at low temperature (Derossi et al. 1996). The two most commonly used naturally occurring PTDs are the trans-activating activator of transcription domain (TAT) of human immunodeficiency virus and the homeodomain of Antennapedia transcription factor. In addition to these naturally occurring PTDs, there are a number of artificial peptides that have the ability to spontaneously cross the cell membrane (Joliot and Prochiantz, 2004). These peptides can be covalently linked to the pseudo-peptide backbone of PNA (peptide nucleic acids) to help deliver them into the cell.

Other delivery methods include the use of liposomes, which are synthetic vesicles that resemble the cell membrane. When lipid molecules are agitated with water they spontaneously form spherical double membrane compartments surrounding an aqueous center forming liposomes. They can fuse with cells and allow the transfer of "packaged" material into the cell. Liposomes have been successfully used to deliver genes, drugs, reporter proteins and other biomolecules into cells (Felnerova et al., 2004). The advantage of liposomes is that they are made of natural biomolecules (lipids) and are nonimmunogenic.

Diverse hydrophilic molecules can be incorporated into them during formation. For example, when lipids with positively charged head group are mixed with recombinant DNA they can form lipoplexes in which the negatively charged DNA is complexed with the positive head groups of lipid molecules. These complexes can then enter the cell through the endocytotic pathway and deliver the DNA into lysosomal compartments. The DNA molecules can escape this compartment with the help of dioleoylethanolamine (DOPE) and are transported into the nucleus where they can be transcribed (Tranchant et al., 2004).

Despite their simplicity, liposomes suffer from low efficiency of transfection because they are rapidly cleared by the reticuloendothelial system due to adsorption of plasma proteins. Many methods of stabilizing liposomes have been used including modification of the liposomal surface with oligosaccharides, thereby sterically stabilizing the liposomes (Xu et al., 2002).

Immunoliposomes are liposomes with specific antibodies inserted into their membranes. The antibodies bind selectively to specific surface molecules on the target cell to facilitate uptake. The surface molecules targeted by the antibodies are those that are preferably internalized by the cells so that upon binding, the whole complex is taken up. This approach increases the efficiency of transfection by enhancing the intracellular release of liposomal components. These antibodies can be inserted in the liposomal surface through various lipid anchors or attached at the terminus of polyethylene glycol grafted onto the liposomal surface. In addition to providing specificity to gene delivery, the antibodies can also provide a protective covering to the liposomes that helps to limit their degradation after uptake by endogenous RNAses or proteinases (Bendas, 2001). To further prevent degradation of liposomes and their contents in the lysosomal compartment, pH sensitive immunoliposomes can be employed (Torchilin, 2006). These liposomes enhance the release of liposomal content into the cytosol by fusing with the endosomal membrane within the organelle as they become destabilized and prone to fusion at acidic pH.

In general non-viral gene delivery systems have not been as widely applied as a means of gene delivery into stem cells as viral gene delivery systems. However, promising results were demonstrated in a study looking at the transfection viability, proliferation and differentiation of adult neural stem/progenitor cells into the three neural lineages neurons. Non-viral, non-liposomal gene delivery systems (ExGen500 and FuGene6) had a transfection efficiency of between 16% (ExGen500) and 11% (FuGene6) of cells. FuGene6-treated cells did not differ from untransfected cells in their viability or rate of proliferation, whereas these characteristics were significantly reduced following ExGen500 transfection. Importantly, neither agent affected the pattern of differentiation following transfection. Both agents could be used to genetically label cells, and track their differentiation into the three neural lineages, after grafting onto ex vivo organotypic hippocampal slice cultures (J Gene Med. 2006 January; 8 (1):72-81. Efficient non-viral transfection of adult neural stem/progenitor cells, without affecting viability, proliferation or differentiation. Tinsley R B, Faijerson J, Eriksson P S).

Polymer-based methods can also be used for delivery. The protonated .epsilon.-amino groups of poly L-lysine (PLL) interact with the negatively charged DNA molecules to form complexes that can be used for gene delivery. These complexes can be rather unstable and showed a tendency to aggregate (Kwoh et al., 1999). The conjugation of polyethylene glycol (PEG) was found to lead to an increased stability of the complexes (Lee et al., 2005, Harada-Shiba et al., 2002). To confer a degree of tissue-specificity, targeting molecules such as tissue-specific antibodies have also been employed (Trubetskoy et al., 1992, Suh et al., 2001).

An additional gene carrier that has been used for transfecting cells is polyethylenimine (PEI) which also forms complexes with DNA. Due to the presence of amines with different pKa values, it has the ability to escape the endosomal compartment (Boussif et al., 1995). PEG grafted onto PEI complexes was found to reduce the cytotoxicity and aggregation of these complexes. This can also be used in combination with conjugated antibodies to confer tissue-specificity (Mishra et al., 2004, Shi et al., 2003, Chiu et al., 2004, Merdan et al., 2003).

Targeted gene delivery (site-specific recombinations) are also useful in delivery. In certain embodiments, a non-human, transgenic animal comprising a targeting vector that further comprises recombination sites (e.g., Lox sites, FRT sites) can be crossed with a non-human, transgenic animal comprising a recombinase (e.g., Cre recombinase, FLP recombinase) under control of a particular promoter. It has been shown that these site-specific recombination systems, although of microbial origin for the majority, function in higher eukaryotes, such as plants, insects and mice. Among the site-specific recombination systems commonly used, there may be mentioned the Cre/Lox and FLP/FRT systems. The strategy normally used consists of inserting the loxP (or FRT) sites into the chromosomes of ES cells by homologous recombination, or by conventional transgenesis, and then of delivering Cre (or FLP) for the latter to catalyze the recombination reaction. The recombination between the two loxP (or FRT) sites may be obtained in ES cells or in fertilized eggs by transient expression of Cre or using a Cre transgenic mouse. Such a strategy of somatic mutagenesis allows a spatial control of the recombination because the expression of the recombinase is controlled by a promoter specific for a given tissue or for a given cell.

A detailed description of the FRT system can be found, e.g., in U.S. Pat. No. 7,736,897.

The P1 bacteriophage uses Cre-lox recombination to circularize and facilitate replication of its genomic DNA when reproducing. Since being discovered, the bacteriophage's recombination strategy has been developed as a technology for genome manipulation. Because the cre gene and loxP sites are not native to the mouse genome, they are introduced by transgenic technology into the mouse genomes (Nagy A. 2000. Cre recombinase: the universal reagent for genome tailoring. Genesis 26:99-109). The orientation and location of the loxP sites determine whether Cre recombination induces a deletion, inversion, or chromosomal translocation (Nagy A. 2000. Cre recombinase: the universal reagent for genome tailoring. Genesis 26:99-109). The cre/lox system has been successfully applied in mammalian cell cultures, yeasts, plants, mice, and other organisms (Araki K, Imaizumi T, Okuyama K, Oike Y, Yamamura K. 1997. Efficiency of recombination by Cre transient expression in embryonic stem cells: comparison of various promoters. J Biochem (Tokyo) 122:977-82). Much of the success of Cre-lox is due to its simplicity. It requires only two components: (a) Cre recombinase: an enzyme that catalyzes recombination between two loxP sites; and (b) LoxP sites: a specific 34-base pair bp) sequences consisting of an 8-bp core sequence, where recombination takes place, and two flanking 13-bp inverted repeats.

Another method for delivery is cell-mediated delivery. In one embodiment, the optical sensors of the present invention are delivered using e.g., a cell expressing the optical sensor. A variety of means for administering cells to subjects are known to those of skill in the art. Such methods can include systemic injection, for example i.v. injection or implantation of cells into a target site in a subject. Cells may be inserted into a delivery device which facilitates introduction by injection or implantation into the subjects. Such delivery devices may include tubes, e.g., catheters, for injecting cells and fluids into the body of a recipient subject. In certain embodiments, the tubes additionally have a needle, e.g., a syringe, through which the cells of the invention can be introduced into the subject at a desired location. The cells may be prepared for delivery in a variety of different forms. For example, the cells may be suspended in a solution or gel or embedded in a support matrix when contained in such a delivery device. Cells may be mixed with a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is generally sterile and fluid. Generally, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention may be prepared by incorporating cells as described herein in a pharmaceutically acceptable carrier or diluent and, as required, other ingredients enumerated above, followed by filtered sterilization. The mode of cell administration can be relatively non-invasive, for example by intravenous injection, pulmonary delivery through inhalation, oral delivery, buccal, rectal, vaginal, topical, or intranasal administration.

However, the route of cell administration will depend on the tissue to be treated and may include implantation or direct injection. Methods for cell delivery are known to those of skill in the art and can be extrapolated by one skilled in the art of medicine for use with the methods and compositions described herein. Direct injection techniques for cell administration can also be used to stimulate transmigration through the entire vasculature, or to the vasculature of a particular organ, such as for example liver, or kidney or any other organ. This includes non-specific targeting of the vasculature. One can target any organ by selecting a specific injection site, such as e.g., a liver portal vein. Alternatively, the injection can be performed systemically into any vein in the body. This method is useful for enhancing stem cell numbers in aging patients. In addition, the cells can function to populate vacant stem cell niches or create new stem cells to replenish the organ, thus improving organ function. For example, cells may take up pericyte locations within the vasculature. Delivery of cells may also be used to target sites of active angiogenesis. If so desired, a mammal or subject can be pre-treated with an agent, for example an agent is administered to enhance cell targeting to a tissue (e.g., a homing factor) and can be placed at that site to encourage cells to target the desired tissue. For example, direct injection of homing factors into a tissue can be performed prior to systemic delivery of ligand-targeted cells.

Method of using stem cells, such as neural stem cells to deliver agents through systemic administration and via intracranial administration to home in on a tumor or to an injured parts of brain have been described (see, e.g., U.S. Pat. Nos. 7,655,224; and 7,393,526). Accordingly, one can also modify such cells to express the desired voltage sensor for delivery into the organs, such as the brain.

Membrane fusion reactions are common in eukaryotic cells. Membranes are fused intracellularly in processes including endocytosis, organelle formation, inter-organelle traffic, and constitutive and regulated exocytosis. Intercellularly, membrane fusion occurs during sperm-egg fusion and myoblast fusion. Further discussion of membrane usion mediated delivery of an optical sensor is provided in US Publication No. 2013/0224756, incorporated by reference.

Examples of other expression vectors and host cells are the pET vectors (Novagen), pGEX vectors (Amersham Pharmacia), and pMAL vectors (New England labs. Inc.) for protein expression in *E. coli* host cells such as BL21, BL21(DE3) and AD494(DE3)pLysS, Rosetta (DE3), and Origami(DE3) (Novagen); the strong CMV promoter-based pcDNA3.1 (Invitrogen) and pCIneo vectors (Promega) for expression in mammalian cell lines such as CHO, COS, HEK-293, Jurkat, and MCF-7; replication incompetent adenoviral vector vectors pAdeno X, pAd5F35, pLP-Adeno-X-CMV (Clontech), pAd/CMVN5-DEST, pAd-DEST vector (Invitrogen) for adenovirus-mediated gene transfer and expression in mammalian cells; pLNCX2, pLXSN, and pLAPSN retrovirus vectors for use with the Retro-X™ system from Clontech for retroviral-mediated gene transfer and expression in mammalian cells; pLenti4N/V5-DEST™, pLenti6/V5-DEST™, and pLenti6.2/V5-GW/lacZ (Invitrogen) for lentivirus-mediated gene transfer and expression in mammalian cells; adenovirus-associated virus expression vectors such as pAAV-MCS, pAAV-IRES-hrGFP, and pAAV-RC vector (Stratagene) for adeno-associated virus-mediated gene transfer and expression in mammalian cells; BACpak6 baculovirus (Clontech) and pFastBac™ HT (Invitrogen) for the expression in *Spodopera frugiperda* 9 (Sf9) and Sfl1 insect cell lines; pMT/BiPN/V5-His (Invitrogen) for the expression in *Drosophila* Schneider S2 cells; *Pichia* expression vectors pPICZα, pPICZ, pFLDα and pFLD (Invitrogen) for expression in *Pichia pastoris* and vectors pMETα and pMET for expression in *P. methanolica*; pYES2/GS and pYDI (Invitrogen) vectors for expression in yeast *Saccharomyces cerevisiae*. Recent advances in the large scale expression heterologous proteins in *Chlamydomonas reinhardtii* are described by Griesbeck C. et. al. 2006 Mol. Biotechnol. 34:213-33 and Fuhrmann M. 2004, Methods Mol Med. 94:191-5. Foreign heterologous coding sequences are inserted into the genome of the nucleus, chloroplast and mitochondria by homologous recombination. The chloroplast expression vector p64 carrying the versatile chloroplast selectable marker aminoglycoside adenyl transferase (aadA), which confers resistance to spectinomycin or streptomycin, can be used to express foreign protein in the chloroplast. The biolistic gene gun method can be used to introduce the vector in the algae. Upon its entry into chloroplasts, the foreign DNA is released from the gene gun particles and integrates into the chloroplast genome through homologous recombination.

Cell-free expression systems are also contemplated. Cell-free expression systems offer several advantages over traditional cell-based expression methods, including the easy modification of reaction conditions to favor protein folding, decreased sensitivity to product toxicity and suitability for high-throughput strategies such as rapid expression screening or large amount protein production because of reduced reaction volumes and process time. The cell-free expression system can use plasmid or linear DNA. Moreover, improvements in translation efficiency have resulted in yields that exceed a milligram of protein per milliliter of reaction mix. An example of a cell-free translation system capable of producing proteins in high yield is described by Spirin A S. et. al., Science 242:1162 (1988). The method uses a continuous flow design of the feeding buffer which contains amino acids, adenosine triphosphate (ATP), and guanosine triphosphate (GTP) throughout the reaction mixture and a continuous removal of the translated polypeptide product. The system uses E. coli lysate to provide the cell-free continuous feeding buffer. This continuous flow system is compatible with both prokaryotic and eukaryotic expression vectors. As an example, large scale cell-free production of the integral membrane protein EmrE multidrug transporter is described by Chang G. el. al., Science 310:1950-3 (2005). Other commercially available cell-free expression systems include the Expressway™ Cell-Free Expression Systems (Invitrogen) which utilize an E. coli-based in-vitro system for efficient, coupled transcription and translation reactions to produce up to milligram quantities of active recombinant protein in a tube reaction format; the Rapid Translation System (RTS) (Roche Applied Science) which also uses an E. coli-based in-vitro system; and the TNT Coupled Reticulocyte Lysate Systems (Promega) which uses a rabbit reticulocyte-based in-vitro system.

It is understood that the foregoing detailed description and the following examples are illustrative only and are not to be taken as limitations upon the scope of the invention. Various changes and modifications to the disclosed embodiments, which will be apparent to those skilled in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

In order that the invention described herein may be more fully understood, the following examples are set forth. It should be understood that these examples are for illustrative purposes only and are not to be construed as limiting this invention in any manner.

Experimental Methods

Engineering of Arch. We adopted a hierarchical approach to screening that prioritized brightness over multiple secondary selection criteria. The brightness screen was conducted by examining the fluorescence of large libraries of variants expressed in bacterial colonies. Subsequent screens for trafficking, speed, and voltage sensitivity were performed in HeLa cells subjected to field stimulation and induced transmembrane voltages, and then in HEK cells with patch clamp.

Molecular biology procedures: Synthetic DNA oligonucleotides used for cloning and library construction were purchased from Integrated DNA Technologies. Pfu polymerase (Fermentas) or AccuPrime Pfx SuperMix (Invitrogen) were used for high fidelity non-mutagenic PCR amplifications in the buffer supplied by the respective manufacturer. Taq polymerase (New England Biolabs) in the presence of $MnCl_2$ (0.1 mM) was used for error-prone PCR. PCR products and products of restriction digests were routinely purified using preparative agarose gel electrophoresis followed by DNA isolation using the GeneJET gel extraction kit (Fermentas). Restriction endonucleases were purchased from Fermentas and used according to the manufacturer's recommended protocol. Ligations were performed using T4 ligase (Invitrogen) or Gibson Assembly (New England Biolabs). Small-scale isolation of plasmid DNA was performed by GeneJET miniprep kit (Fermentas). The cDNA sequences for all Arch variants and fusion constructs were confirmed by dye terminator cycle sequencing using the BigDye Terminator Cycle Sequencing kit (Applied Biosystems). Site-directed mutagenesis and randomization of targeted codons was performed with either the QuikChange Lightning Single or Multi kit (Agilent Technologies).

Construction of Arch mutant libraries: A library of >$10^4$ mutants was generated by error-prone PCR of the gene encoding Arch D95N. These variants were then joined with the gene encoding mOrange2 by a two-part overlap extension PCR. The 5' piece used in the overlap extension was prepared by error-prone PCR of Arch D95N as template with a mixture of the forward primer (Fw_XbaI_Arch) and reverse primer (RV_Arch). Primer Fw_XbaI_Arch contains an XbaI site and primer RV_Arch contains an overlap region with primer FW_Arch_FP. The 3' piece for use in the overlap extension was prepared by high fidelity PCR amplification of mOrange2 using a forward primer (FW_Arch_FP) and a reverse primer (RV_HindIII_FP). Primer RV_HindIII_FP contains a stop codon and a HindIII site. The full-length Arch-mOrange2 gene library was assembled by overlap extension PCR using an equimolar mixture of primers Fw_XbaI_Arch and RV_HindIII_FP together with a mixture of the 5' and 3' PCR fragments described above (50 ng each) as the template. In later rounds of directed evolution, error-prone PCR and StEP PCR DNA shuffling[60] were both used for construction of Arch-mOrange2 gene libraries.

The full-length PCR product (approximately 1,500 b.p.) was purified by agarose gel electrophoresis, doubly digested, and ligated between the XbaI and HindIII sites of a modified pBAD vector which was generated by deleting the ETorA tag between the NcoI and XbaI sites of the pTorPE vector[61] using Quikchange Lightning kit.

Following ligation, electrocompetent E. coli strain DH10B was transformed with the library of gene variants and cultured overnight at 37° C. on 10-cm Petri dishes of LB-agar supplemented with 100 μL of 4 mM retinal (Sigma-Aldrich), 100 g/mL ampicillin (Sigma), and up to 0.0020% (wt/vol) L-arabinose (Alfa Aesar). The retinal solution was added on the surface of LB-agar plates evenly and air-dried prior to plating the cell suspension. At concentrations of L-arabinose higher than 0.0020% (wt/vol) we observed abnormal colony morphologies and reduced fluorescent brightness, presumably due to cytotoxicity caused by overexpression.

Screening of Arch mutants in *E. coli*: The imaging system used for library screening has previously been described in detail.[62] We screened 10,000-20,000 colonies (10-20 plates of bacterial colonies) per round of random mutagenesis. For libraries generated by randomization of one or more codons, we screened approximately 3-fold more colonies than the expected library diversity (e.g. 3,000 colonies for a 1,000-member library).

We acquired two images of colonies using filter sets for mOrange2 (exc. 540-580 nm, em. 600-660 nm) and Arch (exc. 604-640 nm and em. 660-700 nm). An image of the ratio of Arch:mOrange2 fluorescence was calculated, and the colonies with the top 0.01% to 0.1% highest ratios were manually picked. Picked clones were individually cultured in 2 mL liquid LB medium (200 μg/mL ampicillin) shaken (250 rpm) overnight at 37° C.

Protein expression was induced by adding 2 mL, of liquid LB medium containing 120 μM retinal, 200 μg/mL ampicillin and 0.2% L-arabinose to the overnight culture, followed by incubation at 37° C. for 3 hours. The cell pellets were collected by centrifugation, washed and resuspended in buffered M9 salt solution containing 7 g/L $Na_2HPO_4$, 3 g/L $KH_2PO_4$, 0.5 g/L NaCl and 1 g/L $NH_4Cl$. The suspension was then diluted 5-fold prior to acquisition of its fluorescence spectrum in a Safire 2 fluorescence microplate reader (Tecan).

The emission profiles of each variant under excitation at 525 nm and 600 nm were acquired and normalized by the absorbance at 600 nm. The cell pellets of the three variants with the highest ratios of Arch to mOrange2 and the two variants with the brightest absolute Arch fluorescence were treated for plasmid DNA extraction, and the pooled genes were used as templates for construction of gene libraries in the next round of directed evolution.

After five iterations we arrived at a non-pumping variant of Arch with five mutations relative to wild-type (P60S, T80S, D95N, D106Y, and F161 V) and significantly improved brightness under excitation with low illumination intensity. This variant, designated Arch 3.5, was used as the template for subsequent efforts to address the secondary selection criteria.

Random mutagenesis at positions Asp95 and Asp106: We next focused on tuning other properties of Arch including voltage sensitivity, response kinetics, membrane trafficking and the undesirable dependence of brightness on illumination intensity. Positions Asp95 and Asp106 of Arch are structurally aligned with positions Asp85 and Asp96 of bacteriorhodopsin, and have been reported to play key roles in proton translocation during the photocycle.[63, 64] The voltage sensing mechanism of Arch is likely due to electric-field-dependent protonation of the retinal Schiff base,[10,65] so we reasoned that perturbations of the proton translocation network around the Schiff base could potentially affect the voltage sensitivity, response kinetics, or complex photophysics.[24]

We constructed libraries in which Asp95 and Asp106 were randomized to a subset of all possible amino acid substitutions. First, we randomized position 95 using codon HVS (where H=A, C or T; V=A, C, or G; S=C or G), which encodes for all amino acids except Ala, Gly, Asp, Glu and Val. This library was screened by fluorescence imaging of *E. coli* colonies. Variants that retained a high ratio of Arch to mOrange2 fluorescence were picked and expressed in HeLa cells for screening via induced transmembrane voltage (see below).

The mutation N951H emerged as the best from the first round of screening in HeLa cells. We then constructed a second library by randomizing position 106 to a subset of amino acids with polar or charged side chains (codon NRC, where N=A, C, G, or T; R=A or G), and screened these in HeLa cells. The variant with histidine at position 106 proved most promising and was designated QuasAr1.

Solubilization and spectroscopic characterization of QuasAr1 and QuasAr: *E. coli* expressing QuasAr1 and QuasAr2 were grown in 12 mL liquid LB medium with 200 μg/ml ampicillin overnight. The next day, 12 mL of liquid LB medium containing 50 μM retinal, 200 μg/ml ampicillin and 0.1% arabinose was added into the overnight culture, followed by additional incubation at 37° C. for 4 hours. The cell pellets were collected by centrifugation and lysed by suspension in B-PER solution (Pierce). The cytoplasmic fraction was discarded after centrifugation and the colored insoluble fraction was resuspended in phosphate buffered saline (PBS) containing 1.5% n-dodecyl-3-D-maltopyranoside (Affymetrix, Inc.). The suspension was homogenized by an ultrasonic homogenizer and centrifuged (17,000 g for 15 mins, 4° C.). The solubilized protein in the supernatant was used for in vitro spectroscopic characterization.

Absorption spectra were recorded on a DU-800 UV-visible spectrophotometer (Beckman) and fluorescence spectra were recorded on a Safire2 plate reader (Tecan). Cy5 carboxylic acid (Cyandye) was used as the reference for quantum yield measurement. Quantum yield measurements were performed on a series of dilutions of each protein solution and standard, with absorbance values ranging from 0.01 to 0.05 at 600 nm. The fluorescence emission spectra of each dilution were recorded with excitation at 600 nm and the total fluorescence intensities obtained by integration. Integrated fluorescence intensity vs. absorbance was plotted for each protein and each standard. Quantum yields, Φ, were determined from the slopes (S) of each line using the equation: $\Phi_{protein} = \Phi_{standard} \times (S_{protein}/S_{standard})$.

Expression vectors for HeLa cells: To express Arch-mOrange2 variants in HeLa cells, the gene in the pBAD vector was first amplified by PCR using primers Fw_BamHI_Kozak_Arch and RV_FP_ERex_stp_XbaI. This reverse primer encodes the endoplasmic reticulum (ER) export sequence from the inward-rectifier potassium channel Kir2.1 (FCYENE) (SEQ ID NO: 8),[66] which has been reported to be effective for improving the membrane trafficking of Arch in mammalian cells.[25]

The purified DNA was digested with BamHI and XbaI restriction enzymes and ligated into a purified pcDNA3.1 plasmid that had been digested with the same two enzymes. The ligation reaction was used for transformation of electrocompetent *E. coli* strain DH10B cells. Cells were plated on LB/agar supplemented with ampicillin and individual colonies were picked into 4 mL of LB/ampicillin following overnight incubation at 37° C. Liquid cultures were shaken at 250 rpm and 37° C. for 12-15 h and then a small scale isolation of plasmid DNA was performed. Each gene in pcDNA3.1 was fully sequenced using T7_FW, and BGH_RV primers. Plasmids were then used for cell transfection as described below Induced transmembrane voltage (ITV) in HeLa cells: We co-expressed prospective Arch variants in HeLa cells with the inward rectifier potassium channel, Kir2.1. Expression of Kir2.1 lowered the resting potential to approximately −60 mV, close to the resting potential of neurons.[67,68] We reasoned that this effect would center the ITV close to the physiologically relevant range.

HeLa cells were grown to 40-60% confluence on home-made 35 mm glass bottom dishes or 24-well glass bottom plates. Cells were transfected with 1 μg of plasmid DNA comprising a 1:1 mixture of Arch variant and Kir2.1, using either 2 μL Turbofect (Thermo Scientific) or 2 μL Lipofectamine 2000 (Invitrogen) according to the manufacturer's instructions. After 3 h incubation, the medium was exchanged to DMEM with 10% fetal bovine serum. Cells were incubated for an additional 24 h at 37° C. in a $CO_2$ incubator. Immediately prior to imaging, cells were washed twice with Hanks balanced salt solution (HBSS) and then 1 mL of 20 mM HEPES buffered HBSS was added.

Cell imaging was performed with an inverted Eclipse Ti-E (Nikon) equipped with a Photometrics QuantEM 512SC camera, a 150 W mercury-xenon lamp (Hamamatsu), and a 10 mW 638 nm semiconductor diode laser (56ICS/S2669, Melles Griot CleanBeam) aligned just above the angle for total internal reflection. The filters were: 590-650 nm (excitation), 668-738 nm (emission), and 666 nm (dichroic). Movies were acquired at 10 ms/frame. The NIS-Elements Advanced Research software (Nikon) was used for microscope and camera control and data acquisition. A schematic of the setup is shown in FIG. 2.

To probe the response kinetics and voltage sensitivity, we used a pair of parallel platinum electrodes to apply a reproducible electric field across the cell culture and induce transient asymmetries in the membrane voltage.[69] Platinum electrodes with a gap of 0.5 cm were mounted in a custom plastic support. The electrode pair was placed in the imaging dish or well, and voltage pulses from a 6824A 40V/25A DC Power Supply (HP/Agilent) were applied using waveforms generated by a pulse generator PG 58A (Gould Advance Ltd). The typical waveform had square-wave pulses lasting 20 ms, and pulse amplitudes from 25-35 V. Fluorescence was imaged at 100 Hz frame rate in 4×4 binning mode for 10 seconds. During each voltage pulse, opposite sides of the cell showed opposite fluorescence transients. Typical fluorescence traces are shown in FIG. 2.

Raw fluorescence traces were corrected for background autofluorescence and photobleaching. The average voltage sensitivity ($\Delta F/F_{min}$) and signal-to-noise ratio of each Arch variant were compared to the best variant of the previous generation, and only the variants with equal or improved performance were chosen as templates for the next round of screening.

Expression vectors for HEK cells and neurons: To enable more accurate electrophysiological characterization via patch clamp in HEK cells and primary neuron cultures, we cloned QuasAr1 into the BamHI/EcoRI sites of lentivirus vector FCK-Arch-GFP (Addgene: 22217). This vector contains a CaMKIIα promoter and a Woodchuck Hepatitis Virus Posttranscriptional Regulatory Element (WPRE) after the 3' end of the open reading frame. The Arch cDNA was generated by PCR using forward primer FW_BamHI_Kozak_Arch_ValSer and overlapping reverse primers RV_FP_TS and RV_TS_ERex_stp_EcoRI. These reverse primers introduce a trafficking signal (TS) motif and ER export signal peptide sequence at the C-terminus of the protein.

Simultaneous electrophysiology and fluorescence in HEK cells: HEK293T cells (ATCC CRL-11268) were cultured and transfected following standard protocols.[10] Briefly, HEK-293 cells were grown at 37° C., 5% $CO_2$, in DMEM supplemented with 10% FBS and penicillin-streptomycin. Plasmids were transfected using Transit 293T (Mirus) following the manufacturer's instructions, and assayed 48 hours later. The day before recording, cells were re-plated onto glass-bottom dishes (MatTek) at a density of ~10,000 cells/cm². Cells were supplemented with retinal by diluting stock retinal solutions (40 mM, DMSO) in growth medium to a final concentration of 5 μM, and then returning the cells to the incubator for 0.5-1 hour. All imaging and electrophysiology were performed in Tyrode buffer (containing, in mM: 125 NaCl, 2.5 KCl, 3 $CaCl_2$, 1 $MgCl_2$, 10 HEPES, 30 glucose pH 7.3, and adjusted to 305-310 mOsm with sucrose). A gap junction blocker, 2-aminoethoxydiphenyl borate (50 μM, Sigma), was added to eliminate electrical coupling between cells.

Filamented glass micropipettes (WPI) were pulled to a tip resistance of 5-10 MΩ, and filled with internal solution containing 125 mM potassium gluconate, 8 mM NaCl, 0.6 mM MgCl2, 0.1 mM CaCl2, 1 mM EGTA, 10 mM HEPES, 4 mM Mg-ATP, 0.4 mM Na-GTP (pH 7.3); adjusted to 295 mOsm with sucrose. Pipettes were positioned with a Sutter MP285 manipulator. Whole-cell, voltage and current clamp recordings were acquired using an Axopatch 700B amplifier (Molecular Devices), filtered at 2 kHz with the internal Bessel filter and digitized with a National Instruments PCIE-6323 acquisition board at 5-10 kHz. Data was only acquired from HEK cells having reversal potentials between −10 and −40 mV, access resistance <25 MΩ and membrane resistance >0.5 GΩ.

Simultaneous whole-cell patch clamp recordings and fluorescence recordings were acquired on a home-built, inverted epifluorescence microscope, described previously[10] and described below in "Apparatus". For step response measurements, voltage clamp electronics were compensated 90-95%. We examined variants of QuasAr1 with mutations at position 95 (Asn, Cys, Gln, His and Tyr) and position 106 (Arg, Asp, Asn, Cys, Glu, His, Lys and Tyr). These experiments confirmed that histidine at position 106 provided undetectable photocurrent, and the best combination of improved voltage sensitivity, and fast kinetics. Mutants with Gln, Cys, or Asn at position 95 exhibited better voltage sensitivity compared to QuasAr1, while retaining fast kinetics. We designated the H95Q mutant QuasAr2.

Analysis of mutations in QuasAr1 and QuasAr2: We developed a structural model of QuasAr1 (FIG. 3) based on homologous protein Arch-2 (PDB: 2EI4)[70]. Mutations T80S and F161V are located in the periphery of the protein, while P60S is close to the Schiff base of the retinal chromophore. Given their location, we suspect that the T80S and F161V substitutions are unlikely to have a direct impact on the photophysical properties of the protein, and are more likely to have a role in improving the folding efficiency. In contrast, the close proximity of the P60S substitution to the Schiff base suggests that this mutation has a more direct influence on the photophysical properties.

Figure 4A:
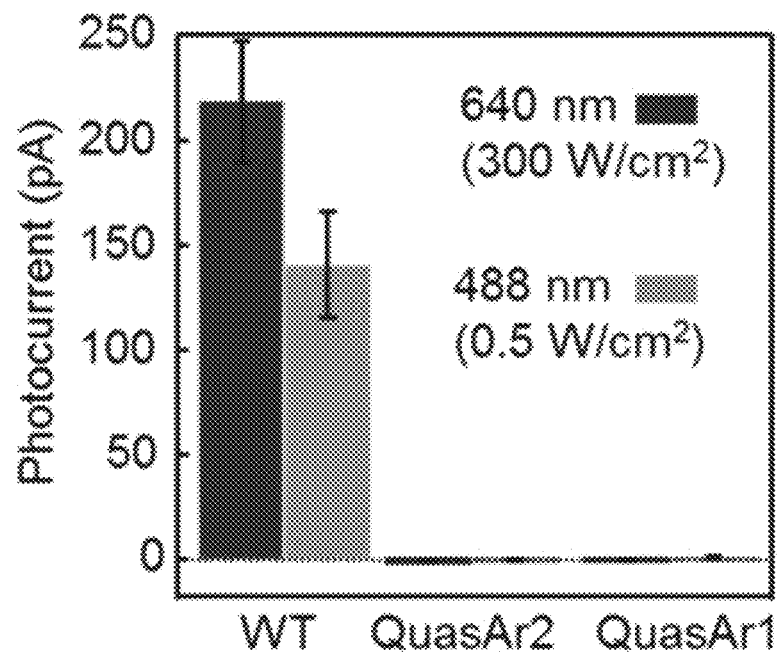
FIGS. 4A-4B show the photophysics of QuasArs in mammalian cells.
Figure 4B:
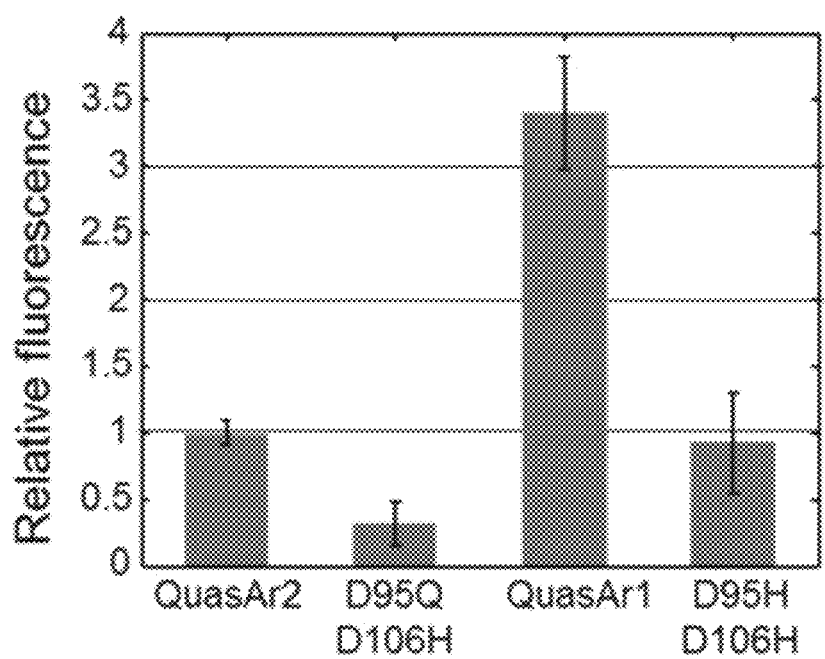
Figure 5A:
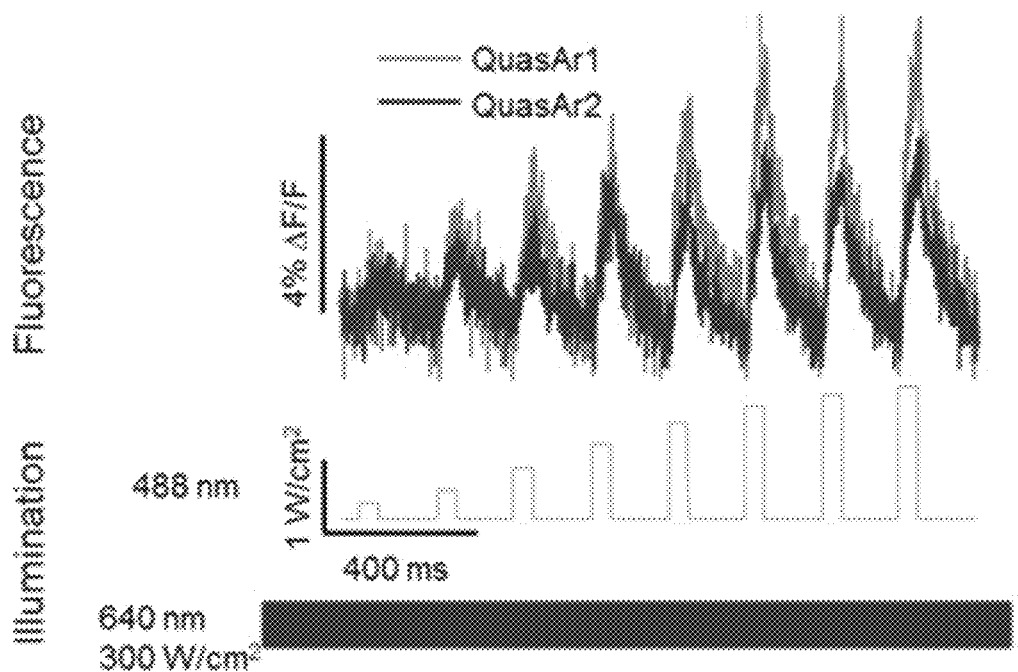
FIGS. 5A-5B show the quantification of optical crosstalk of blue illumination into QuasAr fluorescence. Illumination sufficient to induce high-frequency trains of action potentials (488 nm, 140 mW/cm2) perturbed fluorescence of QuasArs by <1%.
Figure 5B:
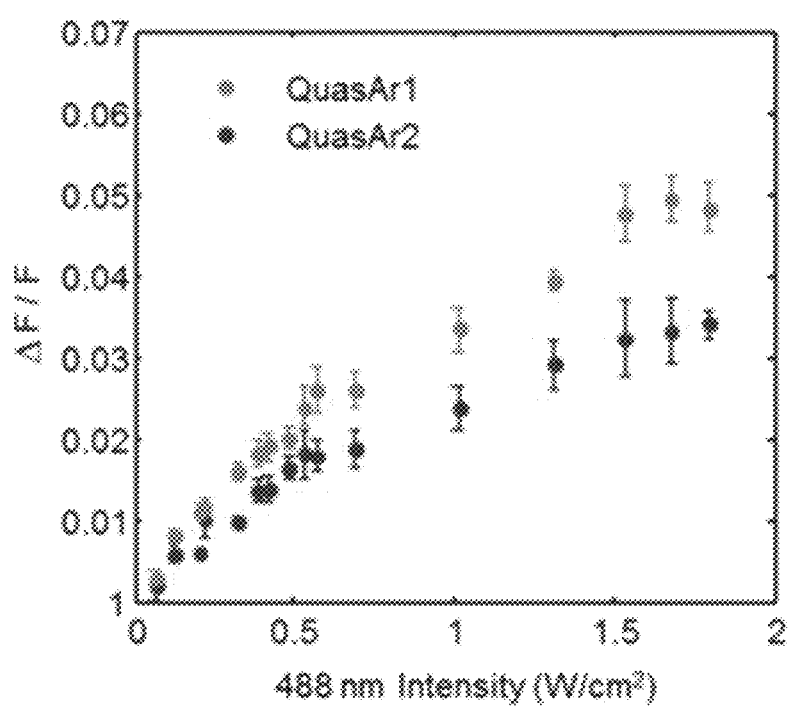

We compared the Arch double mutants Arch (D95H, D106H) (termed "HH") and Arch(D95Q, D106H) (termed "QH") to the corresponding QuasAr1 and QuasAr2 mutants do determine whether the mutations in the proton-transport chain were sufficient to induce the improved sensor performance. QuasAr1 and QuasAr2 were both significantly brighter than the corresponding double mutants (FIG. 4). Furthermore, the voltage sensitivity of the HH, QH, QuasAr1 and wild-type protein were comparable, and three-fold less than the sensitivity of QuasAr2. Speeds were similar between the QuasAr variants and the double mutants. Thus one or more of the three mutations outside the proton transport chain (P60S, T80S, F161 V) plays an important role in the brightness and sensitivity of the QuasAr mutants. The constructs described in herein are available on Addgene.

Oligonucleotides used in directed evolution of QuasAr mutants. The sequences, from top to bottom, correspond to SEQ ID NOs: 12-27.

| Name | Sequence |
|---|---|
| Fw_XbaI_Arch | CGACTCTAGAATGGACCCCATCGCTCTGCAGGCTGGTTACGA<br>CCTGCTGGGTGACGGC |
| RV_Arch | TGCTACTACCGGTCGGGGCTCGGGGGCCTC |
| FW_Arch_FP | GAGGCCCCCGAGCCCCGACCGGTAGTAGCAATGGTGAGCAA<br>GGGCGAGGAG |
| RV_HindIII_FP | GATGAAGCTTTTACTT GTACAGCTCGTCCATGCCG |
| FW_Arch_95X | CTATTATGCCAGGTACGCCHVSTGGCTGTTTACCACCCCAC |
| FW_Arch_106X | CCCCACTTCTGCTGCTGNRCCTGGCCCTTCTCGCTAA |
| FW_Arch_95N | ATTATGCCAGGTACGCCAATTGGCTGTTTACCACC |
| FW_Arch_95C | CTA TTA TGC CAG GTA CGC CTGTTG GCT GTT TAC CAC CCC AC |
| FW_Arch_95Q | CTA TTA TGC CAG GTA CGC CCAGTG GCT GTT TAC CAC CCC AC |
| FW_Arch_106C | CCCCACTTCTGCTGCTGTGCCTGGCCCTTCTCGCTAA |
| Fw_Arch_106E | CCCCACTTCTGCTGCTGGAGCTGGCCCTTCTCGCTAA |
| Fw_BamHI_Kozak_Arch | CGACGGATCCACCATGGACCCCATCGCTCTGCAGGC |
| RV_FP_ERex_stp_XbaI | GATGTCTAGATTATTCATTCTCATAACAAAACTTGTACAGCTCG<br>TCCATGCCG |
| FW_BamHI_Kozak_Arch_ValSer | TGGGATCCACCATGGTAAGTATCGCTCTGCAGGCTGGTTAC |
| RV_FP_TS | ATCCAGGGGATGTACTCGCCTTCGCTTGTGATTCTACTCTTG<br>TACAGCTCGTCCATGCCG |
| RV_TS_ER export_stop_EcoRI | GATGGAATTCTTATACTTCATTCTCATAACAAAATCC<br>ACCTACATTTATGTCTATTTGATCCAGGGGATGTACTCGCC |

Other Applications.

In some applications one might wish to use the visible spectrum for other imaging modalities, e.g. for a reporter of $Ca^{2+}$ or a GFP expression marker. In such cases, it is inconvenient to have mOrange2 fused to Arch. Removal of the eGFP tag from Arch resulted in poor membrane localization in neurons. To maintain the beneficial trafficking properties of the eGFP tag while eliminating the eGFP fluorescence, we mutated the eGFP chromophore from TYG to GGG using site-directed mutagenesis (Agilent). This mutation has been reported to preserve folding of eGFP.[72] We also made versions of the fusion protein in which the mOrange2 was mutated to a non-fluorescent form by the mutation TYG to TAG. Nucleic acid constructs for the fusion protein were incorporated into lentiviral vectors under the CaMKIIα promoter, adapted from Addgene plasmid 22217.

Neuronal Culture and Gene Delivery.

All procedures involving animals were in accordance with the National Institutes of Health Guide for the care and use of laboratory animals and were approved by the Institutional Animal Care and Use Committee at the institution at which they were carried out.

Primary neurons: Rat glial monolayers were prepared similarly to previous literature.[73] Briefly, $10^6$ dissociated hippocampal cells from P0 rat pups (Sprague Dawley, Tocris)[74] were plated on a 10 cm culture dish in glial medium GM, comprised of 15% FBS (Life), 0.4% (w/v) D-glucose, 1% glutamax (Life), 1% penicillin/streptomycin (Life) in MEM (Life). When the dish reached confluence (1-2 weeks), cells were split using trypsin onto Mattek dishes (Mattek P35G-1.5-14-C) coated with matrigel (BD biosciences) at a density of (3500 cells/$cm^2$). After ~3-6 days, glial monolayers were at or near confluence and the medium was replaced by GM with 2 μM cytarabine (cytosine-β-arabinofuranoside). Dishes were maintained in GM with 2 μM cytarabine until use. Dishes were discarded if microglia or neurons were identified on the monolayers.

Hippocampal neurons from P0 rat pups were dissected and cultured in neurobasal-based medium (NBActiv4, Brainbits llc.) at a density of 30,000-40,000 $cm^{-2}$ on the pre-established glial monolayers.[74] At one day in vitro (DIV), cytarabine was added to the neuronal culture medium at a final concentration of 2 μM to inhibit further glial growth.[75]

Neurons were transfected on DIV7 with the QuasArs plasmids via the calcium phosphate transfection method.[76] Measurements on neurons were taken between DIV 13-18.

For TTX-induced homeostatic plasticity, primary neurons were transfected via the calcium phosphate method on DIV7. TTX (1 μM) was added on DIV 16. Excitability was measured on DIV 18 in Tyrodes medium with synaptic blockers (10 μM NBQX, 25 μM AP-V, 20 μM Gabazine).

hiPSC-derived neurons: Human iPSC-derived iCell neurons from Cellular Dynamics Inc. were thawed and resuspended in complete iCell Neuron Maintenance Medium (CM) following manufacturer protocols. Neurons were then plated at a density 125,000/$cm^2$ on pre-established rat glial monolayers grown on glass-bottomed dishes. Medium was replaced 24 hours post plating with CM supplemented with 10 ng/mL BDNF (Peprotech). Thereafter, 50% media exchanges with CM were done every 5 days.

For TTX-induced homeostatic plasticity, hiPSC-derived neurons were transfected via the calcium phosphate method on DIV17. TTX (1 μM) was added on DIV 26. Excitability was measured on DIV 28 in Tyrodes medium with synaptic blockers (10 μM NBQX, 25 μM AP-V, 20 μM Gabazine).

For KCl-induced homeostatic plasticity, hiPSC-derived neurons were transfected on DIV 10. KCl (15 mM) was added from DIV 18 to DIV 21 (60 h). Excitability was measured on DIV 21 in Tyrodes medium with synaptic blockers (10 μM NBQX, 25 μM AP-V, 20 μM Gabazine).

Organotypic brain slice culture: Organotypic hippocampal slices cultures were prepared from postnatal day 6-8 Sprague-Dawley rats as described previously.[77] The brain was taken out and immediately placed in chilled dissection media. Transverse hippocampal slices were cut with 400 μm thickness and 4 to 6 slices were placed in a sterile culture plate insert (Millicell-CM, Millipore) in 6-well plates containing prewarmed media. Slices were biolistically transfected with a Helios Gene Gun (BioRad) at 2 days in vitro (DIV 2). Bullets were prepared using 12.5 μg of 1.6 μm gold particles and 80-100 μg of plasmid DNA. Slices were maintained until imaging at DIV 12-16.

Immediately prior to inverted imaging, slices were affixed to a nylon mesh weight and mounted upside down in a delta T brainslice adapter for inverted microscope imaging (Bioptechs). Artificial cerebrospinal fluid (ACSF) was bubbled with carbogen (95% $O_2$, 5% $CO_2$) and flowed over the slice at 1 mL/min at 23° C.

Electrophysiology in Neurons.

Measurements were performed on primary cultures at 13-15 DIV. Experiments were conducted in Tyrode's solution containing 125 mM NaCl, 2.5 mM KCl, 3 mM $CaCl_2$, 1 mM $MgCl_2$, 10 mM HEPES, 30 mM glucose (pH 7.3) and adjusted to 305-310 mOsm with sucrose. Prior to imaging, neurons were incubated with 5 μM all-trans retinal for 30 minutes and then washed with Tyrode's solution.

Synaptic blockers were added to the imaging medium for measurements of single-cell electrophysiology (Arch photocurrents, and single-cell excitability). The blockers comprised NBQX (10 μM, Tocris), D(−)-2-amino-5-phosphonovaleric acid (AP5; 25 μM, Tocris), and gabazine (SR-95531, 20 μM, Tocris). For measurements of channelrhodopsin photocurrents in neurons, TTX (1 μM, Tocris) was included along with the synaptic blockers to prevent recruitment of voltage gated sodium channels. Patch clamp data was used if and only if access resistance was <25 MΩ, and did not vary over the experiment. Recordings were terminated if membrane resistance changed by >10%. Experiments were performed at 23° C. under ambient atmosphere unless otherwise noted.

Comparison of QuasArs to Arclight A242: Arclight A242 was prepared in an identical lentiviral plasmid driven by a CaMKIIα promoter and was transfected (DIV 7) in parallel with the QuasAr plasmids in paired cultures. We used a standard Arclight imaging intensity of 10 W/cm$^2$ at 488 nm. QuasAr expressing neurons were imaged at two intensities (300 and 800 W/cm$^2$ at 640 nm). All recordings were made on the setup described below ("Apparatus") at a 1 kHz frame rate and 60× magnification. Due to its slow kinetics at room temperature (FIG. 9), Arclight recordings were made at 34° C. to enhance SNR and to match previously published conditions.[23] QuasAr2 reported APs with comparable SNR at 23° C. and 34° C. (41±3, n=8 cells, 640 nm 300 W/cm$^2$). For comparisons in organotypic brain slice, Arclight was imaged at 50 W/cm$^2$ on an upright microscope to enable simultaneous patch clamp stimulation and recordings. Recordings were made at a 1 kHz frame rate as described below ("Apparatus") and were acquired at 34° C.

Immunostaining.

Cultures were fixed immediately following data acquisition in a solution of 4% paraformaldehyde and 4% sucrose (w/v) in PBS, pH 7.4 at room temperature for 8 minutes. Fixed cultures were then washed three times in Dulbecco's PBS supplemented with $Ca^{2+}$ and $Mg^{2+}$ (DPBS), pH 7.4, prior to permeabilization and blocking in a solution of 0.1% (w/v) gelatin and 0.3% Triton-X-100 (v/v) in PBS, pH 7.4 (GTB) for 12-48 hours at 4 C.

For experiments using the sub-frame interpolation algorithm, primary cultures were fixed and stained using primary mouse monoclonal anti-ankyrin G (NeuroMab clone N106/36; 1:500), primary rabbit monoclonal anti-GFP (Abcam ab32146, lot YK011702CS, 1:1000), secondary goat anti-rabbit AlexaFluor 488 conjugated (Abcam ab150077, 1:500), and secondary goat anti-mouse AlexaFluor 647 conjugated (Abcam ab150115, 1:500) antibodies.

For experiments on human iPSC derived neurons, cultures were incubated with primary mouse anti-human nuclear antigen antibody (Millipore MAB 1281 clone 235-1, 1:500) in GTB overnight at 4° C., then washed three times in DPBS, and incubated with rabbit anti-GFP AlexaFluor 488 conjugated (polyclonal, Life A21311, 1:300) and secondary antibody donkey anti-mouse AlexaFluor 647 (Life A31571, 1:300) in GTB overnight at 4 C. Cultures were washed three times in DPBS prior to mounting in DAPI Fluoromount-G (Southern Biotech).

Apparatus.

Experiments were conducted on a home-built inverted fluorescence microscope, similar to the one described in the methods.[10] Briefly, illumination from a red laser 640 nm, 140 mW (Coherent Obis 637-140 LX), was expanded and focused onto the back-focal plane of a 60× oil immersion objective, numerical aperture 1.45 (Olympus 1-U2B616). Imaging of brain slices was performed with a 20× water-immersion objective, numerical aperture 1.0 (Zeiss W Plan-Apo).

Illumination from a blue laser 488 nm 50 mW (Omicron PhoxX) was sent through an acousto-optic modulator (AOM; Gooch and Housego 48058-2.5-0.55-5 W) for rapid control over the blue intensity. The beam was then expanded and modulated by a digital micromirror device (DMD) with 608×684 pixels (Texas Instruments LightCrafter). The DMD was controlled via custom software (Matlab) through a TCP/IP protocol. The DMD chip was re-imaged through the objective onto the sample, with the blue and red beams merging via a dichroic mirror. Each pixel of the DMD corresponded to 0.65 m in the sample plane. A 532 nm laser was combined with the red and blue beams for imaging of mOrange2. We wrote software to map DMD coordinates to camera coordinates, enabling precise optical targeting of any point in the sample.

To achieve precise optical stimulation of user-defined regions of a neuron, it was necessary to determine the mapping from pixels on the DMD to pixels on the camera. A uniform fluorescent film (exc. 488 nm, em. 515 nm) was loaded into the microscope. The DMD projected an array of dots of known dimensions onto the sample. The camera acquired an image of the fluorescence. Custom software located the centers of the dots in the image, and created an affine transformation to map DMD coordinates onto camera pixel coordinates.

A dual-band dichroic (Chroma zt532/635rpc) separated fluorescence of mOrange2 and Arch from excitation light. A 531/40 nm bandpass filter (Semrock FF01-531/40-25) and 495 nm longpass dichroic (Semrock FF495-Di03) was used for eGFP imaging, a 710/100 nm bandpass filter (Chroma, HHQ710/100) was used for Arch imaging, and a quad-band emission filter (Chroma ZET405/488/532/642m) was used for mOrange2 imaging and pre-measurement calibrations. A variable-zoom camera lens (Sigma 18-200 mm f/3.5-6.3 II DC) was used to image the sample onto an EMCCD camera (Andor iXon+ DU-860), with 128×128 pixels. The variable zoom enabled imaging at a range of magnifications while maintaining the high light collection efficiency of the oil or water immersion objectives.

In a typical experimental run, images of mOrange2 and QuasAr fluorescence were first acquired at full resolution (128×128 pixels). Data was then acquired with 2×2 pixel binning to achieve a frame rate of 1,000 frames/s. For experiments with infrequent stimulation (once every 5 s), the red illumination was only on from 1 s before stimulation to 50 ms after stimulation to minimize photobleaching. Cumulative red light exposure was typically limited to <5 min. per neuron, although continuous red light exposure for 30 minutes was well tolerated.

Low magnification wide-field imaging was performed with a custom microscope system based around a 2×, NA 0.5 objective (Olympus MVX-2). Illumination was provided by six lasers 640 nm, 500 mW (Dragon Lasers 635M500), combined in three groups of two. Illumination was coupled into the sample using a custom fused silica prism, without passing through the objective. Fluorescence was collected by the objective, passed through an emission filter, and imaged onto a scientific CMOS camera (Hamamatsu Orca Flash 4.0). Blue illumination for channelrhodopsin stimulation was provided by a 473 nm, 1 W laser (Dragon Lasers), modulated in intensity by an AOM and spatially by a DMD (Digital Light Innovations DLi4130-ALP HS). The DMD was re-imaged onto the sample via the 2× objective.

During an experimental run, we first acquired an image of a neuron using wide-field illumination at 640 nm and Arch fluorescence and/or 532 nm and mO2 fluorescence. A user then selected one or more regions of interest on the image of the neuron, and specified a timecourse for the illumination in each region. The software mapped the user-selected pixels onto DMD coordinates and delivered the illumination instructions to the DMD.

Data Analysis.

Statistics: All error ranges represent standard error of the mean, unless otherwise specified. For two-sample comparisons of a single variable, data was tested for normality using the Shapiro-Wilks test. If the data was detectably non-Gaussian, we performed a nonparametric Mann-Whitney U test. Otherwise we performed a two-tailed student's t-test. Probabilities of the null hypothesis p<0.05 were judged to be statistically significant.

Extracting fluorescence from movies: Fluorescence values were extracted from raw movies in one of two ways. One approach used the maximum likelihood pixel weighting algorithm.[10] Briefly, the fluorescence at each pixel was correlated with the whole-field average fluorescence. Pixels that showed stronger correlation to the mean were preferentially weighted. This algorithm automatically found the pixels carrying the most information, and de-emphasized background pixels. This approach was used for all experiments in cultured neurons. In images containing multiple neurons, the segmentation was performed semi-automatically using the independent components-based approach.[78]

Alternatively, a user defined a region comprising the cell body and adjacent processes, and calculated fluorescence from the unweighted mean of pixel values within this region.

Figure 10:
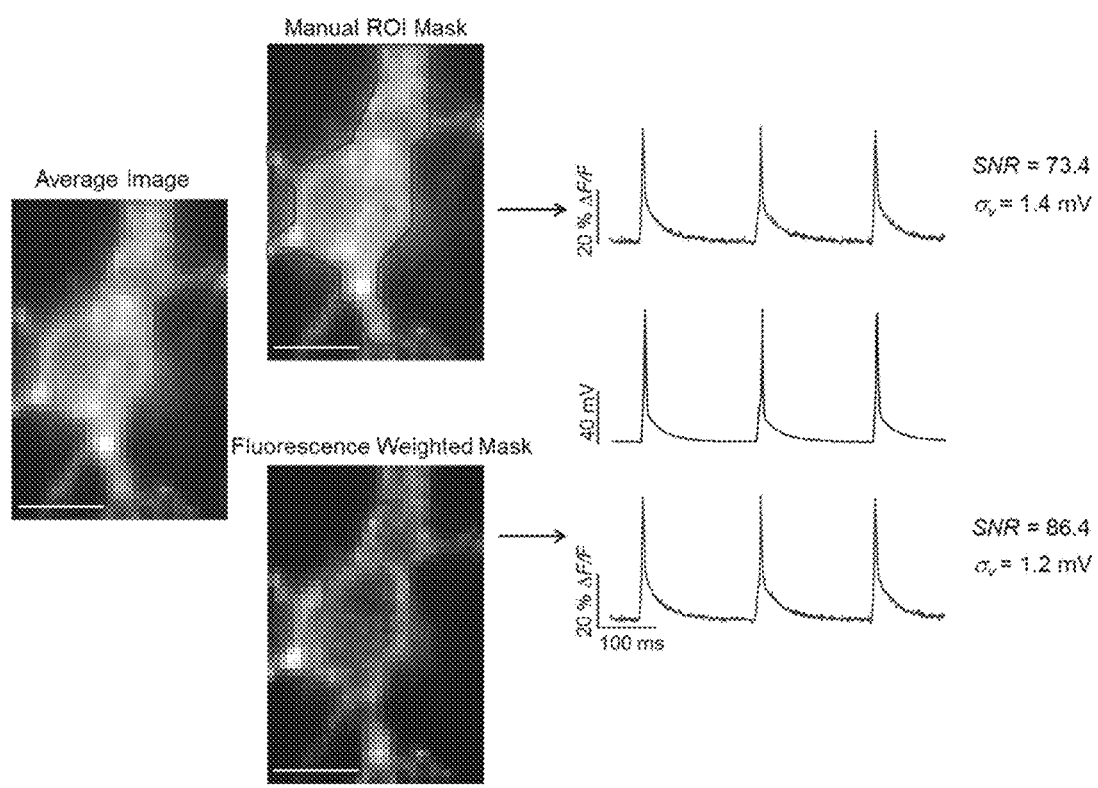
FIG. 10 shows the extraction of fluorescence traces from QuasAr movies. Fluorescence can either be calculated by manually defining a region of interest (ROI; top row), or by preferentially weighting the pixels whose intensity co-varies with the whole-field average (bottom row)[10]. The noise in the fluorescence trace when scaled to match the electrical recording is denoted σ$_v$. With the improved trafficking of the QuasAr mutants compared to Arch, the automated technique gave only slightly higher SNR than manual definition of the ROI. The technique makes no use of the electrode readout. Cell shown is the source of the data in FIG. 1G. All comparisons of SNR in culture were made on measurements taken with the same 60× objective, collected on the same EMCCD, and extracted using this automated technique. For recordings on cultured neurons, values of ΔF/F were calculated after subtracting background autofluorescence from a cell-free region of the field of view. This background subtraction was not performed on recordings in tissue.

With the improved trafficking of the QuasAr mutants compared to Arch, the maximum likelihood pixel-weighting algorithm was only marginally superior to manual definition of an region of interest (ROI) (FIG. 10). In measurements in brain slice, fluorescence was calculated from manually defined ROIs with equal pixel weighting and no background subtraction or correction for photobleaching.

Precision of optically recorded AP timing: To determine the temporal precision of the QuasAr indicators, we used the sub-frame interpolation algorithm[37,38] to infer the timing with which the fluorescence reached 70% of maximum at each AP, and compared to simultaneously acquired high time-resolution patch clamp recordings. Root-mean-square (r.m.s.) temporal jitter was 44 μs for QuasAr1 (n=97 APs) and 61 μs for QuasAr2 (n=99 APs). This jitter reflects the combined errors in timing intrinsic to the optical measurement (shot-noise and distortion of the waveform by the reporter) and errors introduced by temporal discretization of the camera frames and the sub-frame interpolation. Thus optical recordings with QuasArs can determine spike timing with precision much greater than the camera exposure time.

Sub-Frame Interpolation of AP Timing.

The sub-frame interpolation algorithm consists of a series of computational image-processing steps. Each step may be modified to account for experiment-specific attributes of the data.

A neuron was induced to fire through repeated optical stimulation of a user-selected subcellular compartment (typically soma or dendrite). We typically observed 5% photobleaching over a 40 s acquisition. Photobleaching was typically dominated by non-specific background fluorescence, rather than by photobleaching of QuasAr, and often photobleaching did not follow a simple single-exponential decay. The photobleaching baseline was constructed from the whole-field intensity by a sliding minimum filter, followed by a sliding mean filter. Each frame of the movie was then corrected by dividing by this baseline.

QuasAr fluorescence intensity $F(t)$ was determined either by the regression algorithm[10] or by whole-field average intensity. Both procedures gave similar results, with slightly better signal-to-noise ratio returned by the regression algorithm (FIG. 2).

Determination of spike times was performed iteratively. A simple threshold-and-maximum procedure was applied to $F(t)$ to determine approximate spike times, $\{T_0\}$. Waveforms in a brief window bracketing each spike were averaged together to produce a preliminary spike kernel $K_0(t)$. We then calculated the cross-correlation of $K_0(t)$ with the original intensity trace $F(t)$. Whereas the timing of maxima in $F(t)$ was subject to errors from single-frame noise, the peaks in the cross-correlation, located at times $\{T\}$, were a robust measure of spike timing. A movie showing the mean AP propagation was constructed by averaging movies in brief windows bracketing spike times $\{T\}$. Typically 100-400 APs were included in this average. The AP movie had high signal-to-noise ratio, but did not clearly show signal propagation.

We applied spatial and temporal linear filters to further decrease the noise in AP movie. The spatial filter consisted of convolution with a Gaussian kernel, typically with a standard deviation of 1 pixel. The temporal filter was based upon Principal Components Analysis (PCA) of the set of single-pixel time traces. The time trace at each pixel was expressed in the basis of PCA eigenvectors. Typically the first 5 eigenvectors were sufficient to account for >99% of the pixel-to-pixel variability in AP waveforms, and thus the PCA eigendecomposition was truncated after 5 terms. The remaining eigenvectors represented uncorrelated shot noise. Projections of the movie onto the PCA eigenvectors only showed spatial features above noise for the first 5 eigenvectors. To verify that the spatial and PCA filtering did not distort the underlying AP waveforms, we compared mean AP waveforms in subcellular compartments before and after the smoothing steps. We observed no systematic deviations in the AP waveforms in the axon, soma, or dendrites.

The user then set a threshold depolarization to track (represented as a fraction of the maximum fluorescence transient), and a sign for dV/dt (indicating rising or falling edge). We chose 50% maximal depolarization on the rising edge. The filtered data was fit with a quadratic spline interpolation and the time of threshold crossing was calculated for each pixel. The sub-frame timing precision of the algorithm was calibrated by patch clamp measurements. Optically induced APs were recorded simultaneously via QuasAr1 fluorescence in the soma and by conventional patch clamp, also in the soma. The r.m.s. error in timing was 54 µs in this instance, and did not show systematic bias at the frame boundaries.

The fits were converted into movies showing AP propagation as follows. Each pixel was kept dark except for a brief flash timed to coincide with the timing of the user-selected AP feature at that pixel. The flash followed a Gaussian timecourse, with amplitude equal to the local AP amplitude, and duration equal to the cell-average time resolution, σ. Frame times in the sub-frame interpolation movies were selected to be ~2-fold shorter than σ.

Occasionally it was possible to enhance the spatial resolution of the high temporal resolution movies by mapping the timing data onto a higher spatial resolution static image of fluorescence of QuasAr1. The pixel matrix of the sub-frame interpolated movie was expanded to match the dimensions of the high resolution image and the amplitude at each pixel was then set equal to the mean brightness at that pixel. AP initiation at the axon initial segment is visible in the first two frames.

Example 1: Directed Evolution and Engineering of an Arch-Based Voltage Indicator We previously showed that Archaerhodopsin 3 (Arch) functions as a fast and sensitive voltage indicator.[10] Arch has the furthest red-shifted spectrum of any GEVI, giving it the unique property of little spectral overlap with channelrhodopsin actuators and GFP-based reporters. Thus it is natural to pair Arch-based indicators with optogenetic actuators for crosstalk-free all-optical electrophysiology.

However, wild-type Arch had some undesirable attributes for a reporter: it was very dim, and the brightness was a nonlinear function of illumination intensity.[24] Illumination for imaging generated a hyperpolarizing photocurrent, which partially suppressed neural firing. The mutant Arch (D95N) did not pump, but its step response was dominated by a 41 ms time constant, too slow to resolve action potential (AP) waveforms.

We sought to repair these defects in engineered mutants of Arch. To accommodate the multiple selection criteria, we adopted a hierarchical screen (FIG. 1A). Five rounds of brightness screening in *E. coli* and random mutagenesis on a library of >$10^4$ Arch mutants resulted in a brighter Arch variant, containing 5 point-mutations (Methods). Further site-directed mutagenesis at known key residues improved voltage sensitivity and speed (FIG. 2), while membrane trafficking was improved by the addition of endoplasmic reticulum (ER) export motifs and a trafficking sequence (TS).[25] Two promising mutants were named QuasArs (Quality superior to Arch). QuasAr1 comprised mutations at P60S, T80S, D95H, D106H, F161V and QuasAr2 comprised mutations at P60S, T80S, D95Q, D106H, F161V. FIG. 3 shows absorption, fluorescence excitation, and emission spectra of the solubilized QuasAr proteins. The fluorescence quantum yields of solubilized QuasAr1 and 2 were 19- and 10-fold enhanced, respectively, relative to the non-pumping voltage indicator Arch(D95N) (Table 5). Table 5 shows the quantum yields of Arch variants measured in solubilized protein. Fluorescence emission spectra were recorded with excitation at 600 nm. Details of sample preparation and measurement procedures are given in Materials and Methods.

TABLE 5

| Protein Name | Quantum yield | Quantum yield relative to Arch D95N |
| --- | --- | --- |
| Arch | N/A* | N/A* |
| Arch D95N | $4 \times 10^{-4}$ | 1 |
| QuasAr1 | $8 \times 10^{-3}$ | 19 |
| QuasAr2 | $4 \times 10^{-3}$ | 10 |
| Arch D95H/D106H | $2 \times 10^{-3}$ | 4.2 |
| Arch D95H/D106H/P60S | $5 \times 10^{-3}$ | 12 |
| Arch D95H/D106H/F161V | $5 \times 10^{-3}$ | 13 |

*Due to the low light intensities used to determine QYs, fluorescence from Arch was not detected above baseline.

We compared the fluorescence, voltage sensitivity, and speed of the QuasArs to wild-type Arch in HEK cells, using epifluorescence microscopy and whole-cell patch clamp electrophysiology. Under low intensity illumination (640 nm, 500 mW/cm$^2$), QuasAr1 was 15-fold brighter than wild-type Arch, and QuasAr2 was 3.3-fold brighter (FIG. 1B; Methods). Neither mutant showed the optical nonlinearity seen in the wild-type protein, implying that fluorescence was a 1-photon process with the voltage-sensitive transition occurring from the ground state. At high intensity (>100 W/cm$^2$) QuasAr1 was 2.5-fold brighter than wild-type Arch, while the brightness of QuasAr2 and of wild-type Arch were comparable.

Fluorescence of Arch, QuasAr1, and QuasAr2 increased nearly linearly with membrane voltage between −100 mV and +50 mV (FIG. 1C). Sensitivities were (ΔF/F per 100 mV): 32±3% for QuasAr1 (n=5 cells; all statistics are mean±s.e.m. unless specified) and 90±2% for QuasAr2 (n=6 cells). The sensitivity of QuasAr2 is a significant improvement over both Arch (40% per 100 mV) and Arch(D95N) (60% per 100 mV).

Steps in membrane voltage (−70 mV to +30 mV) induced rapid fluorescence responses in both mutants, which we quantified on a fast photomultiplier (FIG. 1D). At room temperature (23° C.) QuasAr1 had a step response time constant of 0.053±0.002 ms (n=6 cells), close to the 0.05 ms time resolution of the electronics and significantly faster than the 0.6 ms step response of wild-type Arch.[24] QuasAr2 had a bi-exponential step response with time constants of 1.2±0.1 ms (68%) and 11.8±1.5 ms (32%) (n=6 cells). At 34° C., the apparent speed of QuasAr1 remained at the 0.05 ms resolution of the electronics, and the time constants of QuasAr2 decreased to 0.30±0.05 ms (62%) and 3.2±0.4 ms (38%) (n=7 cells). Both mutants had similar response times on rising and falling edges (Table 6). Table 6 shows spectroscopic and kinetic properties of Arch mutants and ArcLight. Brightness, response speed, and sensitivity were measured in HEK293 cells. Brightness and voltage sensitivity were comparable at 34° C. and 23° C. Fluorescence response time to a voltage step (−70 mV to +30 mV and +30 mV to −70 mV) are shown. Fluorescence emission spectra were recorded with excitation at 600 nm. Photocurrent (pA) in neurons (300 W/cm², 640 nm) for Arch (WT) is 220±30 and 0 in both QuasAr1 and QuasAr2. Details of sample preparation and measurement procedures are given in the General Experimental Methods section.

TABLE 6

| Mutant | Brightness ($\lambda_{exc}$ = 640 nm) 0.7 W/cm² | Brightness 800 W/cm² | $\tau_{up}$ (ms, −70 mV to +30 mV) $\tau_1$ | $\tau_2$ | % $\tau_1$ | $\tau_{down}$ (ms, +30 mV to −70 mV) $\tau_1$ | $\tau_2$ | % $\tau_1$ | Sensitivity (ΔF/F per 100 mV) |
|---|---|---|---|---|---|---|---|---|---|
| 23° C. | | | | | | | | | |
| Arch(WT) | 1 | 4.0 | 0.6 | NA | NA | 0.25 | 1.9 | 67% | 40% |
| QuasAr1 | 15.2 | 10.3 | 0.05 | 3.2 | 94% | 0.07 | 1.9 | 88% | 33% |
| QuasAr2 | 3.4 | 3.4 | 1.2 | 11.8 | 68% | 1.0 | 15.9 | 80% | 90% |
| Arclight A242 | | | 17.4 | 123 | 39% | 68 | 121 | 24% | −32% |
| 34° C. | | | | | | | | | |
| QuasAr2 | | | 0.3 | 3.2 | 62% | 0.3 | 4.0 | 73% | |
| Arclight A242 | | | 12 | 72 | 78% | 21.5 | NA | 100% | |

In cultured rat hippocampal neurons, wild-type Arch generated photocurrents of 220±30 pA (n=6 cells) under red illumination often used for imaging (640 nm, 300 W/cm²) and 140±25 pA under blue light used for optogenetic stimulation (488 nm, 500 mW/cm²) (FIG. 4). These currents hyperpolarized cells by 25±4 mV and 19±3 mV, respectively. Neither QuasAr1 nor QuasAr2 generated detectable photocurrent in neurons under red light (tested up to 900 W/cm²) or blue light (FIG. 4).

Figure 1F:
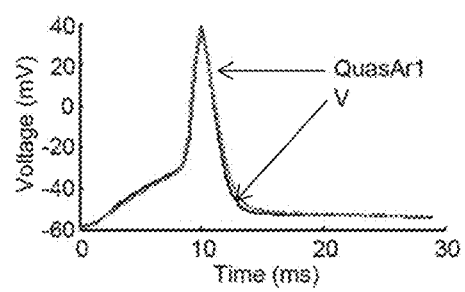
Figure 1G:
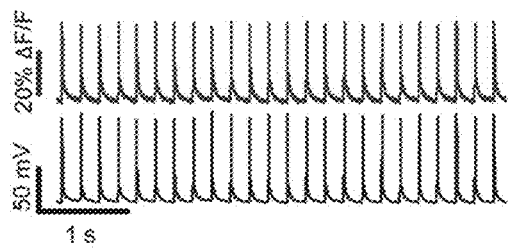

Fluorescence of QuasAr1 and QuasAr2 reported APs in cultured neurons with high electrical and temporal precision (FIG. 1E-H). We evoked APs via current injection from a patch pipette and recorded the fluorescence responses of QuasAr1 and 2 under two standard illumination intensities (640 nm; 300 W/cm², 800 W/cm²). FIG. 10 shows a typical cell and the method used for extracting fluorescence from movies. In recordings at a 1 kHz frame rate signal-to-noise ratios (SNRs) for single APs were 21±2 (300 W/cm², n=6 cells) to 32±4 (800 W/cm², n=6 cells) for QuasAr1 (FIG. 1E) and 41±4 (300 W/cm², n=12 cells) to 70±8 (800 W/cm², n=12 cells) for QuasAr2 (FIG. 1G). These SNRs correspond to equivalent electrical noise levels of 3.0 to 4.3 mV (800 to 300 W/cm²) for QuasAr1, or 1.5 to 2.2 mV (800 to 300 W/cm²) for QuasAr2 (Methods).

Figure 1H:
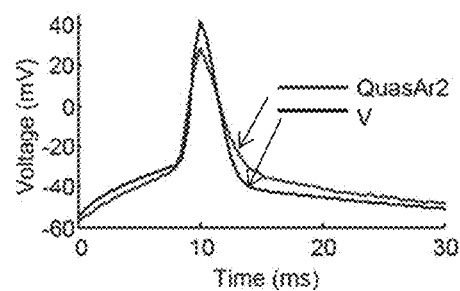
Figure 2A:
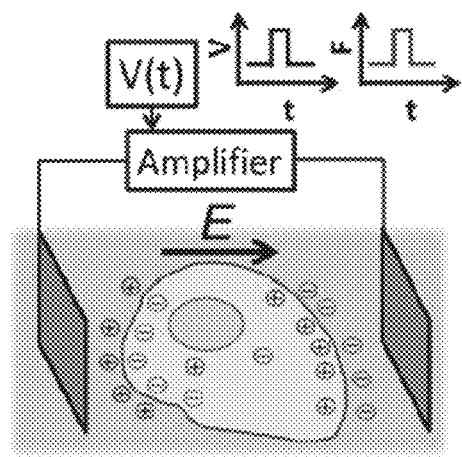
FIGS. 2A-2D show induced transmembrane voltage (ITV) in Arch-expressing HeLa cells.
Figure 2B:
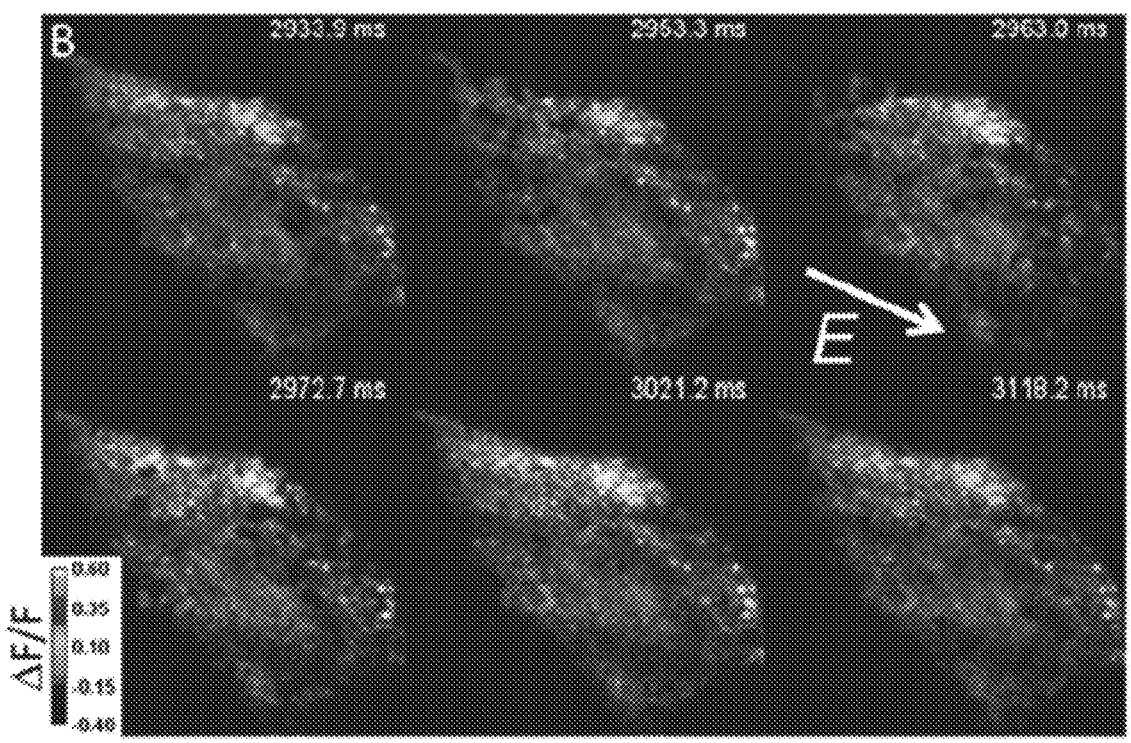
Figure 2C:
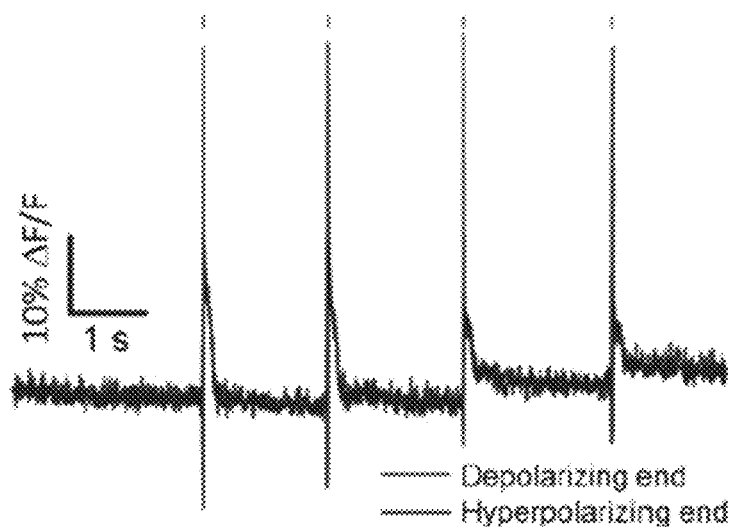
Figure 2D:
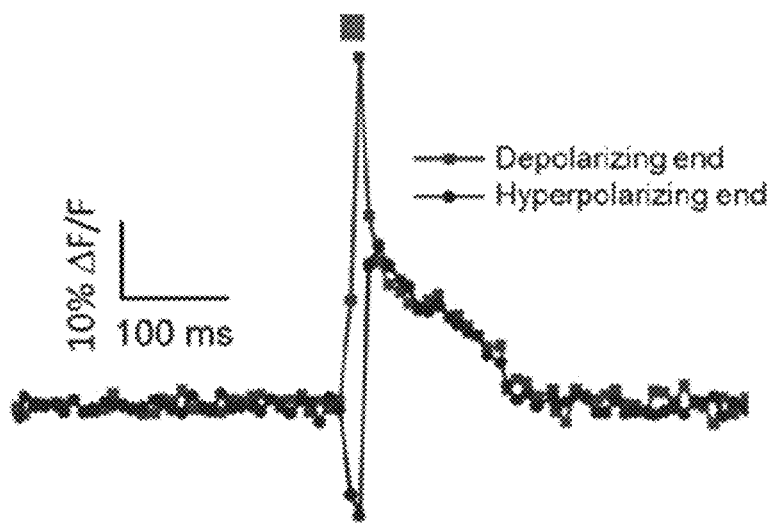
Figure 3A:
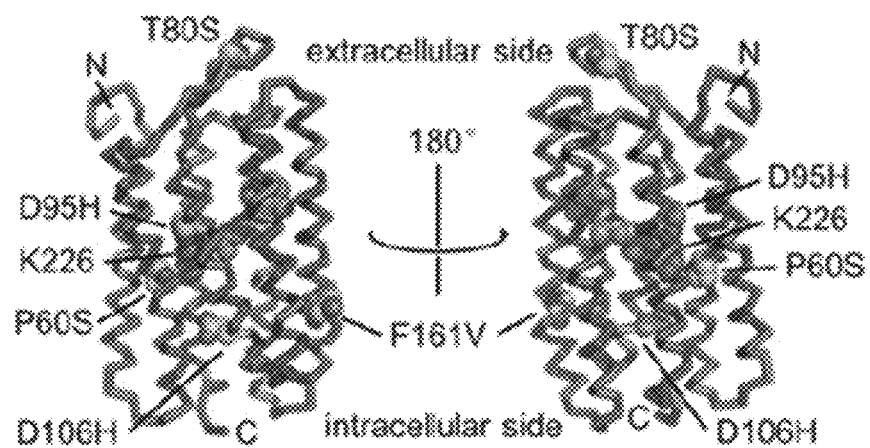
FIGS. 3A-3D show the structural and spectroscopic properties of QuasArs.
Figure 3B:
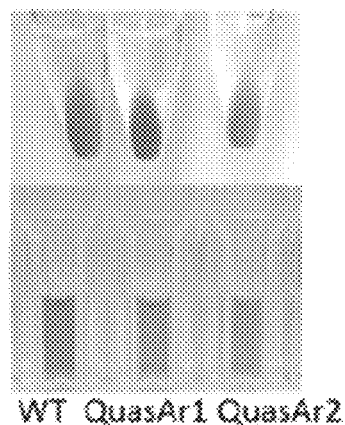
Figure 3C:
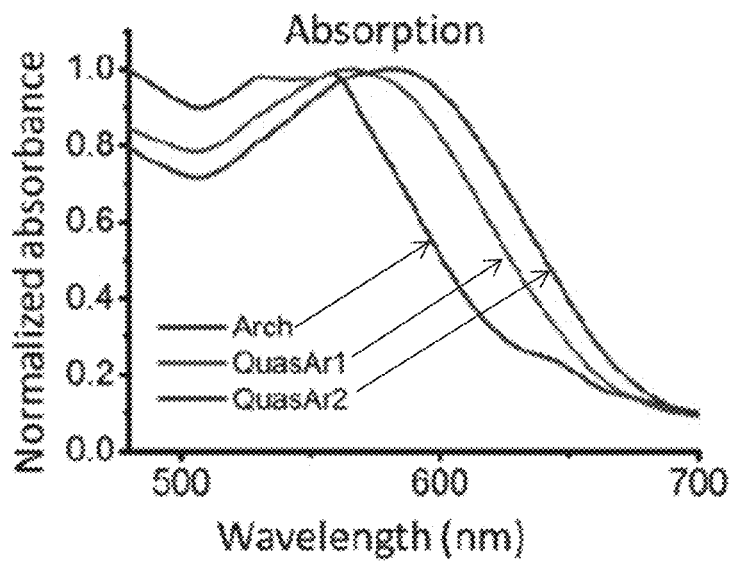
Figure 3D:
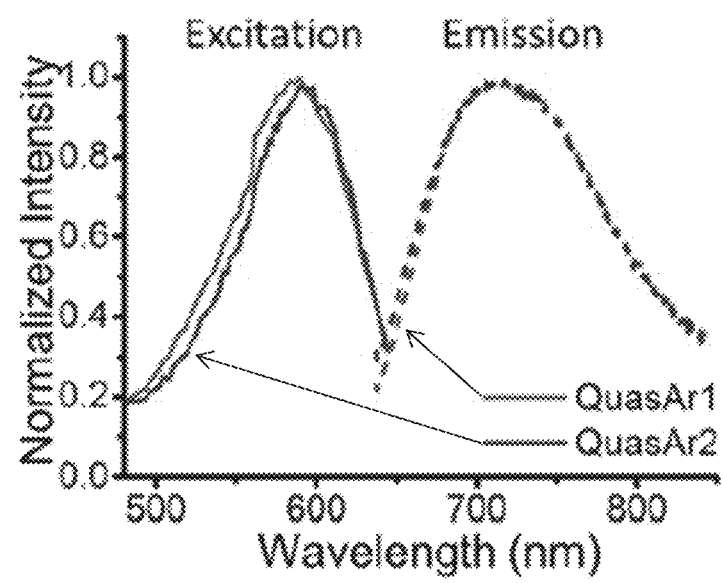

QuasAr1 did not introduce detectable broadening in the optically recorded AP waveform, acquired at a 2 kHz frame rate (FIG. 1F). At room temperature, QuasAr2 broadened the optically recorded AP by 650±150 μs relative to the simultaneously recorded electrical waveform at 70% maximum depolarization (n=5 cells; mean±s.d.) (FIG. 1H). At 34° C., QuasAr2 broadened the optically recorded AP by 180±120 As (n=5 cells; mean±s.d). Both probes reported AP peak times with <100 μs jitter relative to simultaneously acquired patch clamp recordings (Methods).

Photostability is a concern with any voltage indicator, so we quantified the stability of QuasArs under continuous illumination at standard imaging intensity (640 nm, 300 W/cm²). Photobleaching time constants were 440 s for QuasAr1 and 1020 s for QuasAr2. We further tested for red light-induced phototoxicity using QuasAr2 as the readout. Under continuous illumination at 300 W/cm², QuasAr2 reported APs with 100% fidelity for the 30 min duration of the experiment, with no detectable change in AP width or waveform.

The QuasArs represent the fastest and most sensitive GEVIs reported to-date. The 50 μs response time of QuasAr1 is more than 10-fold faster than the fastest previously reported GEVIs[24,26] and is comparable to fast voltage-sensitive dyes. QuasAr1 opens the possibility of accurate mapping of AP waveforms for even the fastest-spiking neurons.[27] The illumination for imaging QuasArs, while intense, is ~5-fold lower than required for imaging Arch or Arch(D95N),[1] yet the QuasArs report voltage with greatly improved sensitivity and time resolution compared to the first generation of Arch-based GEVIs. From a signal-to-noise perspective, QuasAr2 is superior to QuasAr1: the greater voltage sensitivity of QuasAr2 outweighs the greater brightness of QuasAr1. From a temporal resolution perspective, QuasAr1 is superior. We recommend QuasAr2 for spike counting and measurement of sub-threshold events, and QuasAr1 for measurement of microsecond-precision AP waveforms and timing.

Example 2: Comparison of QuasArs to Arclight

Figure 9D:
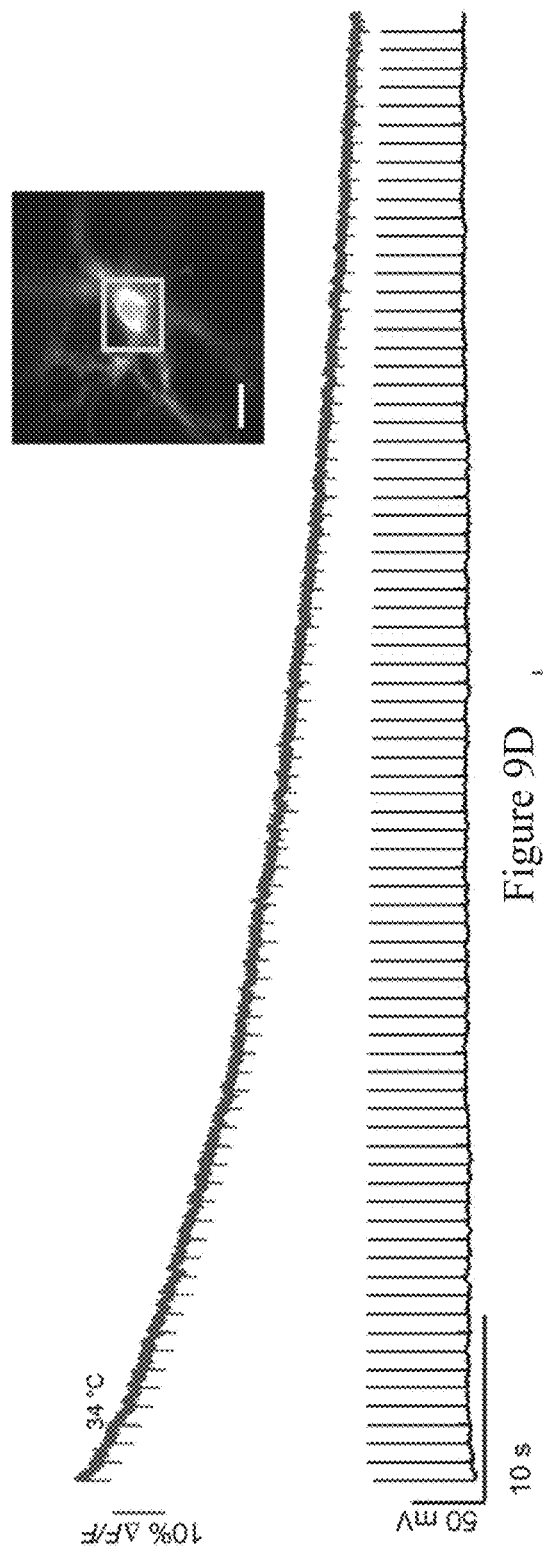
Figure 9E:
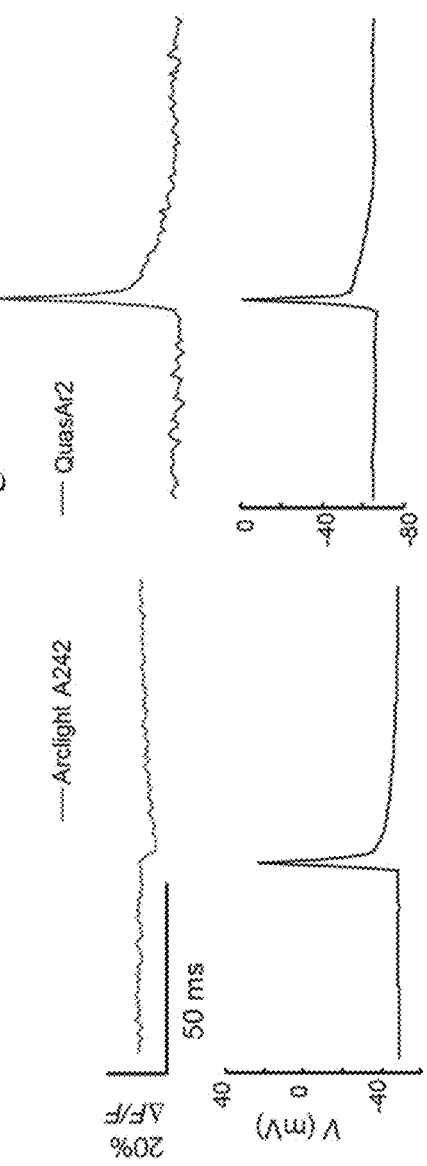

We compared the QuasArs to Arclight A242, a recently introduced GFP-based GEVI.[23] Photophysical comparisons were performed in HEK cells, and action potential comparisons were performed in matched neuronal cultures (Methods). Arclight showed voltage sensitivity of −32±3% ΔF/F per 100 mV (n=7 cells; FIG. 9), comparable in magnitude to QuasAr1 and 2.8-fold smaller than QuasAr2. Arclight showed bi-exponential kinetics in response to rising or falling voltage steps (FIG. 9, Table 6). Mean half-response times were 42±8 ms and 76±5 ms on rising and falling edges at 23° C. (n=6 cells) and 11±1 and 17±2 ms on rising and falling edges at 34° C. (n=7 cells). Under continuous illumination at standard imaging intensity (488 nm, 10 W/cm²)[11] Arclight photobleached with a time constant of 70 s. In cultured neurons, Arclight reported action potentials with an amplitude of ΔF/F=−2.7±0.5% (n=5 cells) and a single-trial signal-to-noise ratio (SNR) of 8.8±1.6 when recorded at a 1 kHz frame rate (488 nm, 10 W/cm²) (Methods). Arclight distorted the AP waveforms to have a width of 14.5±3.0 ms at 70% maximal fluorescence deviation, compared to the true width of 1.3±0.1 ms simultaneously recorded with a patch pipette.

The Arclight reporter can be imaged with ~30-fold lower illumination intensity than is required for the QuasArs, facilitating measurements on readily available microscope systems. The QuasArs reported action potentials with 7 to 16-fold larger fractional fluorescence changes, 3 to 8-fold higher SNR, 30 to 1000-fold higher temporal resolution, and 6 to 15-fold greater photostability. Furthermore, the far red excitation of the QuasArs allow, in principle, combination with channelrhodopsin actuators. This is not possible with Arclight or other GFP-based GEVIs.

Example 3: Electrochromic Fluorescence Resonance Energy Transfer (eFRET)-Based GEVIs Importance of Spectral Tunability in GEVIs.

The spectral range of GEVIs is important when combining GEVIs with other GEVIs, other optical reporters, or optogenetic actuators. Having GEVIs of multiple colors enables multiplex voltage imaging when distinct structures cannot be spatially resolved. For instance, to study separately excitatory and inhibitory neurons in intact tissue would require two colors of GEVIs. Furthermore, GFP-based GEVIs cannot be paired with other GFP-based reporters, e.g. gCaMP reporters of $Ca^{2+}$,[9] iGluSnFR reporter of glutamate,[80] Perceval reporter of ATP,[81] Clomelion reporter of $Cl^-$,[82] Pyronic reporter of pyruvate.[83] GFP-based reporters also experience severe optical crosstalk with all optogenetic actuators. Even the reddest channelrhodopsin variants retain ~20% activation with blue light used for GFP excitation.[84]

Spectral range is also important for imaging in intact tissue. The excitation and emission spectra of flavins, a major contributor to brain autofluorescence, overlap strongly with those of GFP.[85,86] Consequently, a rule of thumb is that the signal-to-background ratio for GFP-based reporters is 10-fold lower in tissue than in cell culture. Redder reporters have significantly less background in brain tissue. Furthermore light scattering in tissue scales as $\lambda^{-x}$, where x~2.33[16]. Thus illumination at 640 nm propagates nearly 1.9-fold further into tissue than does illumination at 488 nm. While two-photon excitation of GFP-based reporters enables even greater depth penetration, this comes at the cost of requiring serial scanning, and a complex optical setup.

DETAILED DESCRIPTION

We invented a means to combine the high speed and sensitivity of Arch-based GEVIs with the brightness and spectral range of conventional fluorescent proteins. We use voltage-induced changes in the absorption spectrum of the retinal chromophore in Arch to alter the degree of nonradiative quenching of a closely fused fluorescent protein. Traditionally, fluorescence resonance energy transfer (FRET) is used to measure the physical distance between a donor and acceptor. We use electrochromic shifts in the acceptor to alter the degree of spectral overlap between the emission of the donor and the absorption of the acceptor, thus we call the phenomenon electrochromic FRET (eFRET) (FIG. 6).

The electrochromic quencher was QuasAr2, which was shown to exhibit fast and sensitive changes in fluorescence in response to changes in membrane voltage. The changes in fluorescence likely arose from changes in the absorption spectrum, so we reasoned that QuasAr2 would be an effective tool for voltage-dependent quenching of an appended fluorescent protein.

We invented five fast and sensitive GEVIs based upon fusions spanning the visible spectrum. We created a palette of eFRET constructs by fusing GFP, YFP, citrine, mOrange2, mKate2 and mRuby2 to the C-terminus of QuasAr2 via a short linker. We expressed these constructs in HEK293 cells and tested the voltage sensitivity and step response using manual patch-clamp electrophysiology (FIG. 7).

We further characterized the most sensitive eFRET voltage sensors via transient transfection in cultured rat hippocampal neurons. Constructs exhibited good trafficking to the plasma membrane (FIG. 8). Injection of current pulses via a patch pipette (500-600 pA, 5-10 ms, 5 Hz) induced trains of action potentials, which induced downward fluorescence transients of 12% (YFP), 12% (mOrange2), 7% (mRuby2).

The signal-to-noise ratio (SNR) of fluorescence detection, defined as the ratio of the peak amplitude to standard deviation of fluorescence at the baseline, was 6.6 (YFP), 11.6 (mOrange2), and 10.5 (mRuby2). In all cases images were acquired at 1 kHz with 3 $W/cm^2$ illumination intensity. Previous measurements with QuasAr2 reported an SNR of 30-70 at the same bandwidth but with 800 $W/cm^2$ illumination. At 3 $W/cm^2$ illumination, the direct fluorescence of QuasAr2 is not detectable for exposure times compatible with detecting single action potentials.

This work opens the possibility of multicolor voltage imaging with GEVIs spanning the visible spectrum.

REFERENCES RECITED HEREIN

1. Peron, S. & Svoboda, K. From cudgel to scalpel: toward precise neural control with optogenetics. Nat. Meth. 8, 30-34 (2010).
2. Petreanu, L., Mao, T., Sternson, S. M. & Svoboda, K. The subcellular organization of neocortical excitatory connections. Nature 457, 1142-1145 (2009).
3. Scanziani, M. & Hausser, M. Electrophysiology in the age of light. Nature 461, 930-939 (2009).
4. Boulting, G. L. et al. A functionally characterized test set of human induced pluripotent stem cells. Nat. Biotechnol. 29, 279-286 (2011).
5. Furuta, T. et al. Brominated 7-hydroxycoumarin-4-ylmethyls: photolabile protecting groups with biologically useful cross-sections for two photon photolysis. Proc. Nat. Acad. Sci. U.S.A. 96, 1193-1200 (1999).
6. Kramer, R. H., Fortin, D. L. & Trauner, D. New photochemical tools for controlling neuronal activity. Curr. Opin. Neurobiol. 19, 544-552 (2009).
7. Boyden, E. S., Zhang, F., Bamberg, E., Nagel, G. & Deisseroth, K. Millisecond-timescale, genetically targeted optical control of neural activity. Nat. Neurosci. 8, 1263-1268 (2005).
8. Bernstein, J. G., Garrity, P. A. & Boyden, E. S. Optogenetics and thermogenetics: technologies for controlling the activity of targeted cells within intact neural circuits. Curr. Opin. Neurobiol. 22, 61-71 (2011).
9. Chen, T. et al. Ultrasensitive fluorescent proteins for imaging neuronal activity. Nature 499, 295-300 (2013).
10. Kralj, J. M., Douglass, A. D., Hochbaum, D. R., Maclaurin, D. & Cohen, A. E. Optical recording of action potentials in mammalian neurons using a microbial rhodopsin. Nat. Meth. 9, 90-95 (2012).
11. Cao, G. et al. Genetically Targeted Optical Electrophysiology in Intact Neural Circuits. Cell 154, 904-913 (2013).

12. Lam, A. J. et al. Improving FRET dynamic range with bright green and red fluorescent proteins. *Nat. Meth.* 9, 1005-1012 (2012).
13. Siegel, M. S. & Isacoff, E. Y. A Genetically Encoded Optical Probe of Membrane Voltage. *Neuron* 19, 735-741 (1997).
14. Akemann, W. et al. Two-photon voltage imaging using a genetically encoded voltage indicator. *Nat. Rep.* 3, 2231 (2013).
15. Miller, E. W. et al. Optically monitoring voltage in neurons by photo-induced electron transfer through molecular wires. *Proc. Nat. Acad. Sci. U.S.A.* 109, 2114-2119 (2012).
16. Yan, P. et al. Palette of fluorinated voltage-sensitive hemicyanine dyes. *Proc. Nat. Acad. Sci. U.S.A.* 109, 20443-20448 (2012).
17. Vogt, K. E., Gerharz, S., Graham, J. & Canepari, M. Combining membrane potential imaging with L-glutamate or GABA photorelease. *PLoS One* 6, e24911 (2011).
18. Canepari, M., Zecevic, D., Vogt, K. E., Ogden, D. & De Waard, M. Combining calcium imaging with other optical techniques. *Cold Spring Harbor Protocols* 2013, pdb. top066167 (2013).
19. Wu, J. et al. Improved orange and red $Ca^{2+}$ indicators and photophysical considerations for optogenetic applications. *ACS Chem. Neuro.* 4, 963-972 (2013).
20. Tsuda, S. et al. Probing the function of neuronal populations: combining micromirror-based optogenetic photostimulation with voltage-sensitive dye imaging. *Neurosci. Res.* 75, 76-81 (2012).
21. Lim, D. H. et al. In vivo Large-Scale Cortical Mapping Using Channelrhodopsin-2 Stimulation in Transgenic Mice Reveals Asymmetric and Reciprocal Relationships between Cortical Areas. *Front. Neural Circuits* 6, 11 (2012).
22. Klapoetke, N. C. et al. Independent optical excitation of distinct neural populations. *Nat. Meth.* 11, 338-346 (2014).
23. Jin, L. et al. Single action potentials and subthreshold electrical events imaged in neurons with a fluorescent protein voltage probe. *Neuron* 75, 779-785 (2012).
24. Maclaurin, D., Venkatachalam, V., Lee, H. & Cohen, A. E. Mechanism of voltage-sensitive fluorescence in a microbial rhodopsin. *Proc. Natl. Acad. Sci. USA* 110, 5939-5944 (2013).
25. Gradinaru, V. et al. Molecular and Cellular Approaches for Diversifying and Extending Optogenetics. *Cell* 141, 154-165 (2010).
26. Sakai, R., Repunte-Canonigo, V., Raj, C. D. & Knopfel, T. Design and characterization of a DNA-encoded, voltage-sensitive fluorescent protein. *Eur. J. Neurosci.* 13, 2314-2318 (2001).
27. Bean, B. P. The action potential in mammalian central neurons. *Nature Reviews Neuroscience* 8, 451-465 (2007).
28. Schoenenberger, P., Grunditz, Å., Rose, T. & Oertner, T. G. Optimizing the spatial resolution of Channelrhodopsin-2 activation. *Brain Cell. Biol.* 36, 119-127 (2008).
29. Wang, J., Hasan, M. T. & Seung, H. S. Laser-evoked synaptic transmission in cultured hippocampal neurons expressing channelrhodopsin-2 delivered by adeno-associated virus. *J. Neurosci Methods* 183, 165-175 (2009).
30. Mattis, J. et al. Principles for applying optogenetic tools derived from direct comparative analysis of microbial opsins. *Nat. Meth.* 9, 159-172 (2011).
31. Johnson, M. T. J. et al. Evaluating methods for isolating total RNA and predicting the success of sequencing phylogenetically diverse plant transcriptomes. *PLoS One* 7, e50226 (2012).
32. Melkonian, M. & Preisig, H. R. A light and electron microscopic study of *Scherffelia dubia*, a new member of the scaly green flagellates (Prasinophyceae). *Nord. J. Bot.* 6, 235-256 (1986).
33. Lin, J. Y., Lin, M. Z., Steinbach, P. & Tsien, R. Y. Characterization of engineered channelrhodopsin variants with improved properties and kinetics. *Biophys. J.* 96, 1803-1814 (2009).
34. Conrad W, L., Mohammadi, M., Santos, M. D. & Tang, C. M. Patterned photostimulation with digital micromirror devices to investigate dendritic integration across branch points. *J. Vis. Exp.* 49, e2003 (2011).
35. Takahashi, H. et al. Light-addressed single-neuron stimulation in dissociated neuronal cultures with sparse expression of ChR2. *BioSystems* 107, 106-112 (2012).
36. Fitzsimonds, R. M., Song, H. & Poo, M. Propagation of activity-dependent synaptic depression in simple neural networks. *Nature* 388, 439-448 (1997).
37. Foust, A., Popovic, M., Zecevic, D. & McCormick, D. A. Action potentials initiate in the axon initial segment and propagate through axon collaterals reliably in cerebellar Purkinje neurons. *J. Neurosci* 30, 6891-6902 (2010).
38. Popovic, M. A., Foust, A. J., McCormick, D. A. & Zecevic, D. The spatio-temporal characteristics of action potential initiation in layer 5 pyramidal neurons: a voltage imaging study. *J. Physiol.* 589, 4167-4187 (2011).
39. Kole, M. H. & Stuart, G. J. Signal processing in the axon initial segment. *Neuron* 73, 235-247 (2012).
40. Palmer, L. M. & Stuart, G. J. Site of action potential initiation in layer 5 pyramidal neurons. *J. Neurosci.* 26, 1854-1863 (2006).
41. Turrigiano, G., Abbott, L. & Marder, E. Activity-dependent changes in the intrinsic properties of cultured neurons. *Science* 264, 974-976 (1994).
42. Desai, N. S., Rutherford, L. C. & Turrigiano, G. G. Plasticity in the intrinsic excitability of cortical pyramidal neurons. *Nat. Neurosci.* 2, 515-520 (1999).
43. O'Leary, T., van Rossum, M. C. & Wyllie, D. J. Homeostasis of intrinsic excitability in hippocampal neurones: dynamics and mechanism of the response to chronic depolarization. *J. Physiol.* 588, 157-170 (2010).
44. Hengen, K. B., Lambo, M. E., Van Hooser, S. D., Katz, D. B. & Turrigiano, G. G. Firing Rate Homeostasis in Visual Cortex of Freely Behaving Rodents. *Neuron* 80, 335-342 (2013).
45. Lambo, M. E. & Turrigiano, G. G. Synaptic and intrinsic homeostatic mechanisms cooperate to increase L2/3 pyramidal neuron excitability during a late phase of critical period plasticity. *J. Neurosci.* 33, 8810-8819 (2013).
46. Trounson, A., Shepard, K. A. & DeWitt, N. D. Human disease modeling with induced pluripotent stem cells. *Curr. Opin. Genet. Dev.* 22, 509-516 (2012).
47. Shcheglovitov, A. et al. SHANK3 and IGF1 restore synaptic deficits in neurons from 22q13 deletion syndrome patients. *Nature* doi:10.1038/nature12618 (2013).
48. Grubb, M. S. & Burrone, J. Activity-dependent relocation of the axon initial segment fine-tunes neuronal excitability. *Nature* 465, 1070-1074 (2010).
49. Akemann, W. et al. Imaging neural circuit dynamics with a voltage-sensitive fluorescent protein. *J. Neurophysiol.* 108, 2323-2337 (2012).

50. Huys, Q. J., Ahrens, M. B. & Paninski, L. Efficient estimation of detailed single-neuron models. *J. Neurophysiol.* 96, 872-890 (2006).
51. Williams, J. C. et al. Computational optogenetics: empirically-derived voltage- and light-sensitive channelrhodopsin-2 model. *PLoS Comp. Biol.* 9, e1003220 (2013).
52. Hou, J. H., Venkatachalam, V. & Cohen, A. E. Temporal Dynamics of Microbial Rhodopsin Fluorescence Reports Absolute Membrane Voltage. *Biophys. J.* 106, 639-648 (2014).
53. Quinlan, K. A. Links between electrophysiological and molecular pathology of amyotrophic lateral sclerosis. *Integrative and comparative biology* 51, 913-925 (2011).
54. Sareen, D. et al. Targeting RNA foci in iPSC-derived motor neurons from ALS patients with a C9ORF72 repeat expansion. *Sci. Trans. Med.* 5, 208ra149 (2013).
55. Higurashi, N. et al. A human Dravet syndrome model from patient induced pluripotent stem cells. *Molec. Brain* 6, 19 (2013).
56. Badger, J., Cordero-Llana, O., Hartfield, E. & Wade-Martins, R. Parkinson's disease in a dish-Using stem cells as a molecular tool. *Neuropharmacology* 76, 88-96 (2014).
57. Marchetto, M. C. et al. A model for neural development and treatment of Rett syndrome using human induced pluripotent stem cells. *Cell* 143, 527-539 (2010).
58. Auerbach, B. D., Osterweil, E. K. & Bear, M. F. Mutations causing syndromic autism define an axis of synaptic pathophysiology. *Nature* 480, 63-68 (2011).
59. Huggins, J. L. & Paninski, L. Optimal experimental design for sampling voltage on dendritic trees in the low-SNR regime. *J. Comput. Neurosci.* 32, 347-366 (2012).
60. Zhao, H., Giver, L., Shao, Z., Affholter, J. A. & Arnold, F. H. Molecular evolution by staggered extension process (StEP) in vitro recombination. *Nat. Biotechnol.* 16, 258-261 (1998).
61. Zhao, Y. et al. An expanded palette of genetically encoded $Ca^{2+}$ indicators. *Science* 333, 1888-1891 (2011).
62. Cheng, Z. & Campbell, R. E. Assessing the structural stability of designed β-hairpin peptides in the cytoplasm of live cells. *ChemBioChem* 7, 1147-1150 (2006).
63. Lanyi, J. K. Proton translocation mechanism and energetics in the light-driven pump bacteriorhodopsin. *Biochim. Biophys. Acta* 1183, 241-261 (1993).
64. Lanyi, J. K. Bacteriorhodopsin. *Annu. Rev. Physiol.* 66, 665-688 (2004).
65. Kolodner, P., Lukashev, E. P., Ching, Y. & Rousseau, D. L. Electric-field-induced Schiff-base deprotonation in D85N mutant bacteriorhodopsin. *Proc. Natl. Acad. Sci. U.S.A.* 93, 11618-11621 (1996).
66. Ma, D. et al. Role of ER export signals in controlling surface potassium channel numbers. *Science* 291, 316-319 (2001).
67. Kirkton, R. D. & Bursac, N. Engineering biosynthetic excitable tissues from unexcitable cells for electrophysiological and cell therapy studies. *Nat. Commun.* 2, 300 (2011).
68. Park, J. et al. Screening fluorescent voltage indicators in spontaneously spiking HEK cells. *PLoS One* in press (2013).
69. Pucihar, G. & Kotnik, T. Measuring the induced membrane voltage with di-8-ANEPPS. *J. Vis. Exp.* 33, e1659 (2009).
70. Enami, N. et al. Crystal structures of archaerhodopsin-1 and -2: Common structural motif in archaeal light-driven proton pumps. *J. Mol. Biol.* 358, 675-685 (2006).
71. Kleinlogel, S. et al. A gene-fusion strategy for stoichiometric and co-localized expression of light-gated membrane proteins. *Nat. Meth.* 8, 1083-1088 (2011).
72. Barondeau, D. P., Putnam, C. D., Kassmann, C. J., Tainer, J. A. & Getzoff, E. D. Mechanism and energetics of green fluorescent protein chromophore synthesis revealed by trapped intermediate structures. *Proc. Nat. Acad. Sci. U.S.A.* 100, 12111-12116 (2003).
73. McCarthy, K. D. & De Vellis, J. Preparation of separate astroglial and oligodendroglial cell cultures from rat cerebral tissue. *J. Cell Biol.* 85, 890-902 (1980).
74. Goslin, K. in *Culturing nerve cells* (eds Banker, G. & Goslin, K.) (The MIT Press, Cambridge, Mass., 1998).
75. Chen, G., Harata, N. C. & Tsien, R. W. Paired-pulse depression of unitary quantal amplitude at single hippocampal synapses. *Proc. Nat. Acad. Sci. U.S.A.* 101, 1063-1068 (2004).
76. Jiang, M. & Chen, G. High $Ca^{2+}$-phosphate transfection efficiency in low-density neuronal cultures. *Nat. Protocols* 1, 695-700 (2006).
77. Stoppini, L., Buchs, P. & Muller, 1). A simple method for organotypic cultures of nervous tissue. *J. Neurosci. Methods* 37, 173-182 (1991).
78. Mukamel, E. A., Nimmerjahn, A. & Schnitzer, M. J. Automated analysis of cellular signals from large-scale calcium imaging data. *Neuron* 63, 747-760 (2009).
79. Mutal, H. Akemann, W. & Knopfel, T. Genetically engineered fluorescent voltage reporter. *ACS Chemical Neuroscience* 3, 585-592 (2012).
80. Marvin, J. S. An optimized fluorescent probe for visualizing glutamate eurotransmission. *Nat. Methods* 10, 162-170 (2013).
81. Tantama, M., Martinez-Francois, J. R., Mongeon, R. & Yellen, G. Imaging energy status in live cells with a fluorescent biosensor of the intracellular ATP-to-ADP ratio. *Nature communications* 4 (2013).
82. Kuner, T. & Augustine, G. J. A genetically encoded ratiometric indicator for chloride: capturing chloride transients in cultured hippocampal neurons. *Neuron* 27, 447-459 (2000).
83. San Martin, A. et al. Imaging Mitochondrial Flux in Single Cells with a FRET Sensor for Pyruvate. *PloS one* 9, e85780 (2014).
84. Klapoetke, N. C. et al. Independent optical excitation of distinct neural populations. *Nature methods* (2014).
85. Chung, Y. G., Schwartz, J. A. & Sawaya, R. E. Diagnostic potential of laser-induced autofluorescence emission in brain tissue.
86. Lin, W., Toms, S. A., Motamedi, M., Jansen, E. D. & Mahadevan-Jansen, A. Brain tumor demarcation using optical spectroscopy; an in vitro study. *J. Biomed. Opt.* 5, 214-220 (2000).
87. Flock, S. T., Jacques, S. L., Wilson, B. C., Star, W. M. & van Gemert, M. J. Optical properties of Intralipid: a phantom medium for light propagation studies. *Lasers Surg. Med.* 12, 510-519 (1992).

EQUIVALENTS AND SCOPE

As used in this specification and the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A polynucleotide encoding a polypeptide having at least 80% identity to SEQ ID NO: 1, wherein the polypeptide comprises, relative to SEQ ID NO: 1, at least
    a first substitution mutation selected from the group consisting of D95Q and D106H; and
    a second substitution mutation selected from the group consisting of P60S, T80S, and F161V.

2. A nucleic acid construct comprising the polynucleotide of claim 1.

3. An expression vector comprising the polynucleotide of claim 1.

4. A cell comprising the polynucleotide of claim 1.

5. A cell comprising the vector of claim 3.

6. A kit comprising the polypeptide or variant thereof, polynucleotide or variant, nucleic acid construct, vector, or cell of any one of the preceding claims.

7. A method for measuring membrane potential in a cell expressing a nucleic acid encoding a microbial rhodopsin protein, the method comprising the steps of:

exciting, in vitro, at least one cell comprising the polynucleotide of claim 1 with light of at least one wave length; and detecting, in vitro, at least one optical signal from the at least one cell, wherein the level of fluorescence emitted by the at least one cell compared to a reference is indicative of the membrane potential of the cell.

8. An expression vector comprising a polynucleotide encoding: a polypeptide having at least 80% identity to SEQ ID NO: 1, wherein the polypeptide comprises, relative to SEQ ID NO: 1, at least the following mutations:

D95H or D95Q,

D106H, and one mutation selected from the group consisting of P60S, T80S, and F161V; and a promoter sequence to control the expression of the polypeptide.

9. The expression vector of claim 8, wherein the polypeptide comprises, relative to SEQ ID NO: 1, at least two mutations selected from the group consisting of P60S, T80S, and F161V.

10. The expression vector of claim 9, wherein the polypeptide comprises, relative to SEQ ID NO: 1, all three mutations of P60S, T80S, and F161V.

11. The expression vector of claim 10, wherein the polypeptide comprises an amino sequence of SEQ ID NO: 3.

12. The expression vector of claim 9, wherein the polypeptide comprises an amino sequence of SEQ ID NO: 2.

13. The expression vector of claim 9, wherein the polynucleotide further encodes a second polypeptide.

14. The expression vector of claim 13, wherein the second polypeptide is fluorescent.

15. The expression vector of claim 14, wherein the second polypeptide is mOrange2.

16. The expression vector of claim 13, wherein the second polypeptide is capable of indicating ion concentration.

* * * * *

UNITED STATES PATENT AND TRADEMARK OFFICE
CERTIFICATE OF CORRECTION

PATENT NO. : 10,457,715 B2
APPLICATION NO. : 15/362594
DATED : October 29, 2019
INVENTOR(S) : Adam Ezra Cohen et al.

Page 1 of 1

It is certified that error appears in the above-identified patent and that said Letters Patent is hereby corrected as shown below:

On the Title Page

At item (72), the place of residence of Inventor Yongxin Zhao "Edmondton (CA)" should be replaced with: --Edmonton (CA)--.

At item (72), the place of residence of Inventor Daniel Jed Harrison "Edmondton (CA)" should be replaced with: --Edmonton (CA)--.

Signed and Sealed this
Third Day of March, 2020

Andrei Iancu
*Director of the United States Patent and Trademark Office*

UNITED STATES PATENT AND TRADEMARK OFFICE
CERTIFICATE OF CORRECTION

PATENT NO. : 10,457,715 B2
APPLICATION NO. : 15/362594
DATED : October 29, 2019
INVENTOR(S) : Adam Ezra Cohen et al.

Page 1 of 2

It is certified that error appears in the above-identified patent and that said Letters Patent is hereby corrected as shown below:

On the Title Page

At item (72), the place of residence of Inventor Yongxin Zhao "Edmondton (CA)" should be replaced with: --Edmonton (CA)--.

At item (72), the place of residence of Inventor Daniel Jed Harrison "Edmondton (CA)" should be replaced with: --Edmonton (CA)--.

In the Specification

In Column 1, Lines 6-12, please change the sentence:
"The present application is a continuation of and claims priority under 35 U.S.C. § 120 to U.S. application Ser. No. 14/742,648, filed Jun. 17, 2015, which claims priority under 35 U.S.C. § 119(e) to U.S. provisional patent application Ser. No. 62/013,775, filed Jun. 18, 2014, each of which is incorporated herein by reference."

To:
--The present application is a continuation of and claims priority under 35 U.S.C. § 120 to U.S. Application, U.S.S.N. 14/742,648, filed June 17, 2015, now U.S. Patent 9,518,103, which claims priority under 35 U.S.C. § 119(e) to U.S. provisional patent application, U.S.S.N. 62/013,775, filed June 18, 2014, each of which is incorporated herein by reference.--.

This certificate supersedes the Certificate of Correction issued March 3, 2020.

Signed and Sealed this
Second Day of June, 2020

Andrei Iancu
*Director of the United States Patent and Trademark Office*

CERTIFICATE OF CORRECTION (continued)
U.S. Pat. No. 10,457,715 B2

In Column 1, Lines 15-21, please change the sentence:
"The present application is a continuation of and claims priority under 35 U.S.C. § 120 to U.S. application Ser. No. 14/742,648, filed Jun. 17, 2015, now U.S. Pat. No. 9,518,103, which claims priority under 35 U.S.C. § 119(e) to U.S. provisional patent application Ser. No. 62/013,775, filed Jun. 18, 2014, each of which is incorporated herein by reference."

To:
--This invention was made with government support under grant numbers 1-R01-EB012498-01 and 1DP2OD007428 awarded by the National Institutes of Health (NIH), and under grant number N00014-11-1-0549 awarded by the Office of Naval Research (ONR). The government has certain rights in the invention.--.